(12) United States Patent
Milbrandt et al.

(10) Patent No.: US 12,247,246 B2
(45) Date of Patent: Mar. 11, 2025

(54) IDENTIFICATION OF INHIBITORS OF TCPC AND TIR NADASE ACTIVITY

(71) Applicant: Washington University, St. Louis, MO (US)

(72) Inventors: Jeffrey D. Milbrandt, St. Louis, MO (US); Aaron DiAntonio, St. Louis, MO (US); Kow Essuman, St. Louis, MO (US); Xianrong Mao, St. Louis, MO (US); Yo Sasaki, St. Louis, MO (US); Dan Summers, St. Louis, MO (US)

(73) Assignee: Washington University, St. Louis, MO (US)

( * ) Notice: Subject to any disclaimer, the term of this patent is extended or adjusted under 35 U.S.C. 154(b) by 24 days.

(21) Appl. No.: 18/059,838

(22) Filed: Nov. 29, 2022

(65) Prior Publication Data

US 2023/0272449 A1 Aug. 31, 2023

Related U.S. Application Data

(62) Division of application No. 16/651,196, filed as application No. PCT/US2018/052969 on Sep. 26, 2018, now abandoned.

(60) Provisional application No. 62/563,447, filed on Sep. 26, 2017.

(51) Int. Cl.
| | |
|---|---|
| *C07D 213/20* | (2006.01) |
| *A61K 31/4425* | (2006.01) |
| *A61K 31/4706* | (2006.01) |
| *A61K 31/473* | (2006.01) |
| *A61K 31/4965* | (2006.01) |
| *A61P 31/00* | (2006.01) |
| *A61P 33/00* | (2006.01) |
| *C07D 219/10* | (2006.01) |
| *C07D 241/20* | (2006.01) |
| *C07D 401/06* | (2006.01) |
| *C12Q 1/34* | (2006.01) |

(52) U.S. Cl.
CPC ............ *C12Q 1/34* (2013.01); *A61K 31/4425* (2013.01); *A61K 31/4706* (2013.01); *A61K 31/473* (2013.01); *A61K 31/4965* (2013.01); *G01N 2333/924* (2013.01)

(58) Field of Classification Search
CPC .. C07D 213/20; C07D 219/10; C07D 241/20; C07D 401/06; A61K 31/4425; A61K 31/4706; A61K 31/473; A61K 31/4965; A61P 31/00; A61P 33/00
See application file for complete search history.

(56) References Cited

U.S. PATENT DOCUMENTS

| | | | |
|---|---|---|---|
| 4,241,046 A | 12/1980 | Papahadjopoulos et al. | |
| 4,394,448 A | 7/1983 | Szoka, Jr. et al. | |
| 4,529,561 A | 7/1985 | Hunt et al. | |
| 4,755,388 A | 7/1988 | Heath et al. | |
| 4,828,837 A | 5/1989 | Uster et al. | |
| 4,925,661 A | 5/1990 | Huang | |
| 4,954,345 A | 9/1990 | Muller | |
| 4,957,735 A | 9/1990 | Huang | |
| 5,043,164 A | 8/1991 | Huang et al. | |
| 5,064,655 A | 11/1991 | Uster et al. | |
| 5,077,211 A | 12/1991 | Yarosh | |
| 5,264,618 A | 11/1993 | Felgner et al. | |
| 6,214,824 B1 | 4/2001 | Evans et al. | |
| 9,669,101 B2 | 6/2017 | McArthur | |

FOREIGN PATENT DOCUMENTS

| | | |
|---|---|---|
| JP | 2007061066 A | 3/2007 |
| WO | 9748705 A1 | 12/1997 |
| WO | 2016092499 A1 | 6/2016 |
| WO | 2019067625 A1 | 4/2019 |

OTHER PUBLICATIONS

Abeywickrama C., et al., "Inhibition of Protein Kinase C by Dequalinium Analogues: Structure-Activity Studies on Head Group Variations," Bioorganic & Medicinal Chemistry, vol. 14, No. 23, Dec. 1, 2006, vol. 14, pp. 7796-7803.
Ajeet, "In Silico Designing and Characterization of Amiloride Derivatives as Ion Channel Modulator," Medicinal Chemistry Research, 2013, vol. 22, pp. 1004-1010.
Akira S., et al., "Pathogen Recognition and Innate Immunity," Cell, Feb. 24, 2006, vol. 124, pp. 783-801.
Arnold K., et al., "The Swiss-Model Workspace: a Web-Based Environment for Protein Structure Homology Modelling," Structural Bioinformatics, 2006, vol. 22, No. 2, pp. 195-201.
Askarian F., et al., "A Staphylococcus Aureus TIR Domain Protein Virulence Factor Blocks TLR2-Mediated NF-KB Signaling," Journal of Innate Immunity, Jan. 25, 2014, vol. 6, No. 4, pp. 485-498, DOI: 10.1159/000357618, ISSN 1662-811X, XP055586041.
Berge, et al., "Pharmaceutical Salts," Journal of Pharmaceutical Science, Jan. 1977, vol. 66, pp. 1-19.
Bitter G.A., et al., "Expression and Secretion Vectors for Yeast," Methods in Enzymology, 1987, vol. 153, pp. 516-544.
Burch-Smith T.M., et al., "The Functions of Plant TIR Domains," Science STKE, Aug. 28, 2007, vol. 2007, No. 401, pe46, 1 Page, abstract only.

(Continued)

*Primary Examiner* — Brenda L Coleman
(74) *Attorney, Agent, or Firm* — Polsinelli PC

(57) ABSTRACT

The present invention provides compounds useful as inhibitors of TIR NADase activity, compositions thereof, and methods of using the same. The present invention is useful for inhibition of TIR-domain NADase activity and/or treating microbial infection and/or modulating microbial physiology.

11 Claims, 36 Drawing Sheets

Specification includes a Sequence Listing.

(56) References Cited

OTHER PUBLICATIONS

Canto C., et al., "NAD+ Metabolism and the Control of Energy Homeostasis: A Balancing Act Between Mitochondria and the Nucleus," Cell Metabolism, Jul. 7, 2015, vol. 22, pp. 31-53.

Chong C.R., et al., "A Clinical Drug Library Screen Identifies Astemizole as an Antimalarial Agent," Nature Chemical Biology, Aug. 2006, vol. 2, No. 8, pp. 415-416, 29 Pages(Plus Supplemental Pages).

Cirl C., et al., "Subversion of Toll-Like Receptor Signaling by a Unique Family of Bacterial Toll/Interleukin-1 Receptor Domain-Containing Proteins," Nature Medicine, Apr. 2008, vol. 14, No. 4, pp. 399-406, DOI: 10.1038/NML1734, XP002536697.

Colberre-Garapin F, et al., "A New Dominant Hybrid Selective Marker for Higher Eukaryotic Cells," Journal of Molecular Biology, 1981, vol. 150, 14 pages.

Coles R.B., et al., "Trial of Dequalinium for Skin Infections," The British Medical Journal, Oct. 25, 1958, vol. 2, No. 5103, pp. 1014-1016, XP055586037, Retrieved on [Jan. 8, 2019], Retrieved from URL: https://www.jstor.org/stable/25385404?seq=1#page_scan_tab_contents.

Cone R.D., et al., "High-Efficiency Gene Transfer into Mammalian Cells: Generation of Helper-Free Recombinant Retrovirus with Broad Mammalian Host Range," Proceedings of the National Academy of Sciences, Oct. 1984, vol. 81, pp. 6349-6353.

Elhai J., et al., "Conjugal Transfer of DNA to Cyanobacteria," Methods in Enzymology, Academic Press, Inc, 1988, vol. 167, pp. 747-754.

Essuman K., et al., "The SARM1 Toll/Interleukin-1 Receptor Domain Possesses Intrinsic NAD+ Cleavage Activity that Promotes Pathological Axonal Degeneration," Neuron, Mar. 22, 2017, vol. 93, pp. 1334-1343, 16 Pages.

Essuman K., et al., "TIR Domain Proteins are an Ancient Family of NAD+-Consuming Enzymes," Current Biology, Jan. 25, 2018, vol. 28, No. 3, pp. 421-430, 15 Pages, XP085347131.

Galanakis D., et al., "Synthesis and Pharmacological Testing of Dequalinium Analogues as Blockers of the Apamin- Sensitive Ca2+-Activated K+ Channel: Variation of the Length of the Alkylene Chain," Journal of Medicinal Chemistry, 1996, vol. 39, No. 18, pp. 3592-3595.

Galanakis D., et al., "Synthesis and Quantitative Structure-Activity Relationships of Dequalinium Analogues as K+ Channel Blockers: Investigations into the Role of the Substituent at Position 4 of the Quinoline Ring," Journal of Medicinal Chemistry, 1995, vol. 38, No. 18, pp. 3536-3546.

Galanakis D., et al., "Synthesis and Structure-Activity Relationships of Dequalinium Analogues as K+ Channel Blockers. Investigations on the Role of the Charged Heterocycle," Journal of Medicinal Chemistry, 1995, vol. 38, pp. 595-606.

Ghosh S., et al., "Complete Genome Constellation of a Caprine Group A Rotavirus Strain Reveals Common Evolution with Ruminant and Human Rotavirus Strains," Journal of General Virology, 2010, vol. 91, pp. 2367-2373.

Graeff R., et al., "Mechanism of Cyclizing NAD to Cyclic ADP-ribose by ADP-ribosyl Cyclase and CD38," The Journal of Biological Chemistry, Oct. 2, 2009, vol. 284, No. 40, pp. 27629-27636.

Graeff R.M., et al., "Enzymatic Synthesis and Characterizations of Cyclic GDP-Ribose," The Journal of Biological Chemistry, Dec. 2, 1994, vol. 269, No. 48, pp. 30260-30267.

Graeff R.M., et al., "Fluorescent Analogs of Cyclic ADP-Ribose: Synthesis, Spectral Characterization, and Use," Biochemistry, 1996, vol. 35, No. 2, pp. 379-386.

Hartman S.C., et al., "Two Dominant-Acting Selectable Markers for Gene Transfer Studies in Mammalian Cells," The Proceedings of the National Academy of Sciences, USA, Nov. 1988, vol. 85, pp. 8047-8051.

International Preliminary Report on Patentability for International Application No. PCT/US2018/052969, mailed Apr. 9, 2020, 08 Pages.

International Search Report and Written Opinion for International Application No. PCT/US2018/052969, mailed Jan. 25, 2019, 12 Pages.

Lee A., et al., Site-Directed Mutagenesis of the Yeast PRP20/SRM1 Gene Reveals Distinct Activity Domains in the Protein Product, Molecular Genetics Genomic, 1994, vol. 245, pp. 32-44.

Lee S-J., et al., "Proliferin Secreted by Cultured Cells Binds to Mannose 6-Phosphate Receptors," The Journal of Biological Chemistry, Mar. 5, 1988, vol. 263, No. 7, pp. 3521-3527.

Ogan J., et al., "Adenovirus Tripartite Leader Sequence Enhances Translation of mRNAs Late After Infection," The Proceedings of the National Academy of Sciences, USA, Biochemistry, Jun. 1984, vol. 81, pp. 3655-3659.

Lowy, et al., "Isolation of Transforming DNA: Cloning the Hamster Aprt Gene," Cell, 1980, vol. 22, pp. 817-823.

Mackett M., et al., "General Method for Production and Selection of Infectious Vaccinia Virus Recombinants Expressing Foreign Genes," Journal of Virology, Mar. 1984, vol. 49, No. 3, pp. 857-864.

Mackett M., et al., "Vaccinia Virus: A Selectable Eukaryotic Cloning and Expression Vector," The Proceedings of the National Academy of Sciences, Genetics, Dec. 1982, vol. 79, No. 23, pp. 7415-7419.

Minghui L., et al., "Synthesis and Application of Acridine Derivatives," Chinese Journal of Organic Chemistry, 2018, vol. 38, pp. 594-611.

Mulligan B.C., et al., "Selection for Animal Cells that Express the *Escherichia coli* Gene Coding for Xanthine-Guanine Phosphoribosyltransferase," Proceedings of the National Academy of Sciences of the United States of America, 1981, vol. 78, No. 4, pp. 2072-2076.

O'Hare K, et al., "Transformation of Mouse Fibroblasts to Methotrexate Resistance by a Recombinant Plasmid Expressing a Prokaryotic Dihydrofolate Reductase," Proceedings of the National Academy of Sciences of the United States of America, 1981, vol. 78, No. 3, pp. 1527-1531.

O'Neill O.M., et al., Achalasia: A Review of Clinical Diagnosis, Epidemiology, Treatment and Outcomes, World Journal of Gastroenterology, Sep. 21, 2013, vol. 19, No. 35, pp. 5806-5812.

Panicali D., et al., "Construction of Poxviruses as Cloning Vectors: Insertion of the Thymidine kinase Gene from Herpes Simplex Virus into the DNA of Infectious Vaccinia Virus," Proceedings of the National Academy of Sciences, Aug. 1982, vol. 79, pp. 4927-4931.

Patot S., et al., "The TIR Homologue Lies Near Resistance Gene in *Staphylococcus aureus*, Coupling Modulation of Virulence and Antimicrobial Susceptibility," PLoS Pathogens, Jan. 6, 2017, vol. 13, No. 1, e1006092, pp. 1-23.

Qin D., et al., "Inhibition of Protein Kinase C (alpha) by Dequalinium Analogues: Dependence on Linker Length and Geometry," Journal of Medicinal Chemistry, Apr. 6, 2000, vol. 43, No. 7, pp. 1413-1417.

Rosenberg A., et al., "Vectors for Selective Expression of Cloned DNAs by T7 RNA Polymerase," Gene, 1987, vol. 56, No. 1, pp. 125-135.

Santerre R.F, et al., "Expression of Prokaryotic Genes for Hygromycin B and G418 Resistance as Dominant-Selection Markers in Mouse L Cells," Gene, 1984, vol. 30, pp. 147-156.

Sarver N., et al., "Bovine Papilloma Virus Deoxyribonucleic Acid: a Novel Eucaryotic Cloning Vector," Molecular and Cellular Biology, Jun. 1981, vol. 1, No. 6, pp. 486-496.

Sauve S., et al., "Soil Solution Speciation of Lead(II): Effects of Organic Matter and pH," Soil Science Society of America Journal, May 1998, vol. 62, pp. 618-621.

Shimizu Y., et al., "Cell-Free Translation Reconstituted With Purified Components," Nature Biotechnology, Aug. 2001, vol. 19, pp. 751-755.

Studier F.W., "Protein Production by Auto-Induction in High-Density Shaking Cultures," Protein Expression and Purification, May 2005, vol. 41, No. 1, pp. 207-234.

Szybalska, et al., "Genetics of Human Cell Lines, IV. DNA-Mediated Heritable Transformation of A Biochemical Trait," Proceedings of the National Academy of Sciences of the United States of America, 1962, vol. 48, pp. 2026-2034.

Waldhuber A., et al., "Uropathogenic *Escherichia coli* Strain CFT073 Disrupts NLRP3 Inflammasome Activation," The Journal of Clinical Investigation, 2016, vol. 126, No. 7, pp. 2425-2436.

(56) References Cited

OTHER PUBLICATIONS

Wigler, et al., "Transfer of Purified Herpes Virus Thymidine Kinase Gene to Cultured Mouse Cells," Cell, 1977, vol. 11, pp. 223-232.

Wigler M, et al., "Transformation of Mammalian Cells with an Amplifiable Dominant-Acting Gene," Proceedings of the National Academy of Sciences of the United States of America, 1980, vol. 77, No. 6, pp. 3567-3570.

Yadav M., et al., "Inhibition of TIR Domain Signaling by TcpC: MyD88-Dependent and Independent Effects on *Escherichia coli* Virulence," PLoS Pathogens, Sep. 2010, vol. 6, No. 9, pp. 1-18.

Ying W., "NAD+/NADH and NADP+/NADPH in Cellular Functions and Cell Death: Regulation and Biological Consequences," Antioxidants Redox Signaling, 2008, vol. 10, No. 2, pp. 179-206.

Zhang Q., et al., "TIR Domain-Containing Adaptor SARM is a Late Addition to the Ongoing Microbe-Host Dialog," NIH public Access Author Manuscript, Apr. 1, 2012, pp. 1-16, published in final form as: Developmental and Comparative Immunology, Apr. 2011, vol. 35, No. 4, pp. 461-468.

Zhou C., et al., "Motility and Segregation of Hsp104-Associated Protein Aggregates in Budding Yeast," NIH Public Access Author Manuscript, Nov. 23, 2012, pp. 1-17, published in final edited form as: Cell, vol. 147, No. 5, Nov. 23, 2011, pp. 1186-1196, 17 Pages.

TcpA-TIR / MilB CMP hydrolase

TirS 142 EYDVELSHSSLQKEDYVSKISEKLIEKGLKVFEDVKVFEIDK......SQIETMNMGILNSRFVVLNSRFVVELSPNFIESQMSRYEF 217
MiiB  38 ....................QNVFSRLIEHFESRGTTVYNAHRREAWGAEFLSPAEATRLDHDEIKAADVFVAFP·GVPASPGITHVEI 104

TirS 218 LSFLWREINEEHVIILPIWHKVSVEDVRAYNPYVDKYALNTSD·FSIEDWEKIYQVIVNSKN 280
MiiB 105 GMASGM··G··KPMVLL·LE·RDEDYAFLVTGLESQANVEILRFSGTEEVERLDGAVAR··· 158

FIG. 7C

TcpC 170 HYDFFISHAKEDKDTFVRPVDELNRLGVIIWDEQTLEVG......DSLRBVIDLGLRKMYGIVILSHFLNKKMQYELDSLINRAVYDDMVIILPIWHNI 267
MiiB  38 .......................QNVFSRLIEHFESRGTTVYNAHRREAWGAEFLSPAEATRLDHDEIKAADVFVAFP·GVPASPG·THVEIGWASG·····MGSPMVLLL···· 118

FIG. 7D

TcpA 193 EYDVFICHAHEDKEFFVRELAEKLHBKGLRIVWDEFTLSLG......DNLRSIENGLAKSRYGIVILSKRFFEEKWPQKELDGLV 272
MiiB  38 .......................QNVFSRLIEHFESRGTTVYNAHRREAWGAEFLSPAEATRLDHDEIKAADVFVAFP·GV·PASPGTHVEIGWAS 108

FIG. 7E

SEQUENCE LISTING

```
Sequence total quantity: 43
SEQ ID NO: 1                 moltype = AA   length = 135
FEATURE                      Location/Qualifiers
source                       1..135
                             mol_type = protein
                             organism = Staphylococcus aureus
SEQUENCE: 1
EYDVFLSHSL DKEDYVSKIS EKLIEKGLKF EDVKVFEIGK SQTETMNMGI NSRFVVVFLS   60
PNFIESGWSR YEFLSFLNRE INEHVIILPI WHKVSVEDVR AYNPYLVDKY ALNTSDFSIE  120
EIVEKIYQVI VNSKN                                                   135

SEQ ID NO: 2                 moltype = AA   length = 134
FEATURE                      Location/Qualifiers
source                       1..134
                             mol_type = protein
                             organism = Escherichia coli
SEQUENCE: 2
HYDFFISHAK EDKDTFVRPL VDELNRLGVI WYDEQTLEVG DSLRRNIDLG LRKANYGIVI   60
LSHNFLNKKT QYELDSLINR AVYDNKILPI WHNINAQEVS KYSHYLADKM ALQTSLYSVK  120
EIARELAEIA YRRR                                                    134

SEQ ID NO: 3                 moltype = AA   length = 135
FEATURE                      Location/Qualifiers
source                       1..135
                             mol_type = protein
                             organism = Thermoplasmatales archaeon
SEQUENCE: 3
EYDVFICHAH EDKEFFVREL AEKLHSKGLR VWYDEFTLSL GDNLRRSIEN GLAKSRYGIV   60
VLSKRFFEKE WPQKELDGLV AKEVEGKVIL PVWHGITREE VQSFSSILAN RLAASSEKGI  120
DYVVNEILRV LRKKS                                                   135

SEQ ID NO: 4                 moltype = AA   length = 173
FEATURE                      Location/Qualifiers
source                       1..173
                             mol_type = protein
                             organism = Actinoplanes sp.
SEQUENCE: 4
RYDAFISYSH ADGALAPAVQ RGLQRLARWH RPRALERDQT GLAVSHALWS SIKVALDQSE   60
FFVLLASPEA AASPWVNQEI EHWLSRHSVD RLPVTSGEWV WDADAGDVDL ERSTAVPPAL  120
RGVFGEEPRH LDLRWARAEH ELDLRHGRFR DAIAELAAGM HGMSKEDLDG EDV         173

SEQ ID NO: 5                 moltype = AA   length = 135
FEATURE                      Location/Qualifiers
source                       1..135
                             mol_type = protein
                             organism = Acinetobacter baumannii
SEQUENCE: 5
EYDLFISHAS EDKEDFVRPL AETLQQLGVN WYDEFTLKVG DSLRQKIDSG LRNSKYGTVV   60
LSTDIIKKDW TNYELDGLVA REMNGHKMIL PIWHKITKND VLDYSPNLAD KVALNTSVNS  120
IEEIAHQLAD VILNR                                                   135

SEQ ID NO: 6                 moltype = AA   length = 171
FEATURE                      Location/Qualifiers
source                       1..171
                             mol_type = protein
                             organism = Brucella sp.
SEQUENCE: 6
QAVKVAQEQK RLSDERTKHE AFIKQSLSMR TTASATMEAE EYDFFISHAS EDKEAFVQDL   60
VALRDLGAKF YDAYTLKVGD SLRRKIDQGL ANSKFGIVVL SEIIFFSKQW PARELDGLTA  120
MEIGQTRILP IWHKVSYDEV RRFSPSLADK VALNTSLKSV EEIAKELHSL I           171

SEQ ID NO: 7                 moltype = AA   length = 168
FEATURE                      Location/Qualifiers
source                       1..168
                             mol_type = protein
                             organism = Enterococcus faecalis
SEQUENCE: 7
MSNGKIFISH SKDQEYVDAF IQLLKFGFRT QDIFYSTIET GVQPGELIFD TIKRELTNQP   60
VMLYFLSDHY QSIPCLNEMG ASWMLSDKHY PIALNNFSMK DMKGVISSER LAIAFNDKTS  120
TNEINCLLKK LSHDTDVQAE PDFELNVEKN IQPFQNKLTQ LIRQASYL               168

SEQ ID NO: 8                 moltype = AA   length = 148
FEATURE                      Location/Qualifiers
source                       1..148
                             mol_type = protein
                             organism = Paracoccus denitrificans
SEQUENCE: 8
SAMKPTAGPT NADLTSAPHD IFISHAWEDK ADFVEALAHT LRAAGAEWYD DFSLRPGDSL   60
```

```
RSIDKGLGSR FGIVLSTHFF KKEWPQKELD GLFQLESSCR SRILPIWHKV SKDEVASFSP    120
IMADKLAFNI STKSVDEIVA DLMAIIRD                                       148

SEQ ID NO: 9            moltype = AA   length = 133
FEATURE                 Location/Qualifiers
source                  1..133
                        mol_type = protein
                        organism = Methanobrevibacter olleyae
SEQUENCE: 9
EYDIFVSHSE DKEDFVKEFV NLLKQKGLSV WYDDDIVKIG HNLRKRISKG IKSNYAVIFS     60
EDFFKSKWTN YEYDNIFLDF YDEKVLPILH DLTIEDLEKI DGSIPLIRAL SIKKFTVEEI    120
IHEILERINE EKS                                                       133

SEQ ID NO: 10           moltype = AA   length = 162
FEATURE                 Location/Qualifiers
source                  1..162
                        mol_type = protein
                        organism = Homo sapiens
SEQUENCE: 10
TPDVFISYRN SGSQLASLLK VHLQLHGFSV FIDVEKLEAG KFEDKLIQSV MGARNFVLVL     60
SPGALDKCMQ DHDCKDWVHK EIVTALSCGK NIVPIDGFEW PEPQVLPEDM QAVLTFNGIK    120
WSHEYQEATI EKIIRFLQGR SSRDSSAGSD TSLEGAAPMG PT                       162

SEQ ID NO: 11           moltype = AA   length = 170
FEATURE                 Location/Qualifiers
source                  1..170
                        mol_type = protein
                        organism = Streptomyces rimofaciens
SEQUENCE: 11
GHMTTTPKPR TAPAVGSVFL GGPFRQLVDP RTGVMSSGDQ NVFSRLIEHF ESRGTTVYNA     60
HRREAWGAEF LSPAEATRLD HDEIKAADVF VAFPGVPASP GTHVEIGWAS GMGKPMVLLL    120
ERDEDYAFLV TGLESQANVE ILRFSGTEEI VERLDGAVAR VLGRAGEPTV               170

SEQ ID NO: 12           moltype = AA   length = 152
FEATURE                 Location/Qualifiers
source                  1..152
                        mol_type = protein
                        organism = Rattus norvegicus
SEQUENCE: 12
MRRSVYFCGS IRGGREDQAL YARIVSRLRR YGKVLTEHVA DAELEPLGEE AAGGDQFIHE     60
QALNWLQQAD VVVAEVTQPS LGVGYELGRA VALGKPILCL FRPQSGRVLS AMIRGAADGS    120
RFQVWDYAEG EVETMLDRYF EAYLVEHHHH HH                                  152

SEQ ID NO: 13           moltype = AA   length = 176
FEATURE                 Location/Qualifiers
source                  1..176
                        mol_type = protein
                        organism = Escherichia coli
SEQUENCE: 13
MGSDKIHHHH HHSSGENLYF QGHMSKRVFL AAPFKGAIKE KQSIMKEQEK KRIEDLILFL     60
EEKGWEVDNA HKREEWGANF MSPDQCTKLD YDAIKECDLF IAFPGVPVSP GTHIEIGWAS    120
AMGKKIILLL AEKEENYAYL IRGLHTVSNV HYIIYNKEKE YLQKLDLYLD GENNEV        176

SEQ ID NO: 14           moltype = AA   length = 167
FEATURE                 Location/Qualifiers
source                  1..167
                        mol_type = protein
                        organism = Lactobacillus helveticus
SEQUENCE: 14
MKAVVPTGKI YLGSPFYSDA QRERAAKAKE LLAKNPSIAH VFFPFDDGFT DPDEKNPEIG     60
GIRSMVWRDA TYQNDLTGIS NATCGVFLYD MDQLDDGSAF EIGFMRAMHK PVILVPFTEH    120
PEKEKKMNLM IAQGVTTIID GNTEFEKLAD YNFNECPSNP VRGYGIY                  167

SEQ ID NO: 15           moltype = AA   length = 152
FEATURE                 Location/Qualifiers
source                  1..152
                        mol_type = protein
                        organism = Escherichia coli
SEQUENCE: 15
MRPALYFCGS IRGGREDRTL YERIVSRLRR FGTVLTEHVA AAELGARGEE AAGGDRLIHE     60
QDLEWLQQAD VVVAEVTQPS LGVGYELGRA VAFNKRILCL FRPQSGRVLS AMIRGAADGS    120
RFQVWDYEEG EVEALLDRYF EADPLEHHHH HH                                  152

SEQ ID NO: 16           moltype = AA   length = 157
FEATURE                 Location/Qualifiers
source                  1..157
                        mol_type = protein
                        organism = Lactobacillus leichmannii
SEQUENCE: 16
```

```
MPKKTIYFGA GWFTDRQNKA YKEAMEALKE NPTIDLENSY VPLDNQYKGI RVDEHPEYLH    60
DKVWATATYN NDLNGIKTND IMLGVYIPDE EDVGLGMELG YALSQGKYVL LVIPDEDYGK   120
PINLMSWGVS DNVIKMSQLK DFNFNKPRFD FYEGAVY                            157

SEQ ID NO: 17           moltype = AA   length = 161
FEATURE                 Location/Qualifiers
source                  1..161
                        mol_type = protein
                        organism = Escherichia coli
SEQUENCE: 17
MAHHHHHHMR KIYIAGPAVF NPDMGASYYN KVRELLKKEN VMPLIPTDNE ATEALDIRQK    60
NIQMIKDCDA VIADLSPFRG HEPDCGTAFE VGCAAALNKM VLTFTSDRRN MREKYGSGVD   120
KDNLRVEGFG LPFNLMLYDG VEVFDSFESA FKYFLANFPS K                       161

SEQ ID NO: 18           moltype = AA   length = 161
FEATURE                 Location/Qualifiers
source                  1..161
                        mol_type = protein
                        organism = Escherichia coli
SEQUENCE: 18
MAHHHHHHMR KIYIAGPAVF NPDMGASYYN KVRELLKKEN VMPLIPTDNE ATEALDIRQK    60
NIQMIKDCDA VIADLSPFRG HEPDCGTAFE VGCAAALNKM VLTFTSDRRN MREKYGSGVD   120
KDNLRVEGFG LPFNLMLYDG VEVFDSFESA FKYFLANFPS K                       161

SEQ ID NO: 19           moltype = AA   length = 437
FEATURE                 Location/Qualifiers
source                  1..437
                        mol_type = protein
                        organism = Coprococcus eutactus
SEQUENCE: 19
MKKDVFISYS SKDFDKVNSV KNILEINGIS CWMAPQCIPP GSSYAKEIPM AIKNCKVFLL    60
MLTSKSQESQ WVPKEVSLAL SETKCVIPPV IEDCILTDMF NFFLTDVQRY YAFELQSDSL   120
RELIERIKFE CNKESETVSS FSIDKISDIE TWLISKERNA LNREFSIFLT KLKKMYKDNP   180
NAEMIETWVD KYAVEQYTIR TVMESLDKCS IYLTGVAETK IQLAVIYIHS GVKKYIKDAR   240
NLLNSAIKTY LNQSVYDDVA FKRIVYSKWL IAVTYKQERN FGYANELCED LIDCINDENQ   300
IFEVPYTDSL LLPQRELIVI NKEEIMSDFL LIHMDDISMN PKELFYTQRR LLELYILNND   360
FEKAKGILPE LLSSFDRCKS FVDEIYHVGL YQNLFEYYSY VGDKQSAEKY YRMALENAKR   420
NYWKGKEKKL ENLKQVF                                                  437

SEQ ID NO: 20           moltype = AA   length = 223
FEATURE                 Location/Qualifiers
source                  1..223
                        mol_type = protein
                        organism = Proteus penneri
SEQUENCE: 20
MARCTAPVRG HSSAAAAAAC PACRGRSSYR YSSSYFPASN SGVSYGSSSS SSIPRWSKSG    60
SSIPYTTAQV QSLTPIRETV EERAIKQPDL RDVFLCHAWD DRQGVAKELH DLLEAAGVKV   120
WFSEKDLNLG VPMMRAIDKG LANSRIGLVL VTPALLERIQ REGVADKELS VLLAGNQLVP   180
IVHNTTYEAL RNISPLLASR SGLDTGEDTL EIVATKISEL VTI                     223

SEQ ID NO: 21           moltype = AA   length = 352
FEATURE                 Location/Qualifiers
source                  1..352
                        mol_type = protein
                        organism = Bacteroides thetaiotaomicron
SEQUENCE: 21
MEENKYFAFI SYSRKDLGVA KQIKNNIESI TGKKCWMDME GIESGEQFVD VIVSAIDNSK    60
YVIFLLSDNS MASKYAQKEI TYADKVGKKL IPLNIDRCTP KGWFLFNFGE VDVIDVNVHE   120
QLEKFYSNIK SWSSNQNLEK SFPSLFLDES GQKKVLYLMF LIDSSGSMYG ERMEALNASL   180
ASVFENFSII NPDIDIKINI LQFSSGCQWM YAEPINIEFF RWKLIDARGL TDLGYACHEL   240
DNVMSKKILF SLDNCPAGII PPVLFLITDG EPTDEYLPHM AKLWNNHFFK KSNKFAIGLG   300
GDFSIDALKL FTKNQKQVFT ISDEALNEFK ALVTRLLTMS LYAGSMASLN EE           352

SEQ ID NO: 22           moltype = AA   length = 285
FEATURE                 Location/Qualifiers
source                  1..285
                        mol_type = protein
                        organism = Eubacterium hallii
SEQUENCE: 22
MGVEQYQRKV NSLDKEIADL EKKAEEDRK AADNHKKASR VSVSKNASES MIKSKMRQIE     60
NYEEKARKAE AASADYGKKI SDKRTKRNDA YLKLQKEEQN ERKQKEKSIE NMKRVYEQRI   120
SELESLRLSK VKNEFLETVS GDEPEYDVFV SHAWEDKADF VEAFVQALKD REIKVWYDKS   180
KIKWGDSMRA RIDDGLRKSK FGVAILSPNY IAEGKYWTKA ELDGLFQMES INGKTLLPIW   240
HNLTKKQVMD YSPILASKLA MTTATMTAEE IADELLDMLS SEEDK                   285

SEQ ID NO: 23           moltype = AA   length = 413
FEATURE                 Location/Qualifiers
source                  1..413
                        mol_type = protein
```

```
                            organism = Bacteroides thetaiotaomicron
SEQUENCE: 23
MDHEVFISYS SANIQTAQAI CHALESNRIK CWMAPRDIRP GAEYGDIIEE AIVTCKVFLI     60
VFSETSQISR WVRSELNIGF SSNKPIIPFR IDPTDLKGSM KLMLNDKHWL NAYPNPEEKF    120
SELAAVILDL LQHPAVDTIS PPGFQPASNV ASADGSNAGA QGLFGKLLNQ LFVKRRVKVT    180
SDHAAEIFLN GERKGKLDAY ETGNYSVSED FYQLEVYSCE YGKKVKCEYS GSFSNSSTVI    240
ISVDMATAEK QYLMKAKNIT SGQINDLGII FLDEGKFEDA QECFLKAASM GEAAAAYNLG    300
MMYHFGKGVE IDYDVAREYY EEAVKSDYPL ALNNLGSIYY NGHGVRKDIA KSFPYFCRAA    360
ERGVESAQFT VATMLFYGQG VAVDKAKAKK WFQKAAAQGC KDSQNYLNSW VDD           413

SEQ ID NO: 24              moltype = AA   length = 173
FEATURE                    Location/Qualifiers
source                     1..173
                           mol_type = protein
                           organism = Bacteroides xylanisolvens
SEQUENCE: 24
MALNRFYLTE NSIAQRSGLC IFISHQKRDA DTAKKIADYF ITSGIDVYFD EYDTKIDRTR     60
PYSVVSAIKT GIRNSTHMLC LLSQNALDSK WIPWEVGYGY DRTTVVGLTL KEISQSVLPE    120
YLQIVPILRG TKSLNNFISN VLKRDESTLI NERKLFAAYQ SQHPLDSVLN WEL           173

SEQ ID NO: 25              moltype = AA   length = 482
FEATURE                    Location/Qualifiers
source                     1..482
                           mol_type = protein
                           organism = Clostridium scindens
SEQUENCE: 25
MKEDRIPKIF ISYSWSSDAI VLELAQRLVS HGVDVVLDKW DLKEGQDKYA FMERCVNDTE     60
ITKVLIVCDK VYAQKANDRT GGVGDETVII SSEIYGNTKQ EKFIPVIAEK SEDGKAYVPT    120
YIKTRIYIDL SDPETYEIEY EKLLRNIYEK PQFTKPKLGK MPEWLDEEKT DFFQLKDLIR    180
QIHGSNTDNK RKSCISRFQI THIEVLKGYI EKNASPERVY EIFLNTKPVR DFYLKFVETI    240
AETETDYAEI IAEGFETMYN QLTCIKAFVP NANSVSQNDL DIFKIYIWEL FICVIAFMRH    300
IKDYAAINEM LTYTYPLETS IFGGSIKPNN YTAFRHHSCV IEEYYKPKTE MKNKYTLMGD    360
VICNQREKLP IYTGEAIAEA DLFLYQVCNA YELSEKEQSW HKVYWFPTCY VYVKNMPIEW    420
EKMKSRRYCD KMMVLFGVDS LEDLKTVISR CTFDSGMKYP GSWDAAPAIL NCIQIEDIGM    480
LS                                                                  482

SEQ ID NO: 26              moltype = AA   length = 200
FEATURE                    Location/Qualifiers
source                     1..200
                           mol_type = protein
                           organism = Dorea formicigenerans
SEQUENCE: 26
MKYYYDVVLS FAGEDREYVE ECADILTALG IKVFYDSYEQ DVLWGKDLYT FLADIYSNKA     60
RYAIVFISQH YVKKCWTKHE FKFINERMFN SETEYLLPVF LDDTKLCGIP ETQGYLTNKT    120
PYEVAVMFAK KINKDIDVEL MKSELQQSLP TYEITVRGRN VRFYSAVEEF DAEYPLSFLM    180
ELYKLDMMYD LFILPELVPN                                               200

SEQ ID NO: 27              moltype = AA   length = 136
FEATURE                    Location/Qualifiers
source                     1..136
                           mol_type = protein
                           organism = Providencia rustigianii
SEQUENCE: 27
MNIFVSYTTR DDNVNKKLLE RVSEIVSLYG HCYIDLLHNT KKDKQQHVEF MLSQSNLLIL     60
IASSSVFTSK WVQWELDEAK RCYIPIIMVE AKSDMNNILK NLKSILATNA YLLSNHRSEK    120
FKNSSENTMS LLGGNV                                                   136

SEQ ID NO: 28              moltype = AA   length = 267
FEATURE                    Location/Qualifiers
source                     1..267
                           mol_type = protein
                           organism = Bacteroides coprophilus
SEQUENCE: 28
MSSSKNLFVS ISYQDNLDH KRWVSKLAQT LKNEGFKVLV DIFNLHGGED INEFMENVII     60
HSDKVLIIMT QGYKEKADKR FAGAGYEAKL IANLIKENQH TRKFIPIKRD KDDCIPNFLK    120
PLVFIDMSDD NLFNEKIEDL LLAISGSDSD YDDLIREINY QIDSLQPYEE YYGDTIPLIE    180
QKKYQLSLKV QNAQSEHNFL EVIKYKIQIA QICQEQNKSQ DAYKLEEGIR EAYAMLSDFE    240
KVQAKSIIAD YNSDMALYID QDINRNK                                       267

SEQ ID NO: 29              moltype = AA   length = 287
FEATURE                    Location/Qualifiers
source                     1..287
                           mol_type = protein
                           organism = Bacteroides thetaiotaomicron
SEQUENCE: 29
MNSSYYQNQI NRLEKDIADL QKKIADENKK EIDNKQIDS VHRTINKNTS ISTLNSKQRQ     60
IDGYQKDILN CRTKIASYQK SIATKSAELG KKRQELLKAQ QSEQKKLQDD QLKFQKKLQS    120
EIEIQKRHLE TLIAQNYSTQ NNKLVSTEDI PEPTKQYDFF ISHASEDKDD IVRDLAEALR    180
NNGFEVWYDE FELKIGDSLR KKIDYGLSNA NYGIVIISPS FVKKNWTEYE LNGMVAREMN    240
```

```
GHKVILPIWH KITKDEVLRF SPSLADKLAL NTSIHTIDDI VENLKNL                287

SEQ ID NO: 30            moltype = AA   length = 413
FEATURE                  Location/Qualifiers
source                   1..413
                         mol_type = protein
                         organism = Bacteroides thetaiotaomicron
SEQUENCE: 30
MDHEVFISYS SANIQTAQAI CHALESNRIK CWMAPRDIRP GAEYGDIIEE AIVTCKVFLI    60
VFSETSQISR WVRSELNIGF SSNKPIIPFR IDPTDLKGSM KLMLNDKHWL NAYPNPEEKF   120
SELAAVILDL LQHPAVDTIS PPGFQPASNV ASADGSNAGA QGLFGKLLNQ LFVKRRVKVT   180
SDHAAEIFLN GERKGKLDAY ETGNYSVSED FYQLEVYSCE YGKKVKCEYS GSFSNSSTVI   240
ISVDMATAEK QYLMKAKNIT SGQINDLGII FLDEGKFEDA QECFLKAASM GEAAAAYNLG   300
MMYHFGKGVE IDYDVAREYY EEAVKSDYPL ALNNLGSIYY NGHGVRKDIA KSFPYFCRAA   360
ERGVESAQFT VATMLFYGQG VAVDKAKAKK WFQKAAAQGC KDSQNYLNSW VDD          413

SEQ ID NO: 31            moltype = AA   length = 492
FEATURE                  Location/Qualifiers
source                   1..492
                         mol_type = protein
                         organism = Roseburia intestinalis
SEQUENCE: 31
MFDAFISHSS KDKEKIVLEL VQKLEKNNID VWLDANEILA GDTILDAVEK GVATALCTIL    60
IITPAFFESF WTPVEIGLAI GQNNNHKLIP VLCNVSVEDI AQRFPMLLSL KYIKLDPDNI   120
DLCVDELCSN IIQIKKKYEK DFPEISFHKA VKKFHSCDTP TANTISILLS EYEQIVEINV   180
RTAVLHASQI AITIINDLFM RLPIKGNSVD TTIGKLDLIK VSSIGLTENV YEHLKLLSTP   240
ALDTNMSLLT NDLDRRKLAE MSMTAILEWY SKYLLHNKII PQDRFEIVWP DDLSYEDFIT   300
MYEIDCLVLR EDLIAPPSIT YAWYQYNNYT HIAVRSTETN RIVGYFTVLP VTDQLYEDIQ   360
SGYFKDNDLN TDNLRKYDVP DFYKLYIACV CIHPDYQNTS AFRKLYNALL QMMMDLAVER   420
EIYITNIITE ASTLQGEKFC KILGLNCMLN TEIETKIYGA TLLPPSWQLR SSFGSKLMKY   480
YKEKYEELKD LF                                                      492

SEQ ID NO: 32            moltype = AA   length = 439
FEATURE                  Location/Qualifiers
source                   1..439
                         mol_type = protein
                         organism = Bacteroides ovatus
SEQUENCE: 32
MKYKYDVFIS YSRRDYVDES YNVIPGNAIA EIQNVFDENG ITYWFDKDGI YSGQEFIEII    60
TGAIAESKIL IFISSKHSNE SMWTAGEIFE ALDGEKAIIP VKIDNSQYNK KFKLLIRPLD   120
YIDYLENPKN ALKDLLRAIN KVKEDIAQKQ REEEKLREER EAEAAKKEKIK KEISVLAKDC   180
QRLTLQQIDV VNQIFEKQIY IGNTTKICPI CDKEVSISSN FCNRCGWTFP ILYCIDENNT   240
YPLDEEQLSI ARTNWCSIIK NSLEPEKQPL KSSPLQATEE HKSMTDNKYA LQNAMDEIET   300
LRKYLLDERT KVKEIQEEYE NLLKVQKNIE LKQEVPSARE IGNIIILDKFS TTNSKKYQSF   360
KNKNDVFNFV RSFCKARFLT LNPSCYVADI QYTDLKDALY EKYNIHIGEH TLKCHSTLYK   420
LVDSIWNEYT KHSNSDASR                                                439

SEQ ID NO: 33            moltype = AA   length = 291
FEATURE                  Location/Qualifiers
source                   1..291
                         mol_type = protein
                         organism = Clostridium bolteae
SEQUENCE: 33
MSSEQYQRTV NSLDKEIADL EKKAAKDRE VANLQGKINT LKKSINSHTS ASTLNSKMRQ     60
IAIHESDQAK KSQDSADLGK KIAEKRKKRA EAYLRLQKEQ QNEQKKQDKV NQQIQASYEA   120
RIKELQQQLL QPVVTTTTTP IAADEEYDVF VSHAYEDKES FVDEFVEALR NQELKVWYDM   180
DKLKWGDSMR EKIDRGLAKS RYGVVILSPN YIAEHKYWTK AELNGLFQVE TVNGKTILPI   240
WHNLTKKQVV EYSPIIADRK AMTTALMTPE EIAAELKELF TAEDTEDENN G            291

SEQ ID NO: 34            moltype = AA   length = 706
FEATURE                  Location/Qualifiers
source                   1..706
                         mol_type = protein
                         organism = Eubacterium cylindroides
SEQUENCE: 34
MEQTEAKEIY QMGVEALNDC DYRMAGAYFK NAAKMNYKPA IAALEKLILE GKYKNVQSKQ    60
TLSSNTESKE LFEKGVDYYK GRNNTKIDYV KAFECFLSSS IDGYAFAMNW LGYCYEYGKG   120
TKKNLDSAFG WYEKAANANV ANAIYHLGRL YDGKGVQQD YNKAFGLFKK ACDLRESLAY    180
EYLADCYFYG QGTKINYEKA LQFYLKVKPR GVIEYQIGCI YARGLSTGSD YPKAAEHFQK   240
GVDFGHAPSM NNLGALYYNG EGVQKDYNKA FELFKKASDL GYTTAHGWLA DCYYYGNGAK   300
KDYQKALQLY LKAKSSRHNE GQIGYIYEHG LGTPIDINKA IEHYQKGVDL GCTGCMHNLG   360
TLYYKGEGCQ KDYNKAFELF KKASDLGEIA AHGWLAKCYF YGYGTQKDYQ KAIEHYQKSI   420
DPFGNTDSMIS LGILYYEGKG IQQDYQKAFE LFKKSSDLEN KTAHAWLAEC YYYGNGTKKD   480
YQKALQLYLK GNLYGYTQSQ IGRIYESGQG VKKNLTEALN WYKKANESGK DCKADIERIN   540
NLLNKKPENK SIDKTKVETK ANSNKPIKAY EGDKPYIFVS YSHTDSKVVK EVLQMLINQG   600
YRIWFDEGIR AGSSWTENLM NHIKNASHFI FFLSRHSINS KYCLKELRFA DRRNKIIIPI   660
CIENVNVSDE IDFLLGEVQM LFKNNLEKEE FMEKFNSSNH IEICSR                  706

SEQ ID NO: 35            moltype = AA   length = 280
```

| FEATURE | Location/Qualifiers |
|---|---|
| source | 1..280 |
| | mol_type = protein |
| | organism = Enterococcus phage |

SEQUENCE: 35
```
MSINSLQQKE KSLLSDITKL EGDYAREQKK IANSEKKIAD SSKKIESSKS ISTIRSQSRI    60
KESETKKSLA SKEKSATISS KLAKKRKELG DIQVKLSKQR TIENTQFQKN LKKTYDTQIM   120
KIKETQTAAL QNVQSELPND PSLVNKTYDL FISYASDDSE YVDKLTQAFT NEGFSIWRDK   180
SDIAWGQSIR QSIDAGLSNS KFGLVVLSSK YIEKFWTNYE LDGILNKESA TGRQMILPLW   240
HNITKDEIDK KSPSLSNRLA LDTRINSTND IINAFKSLLE                        280
```

| SEQ ID NO: 36 | moltype = AA  length = 1808 |
|---|---|
| FEATURE | Location/Qualifiers |
| source | 1..1808 |
| | mol_type = protein |
| | organism = Leptolyngbya sp. |

SEQUENCE: 36
```
MSNTVSPSAS KSFKNAFISY GRADSLDFAK WLNDKLVDQG YDIWFDFENI PQGVDYQKQI    60
DAGIENADNF IFVIAPHATN SPYCRKEVEL AIALNKRLVP IMHVEEISRE TWQGRNPNGT   120
DEQWEAYKTE GLHSCFTNLH PELGKINWNQ VSFKEGVNDY EQSFQALVDI FERQSNYVRQ   180
HTEFLDGALK WERGQKQSQL LLDEEQTLRA QHWLQTKFHG EQPPCVPTDL HCEFITESLK   240
RLPNGMSQLF FAHANSDTET MQSLRQQMRR AGYSVWTPEA DIQSGQDVQA EILRGIEGAD   300
SFIYLMSSQS LESSDCQSQL QYAQTLKKRI IPIRLESIGS DTLPANQQKF SWIDCTSDEA   360
ASKQLAIAQV LKAIKEESSF YEQHRQILVK ALSWDRQKRP KSLLLQGQDF TLAEQWLALS   420
KTEQSSRATD LQQIYIKASQ EMNQFFDVFI SYGRADSKDF ATILHDRLVE QGFNVWFDQN   480
DIPLGVDFQE QINAGIEKAH NFLFIIAPHS VNSPYCGKEV DLALDLNKRI IPILHVEEIS   540
KETWQQRNPY KTEESDWEEA QKQGAHSSFN NMNPEIGKIN WVYCREQDDF EASFEGLMTL   600
CRQHEDYVKQ HTEILAKALS WESHQKQSQY LLVGENRIEA EKWLLTRFTE TQAPCFPTDL   660
HCEYITESIK NANNLMTQVF LSHSDEDQEI EDKVRRSLMR EGYTVWSSQR DIEAGVDFNA   720
AINRGIETTD NIVYLLSPNS LASEYCQKEI DYALSLNKRI IPLNIAAVDE TNLPAAIQSL   780
QYIDLTNGIE DETYQARLNE LLKILNQDKA YFEEHKAILV RGLKWQAQQK NNSILLRGHN   840
LREAEAWLKL AAKRSEYAAT PLHQEFIQAS LDQLEDVALD VFVSYSRSDS DFVRQLNDAL   900
QVQGKTTWFD QENIASGTDF QAEIFQGIET CDNLFVISP NSVNSPYCAG EVEHAAKLGK    960
RFVTVLHQSV SSASLHPELE KVQWIDFNKN DGDPFYANFE LIRTLDTDRE HVRSHTKWSQ  1020
RALDWVNKKR GKDLLLRGNE FAIAENWLKE ADDGKKTPKP TTLQRDFLIA SKEAIEAAIR  1080
REKRISMIIR TLLGVVSVAC VIAFIQYRQA NFQRKRAERV QEGQINALSD YSVSLLENHQ  1140
DLQSLIEAIR AGRQLQLQLK TVDQSTVDAV TTTLRDALLN IEEVNRITGH PSAQGINAVA  1200
YSPDESMVAT GGADGNIRLW SAEGESIRTL EDHEAPIYEM EFSPNGKFLL SGSEDFTARL  1260
WDPETGELLR TFEDHDNSIY GVSFSPDSQI IATASVDGTV NIYSVEGQLL QTLEIDLENY  1320
DVSFNADGSA IATASEDGIL RFWDLEGELR NEVEAHENGI STVAFSPKGD LVATGSWDQT  1380
AKLWTIDGES VVTLQGHTDE VNHLFFSDDG EFLVTTSYDN LAKVWSREGE LLHTIRGHED  1440
GVLGVAISKD SSTVKTTSLD GTARVWDISS LPNVKTFEDQ TADIFEVEFS PDEKWIGSAG  1500
DSGARIWDLE GNLISDLDGE NNAMRDLAFS QDGRYLATGE ENGVVKIWEW TGDNFKLVQT  1560
VQNEDAGKMR AIAFHPEGKY LATAGDGVTV QLWTLDGESV FVSEVADWTN SIAFSPDGEF  1620
LISGGWDQMI SLWDLEGNLL NSWEAHPDSI NGLAFGNDAQ TIISASNDQT AQIWQLDGAS  1680
GSPTLTVNHG AEVNKATLSP DGKNLITVGG QTVKFWDLEG RLLQTIAAHN DIIYGFALSS  1740
DGKQFVTGSY DSTARLWSYQ PKVSEKATEI WQLDLNALVD HACGVARNYL TFNPDVSDSD  1800
RLLCEPDL                                                          1808
```

| SEQ ID NO: 37 | moltype = AA  length = 166 |
|---|---|
| FEATURE | Location/Qualifiers |
| source | 1..166 |
| | mol_type = protein |
| | organism = Modestobacter marinus |

SEQUENCE: 37
```
MVSYTPTEWR TVEPYAEKAV EQARVNPDRR DLFLCHAWDD RQGSAAELHG LLKTNGATVW    60
FSEEDLPLGS LMIREIDKGL RNSRIGIVLV TPALLKSIEK EGIAEKELAV LLNSKRVIPV   120
THGVTYEQLL DISPMLASHA GLSTKESSLD DVAAKLAAAA AALPAL                 166
```

| SEQ ID NO: 38 | moltype = AA  length = 237 |
|---|---|
| FEATURE | Location/Qualifiers |
| source | 1..237 |
| | mol_type = protein |
| | organism = Scytonema sp. |

SEQUENCE: 38
```
MTDPLIVSGT ANDIDSLRQP LVAGSIGVQQ QVIPQLANLG DTGLDVLMEF LFERRENPAT    60
SVDGKAYQVL YNSDSPKAKE FLQTYFPFGI VPLTSDGGID YSPLQQLLAT QDFQAADRMT   120
LQKMCELAGS AAVQRKWLYF TEVENFPITD LKTINTLWLV HSEGKFGPTV QREIWLGLGK   180
NWENLWTKIG WKKGNNWTRY PNEFTWNLSA PRGHLPLSNQ LRGVRVIASL LSHPAWN     237
```

| SEQ ID NO: 39 | moltype = AA  length = 147 |
|---|---|
| FEATURE | Location/Qualifiers |
| source | 1..147 |
| | mol_type = protein |
| | organism = Comamonas aquatica |

SEQUENCE: 39
```
MRRSIESRAA LPDLRDIFLC HAWDDRQGAA KELHDQLESR GVSVWFSEKD VALGTSLLRE    60
IDKGLAKSRV GIVLVTPSLL SRVRGEGIAE KELSALLARD LLVPIVHDTT YEALRDVSPL   120
LGSRSGLSTK DASMAAVAAK LAELVAV                                     147
```

```
SEQ ID NO: 40          moltype = AA  length = 245
FEATURE                Location/Qualifiers
source                 1..245
                       mol_type = protein
                       organism = Lacunisphaera limnophila
SEQUENCE: 40
MSRCTAPIRG HNSASAAENC PVCRYKSRGY SSYSSNYDSY NSSRFSSSSG SNGSSSTSRG   60
NYNVSKGRTI KPSWSRSTSP IYYTPAEVKT LTPVRENVEK RVVKEDLRDV FLCHAWDDRK  120
GSAKDLHDLL ELKGVSVWFS EKDVIIGSSL LREIDKGLAR SKVGIVLVTP KFLERIKNEG  180
IADKELSALL ARDLLVPIVH ETTFEELRDE SPLLGSRSGL STLEDSMENI ASKLAELVSD  240
KLIVI                                                              245

SEQ ID NO: 41          moltype = AA  length = 1102
FEATURE                Location/Qualifiers
source                 1..1102
                       mol_type = protein
                       organism = Lacunisphaera limnophila
SEQUENCE: 41
MSDPGKAVFL SYASQDAEAA KRICDALRAA GVEVWFDQNE LVGGDQWDGK IRGQISSCAL   60
FVPLISANTQ ARLEGYFRLE WKLAAQRTHT MADEMTFLLP VLIDGTRDAE ARVPAEFRAV  120
QWTKLPAGEA TPAFCVRVRK LLDGTAAGVV DPGLPGSTSP ATSRPVPPRR GASKWWWVLP  180
IFGVTMAMVL VMKEARKEPA PSSSNGPAPT MTQPVSEARK LANQAMQLLE DPNFTRETSW  240
LADELCQRAL ALDAGDAEVW AVAAFASHNL FSNTYDTSAG RREKARSQAA RASQVDPQSV  300
RAALAVARCL EGTGNDGELL RILQELHRRA PADQQVLFSL VRAEGGMGNE TAVQDLIRKF  360
RALPRTGLFP LALWFEELRL RTLGRYAEAE AMLDEMLADP GVLRGAYYEK LNLLMRSWHD  420
LAAAAPFIEK IPARFRQEPA FGSAIAYYWL WRAEPEKALQ ALAQVPQDYF EEYAAREPKG  480
YLTGWAHAIA KRPAAAQAEW RAALTLVDER LKTDARNPSL LNQRALLLAL TGQREAAREA  540
WQLRVELGGE QNPVGLEAET QVLVALNEPE AALAAIEREW SRRKPMGRVR ALPVIRYHPA  600
YAVIRGDPRL QRILKEDEAE LHVLKEQQTR SAPAKEPTTA SSAADAKSVA VLAFANLSDD  660
KANEYFSDGI SEELLNVLAK VPGLKVAART SAFYFKGKEV PIPEIARQLG VAYVLEGSVR  720
KQGDKVRITA QLIKAADGFR VWSDTFTRDL KDIFAVQDEI AGLIAKNLEL KMSMGESVPR  780
QAVRPDAYQA FLLGRSAAAK ASVVELREAV GHFERAVALE PKYTAAWVQL ASIHTRLGRW  840
GGAPTLASWA AARAAIDQAL ALEPESPDVL LAQGWILRTA EWDWRGAERS FRRALALQPN  900
NPEILAGTAV LLFNIGQTEE AFRLARLAVQ LDPLNPSTQI DLSIMFFESK NWVESERAAR  960
RALQLAPGGT SYHSVLAWPL INQGRYAEAE ASLALDLDVV QQSGTRGLLG LARGDLAMVR 1020
EMLARLEQLA RTEPDRADLQ TCTAWLYAGL GDKDRAFAAL EKARISRDPS IAWLRENTEL 1080
TPLFSDPRWQ ELMRKVGLAD GQ                                         1102

SEQ ID NO: 42          moltype = AA  length = 327
FEATURE                Location/Qualifiers
source                 1..327
                       mol_type = protein
                       organism = Aquimarina amphilecti
SEQUENCE: 42
MKNRSYEYDV ALSFAGENRA YVERVANSLK TKGVKVFYDL FEEANLWGKN LYEYLSEIYQ   60
NKARYTVLFV SSFYNKKLWT NHERVSMQAR AFQESREYIL PARFDDTEIP GILKTIGYIN  120
LENRTPEELA VLIENKLKKD QTFFKNRWSK LSTMISPKPF IFTIKVVDEK SQLVKHAKVV  180
LVANNSTYLE GYTDENGLAH FVIRTRKLYT VLIAHSEYPA VVFKSMNPKE DIEVTIEKTN  240
NSGSVIINKS GQIPGISGKI EPVLKSDKNL SVYADNIAIE GGKDQPYDFE LNKSIVLEDN  300
KGNIVHLTFR FYQARIALID FYRGRSM                                     327

SEQ ID NO: 43          moltype = AA  length = 891
FEATURE                Location/Qualifiers
source                 1..891
                       mol_type = protein
                       organism = Thioflavicoccus mobilis
SEQUENCE: 43
MPGYDLFLSY NRRDRAIVDP LAGALCERGL KVFKDDWFLR PGEPWPLALE KSLMASRAVA   60
VAVGRNGLGP WQQREAAAAL DLQARRPPDD GLPVIPVLLD QDSARQAGLA FLLQNTWVEH  120
WDPRAADLIV GAVQGKAPAE LYDTRDADPR TRVCPYRGLG VFREEDAGFY VGRESDLERL  180
GDAIERHPVV AVVGASGSGK SSLVRAGLIP RLRRASGTRV YQVADMMPGR GPFLALARAL  240
LPLREPERVL SWSKGGIDDE CERLSAKLDQ NGAEHLTHVV GQILAEEPGT TQLLLLVDQW  300
EELYTYRPSE AAALRRHGER VRRFIGMLLE AARLCPLQVV LTLRADYWGE VLNDEPLAAA  360
LCDPALVHLR ALDRAAALERV IRHPAERVGL QVPDALAEVL LDAAAGQPGD LPLLEFTLQQ  420
LWAERADHGG TLTLDAYRAM GGLEKAIVSR AETTLDRLAP AEREAVPGLF AALVQVGEAR  480
TDLRRRARLA ELGEPARAAA CQLANERLLV TGRDWTSGEE WVEVAHEALL RHWPKLEGWI  540
DTRRGALLTV RQLQADTRTW LESGKRSGFL WSHERAREAA KALTQLGMEV SLSSEEAEFL  600
GPIDPQAMLA ELEQPQTDHQ RRALIGARLD LLGDPRPGIG CTPGGTPDIA WYPVGGEVT  660
IEVERLIRGG TKPKVKAIAP FHIARYPVTV TQYRAFLQAE DGWRDPWWA NDLDRDPEGD  720
SYDLGRYDNH PALYVSWFDA MAYCRWLSNR LGLLIRLPDE WEWQQAATGG DAAQIFPWGA  780
EWNPKTEPCR ANTFEARLGG VTAVGMYPAG ASPGGVVDMA GTVWEWCLNK HDSPLATESR  840
PDNFDRRVVR GGSWYVVQSY ARSAARYRSN PSSRDSGLGF RVLCASPIPG H          891
```

IDENTIFICATION OF INHIBITORS OF TCPC AND TIR NADASE ACTIVITY

GOVERNMENTAL RIGHTS

This invention was made with government support under NS087632 awarded by the National Institutes of Health. The government has certain rights in the invention.

FIELD OF THE INVENTION

This application relates to various compounds and compositions, and methods, useful for inhibition of TIR-domain NADase activity and/or treating microbial infection and/or modulating microbial physiology.

MATERIAL INCORPORATED-BY-REFERENCE

The Sequence Listing, which is a part of the present disclosure, has been submitted in Extensible Markup Language (.xml) and is hereby incorporated by reference in its entirety. The XML copy, created May 18, 2023, is named 047563-654448-1.xml, and is 51,649 bytes.

BACKGROUND

Antimicrobial resistance has emerged as one of the principal public health problems of the 21st century that threatens the effective prevention and treatment of an ever-increasing range of infections caused by bacteria, parasites, viruses and fungi no longer susceptible to the common medicines used to treat them. Without effective antimicrobials for prevention and treatment of infections, medical procedures such as organ transplantation, cancer chemotherapy, diabetes management and major surgery (e.g., caesarean sections or hip replacements) become very high risk. The problem of antimicrobial resistance is especially concerning regarding antibiotic resistance in bacteria. For instance, resistance in *Escherichia coli* to one of the most widely used medicines for the treatment of urinary tract infections (fluoroquinolone antibiotics) is very widespread. There are countries in many parts of the world where this treatment is now ineffective in more than half of patients. Moreover, resistance to first-line drugs to treat infections caused by *Staphylococcus aureus*, a common cause of severe infections in health facilities and the community, is widespread. People with methicillin-resistant *Staphylococcus aureus* (MRSA) are estimated to be 64% more likely to die than people with a non-resistant form of the infection. Hence, much effort and resources have been devoted to understanding resistance mechanisms and discovery of novel classes of antibiotics.

Accordingly, a need exists for compounds and compositions which are useful for treating microbial infections. Additionally, methods for screening potential compounds and compositions useful for treating microbial infections are critical to the discovery of novel antimicrobial agents.

SUMMARY

Among the various aspects of the present disclosure provide enzyme(s) as therapeutic target(s) for microbial infections and disease.

In some embodiments, the present disclosure provides assays for identifying and/or characterizing a TIR NADase inhibitor. In one aspect, the present disclosure provides certain vector constructs and polypeptides for use in these assays, including wild-type, mutant or fragments of microbial or mammalian TIR domain polypeptides, as well as tagged versions of the same. In another aspect, the disclosure provides compositions comprising a polypeptide and a solid support which is used for screening TIR NADase inhibitors.

The present disclosure further provides methods of using TIR NADase inhibitors to treat or prevent a microbial infection. In some embodiments, the disclosure provides administering an effective amount of a composition comprising an inhibitor of TcpC TIR NADase activity. In one aspect, the TcpC NADase inhibitor compositions treat infection and disease caused by uropathogenic *Escherichia coli*. In another aspect, the disclosure provides administering compositions comprising dequalinium, cetylpyridium, amiloride or combinations thereof, for use as inhibitors of TcpC NADase activity.

In some embodiments, the disclosure provides inhibitors of TirS NADase. In one aspect, TirS NADase inhibitors treat infection and disease caused by *Staphylococcus aureus*. In another aspect, the disclosure provides the recognition that acrinol, akrinol or combinations thereof are useful as inhibitors of TirS NADase activity.

In certain embodiments, the present invention relates to Tir NADase inhibitor compositions and methods for decreasing the infectivity, morbidity, and rate of mortality associated with a variety of pathogenic organisms. In some embodiments, inhibitors of TIR NADase activity are selected from dequalinium, cetylpyridium, amiloride, acrinol, akrinol, analogs or derivatives thereof, or a pharmaceutically acceptable salt thereof. Compounds of the present invention and pharmaceutically acceptable compositions thereof, are useful for treating a variety of infections, infectious diseases, or conditions.

Compounds provided by this invention are also useful for the study of TIR NADase activity in biological and pathological phenomena; the study of microbial physiology; and the comparative evaluation of new TIR NADase activity inhibitors in vitro or in vivo.

While multiple embodiments are disclosed, still other embodiments of the present invention will become apparent to those skilled in the art from the following detailed description, which shows and describes illustrative embodiments of the invention. Accordingly, the figures and detailed description are to be regarded as illustrative in nature and not restrictive.

BRIEF DESCRIPTION OF THE FIGURES

* FIG. 1A depicts the *E. coli* metabolite assay to screen candidate TIR domains for NAD+ cleavage activity. FIG. 1B shows the SARM1 domain structure and role in axon degeneration. MLS-Mitochondrial Localization Signal; ARM-Armadillo/HEAT Motifs; SAM-Sterile Alpha Motif; TIR-Toll/Interleukin 1 Receptor. FIC. 1C shows the domain structure of candidate prokaryotic TIR containing proteins. CC-Coiled Coil; Ax_dyn_L—Axonemal dynein light chain; TM—transmembrane; ATP_Syn_B—ATP Synthase B/B' CF(0); MPN—Mpr1p Pad1p N-terminal. FIG. 1D shows the endogenous levels of $NAD^+$ in *E. coli* after IPTG induction. Data were generated from at least three independent biological experiments. Data are presented as mean±SEM; error bars represent SEM. $P<0.001$ for SARM1-TIR, ApTir-TIR, AbTir-TIR, TcpA-TIR, TcpO-TIR for individual comparisons (+/−IPTG) using unpaired, two-tailed Student's t test. P<0.01 for TcpC-TIR, TcpF-TIR, BtpA-TIR, for individual comparisons (+/−IPTG) using unpaired, two-tailed Student's t test. P<0.05 for Pd-TIR for individual comparisons (+/−IPTG) using unpaired, two-tailed Student's t test. P<0.001 for TirS-TIR IPTG v.s. NC vector IPTG.

FIG. 2A shows prokaryotic TIR proteins purified from cell-free translation system cleave $NAD^+$ in NADase assay. FIG. 2B is a HPLC chromatogram showing the TIR domain from *Staphylococcus aureus* (TirS-TIR) cleaves $NAD^+$ into Nam and ADPR. FIG. 2C is a HPLC chromatogram showing the TIR domain from uropathogenic *Escherichia coli* (TcpC-TIR) cleaves NAD+ into Nam and ADPR. FIG. 2D is a HPLC chromatogram showing the TIR domain from the archaea *Thermoplasmatales archaeon* (TcpA-TIR) cleaves $NAD^+$ into Nam and ADPR. Retention time was as follows: Nam at t~2.40 min and ADPR at t~1.10 min. FIG. 2E is the quantification of metabolites generated by prokaryotic TIR proteins as displayed in 2A-2D (normalized to 0 min). Data were generated from at least three independent reaction experiments. Data are presented as mean±SEM; error bars represent SEM. P<0.001 for all individual comparisons between 0 and 5 min or between 0 and 30 min for each TIR. FIG. 2F is the kinetic parameters for TirS-TIR and TcpC-TIR $NAD^+$ cleavage reaction. $V_{max}$ and $K_m$ were determined by fitting the data to the Michaelis-Menten equation and are presented as mean±SEM for two independent purified protein reactions. FIG. 2G depicts amino acid sequence alignment of TirS-TIR with MilB cytidine 5' monophosphate (CMP) hydrolase, and modeling of TirS-TIR domain on the crystal structure of CMP hydrolase bound to CMP. E216 of TirS aligns with the catalytic glutamate residue of CMP hydrolase (SEQ ID NO:1 and SEQ ID NO:11). FIG. 2H depicts amino acid sequence alignment of TcpC-TIR with CMP hydrolase, and modeling of TcpC-TIR domain on the crystal structure of CMP hydrolase bound to CMP. E244 of TcpC aligns with the catalytic glutamate residue of CMP hydrolase (SEQ ID NO:2 and SEQ ID NO:11). Tan—modeled bacterial TIR; cyan—MilB CMP hydrolase; yellow—cytidine-5'-monophosphate (ligand for MilB). FIG. 2I depicts purified TIR proteins with mutation of catalytic glutamate to alanine do not cleave $NAD^+$ in NADase assay (normalized to control at 0 min). FIG. 2J-FIG. 2K show the quantification of metabolites from reactions using purified proteins (TirS-TIR and TcpC-TIR) and substrate analogs (NADP—Nicotinamide Adenine Dinucleotide Phosphate; 3apAD—3-acetylpyridine Adenine Dinucleotide; sNAD—thionicotinamide Adenine Dinucleotide; NHD—Nicotinamide Hypoxanthine Dinucleotide; NGD—Nicotinamide Guanine Dinucleotide; NaAD—Nicotinic Acid Adenine Dinucleotide; NADH—Nicotinamide Adenine Dinucleotide reduced; NMN—Nicotinamide Mononucleotide; ATP—Adenosine triphosphate; GTP—Guanine triphosphate). Metabolites were measured by HPLC and LC-MS analyses, and normalized to 0 min controls. FIG. 2L is a heat map summarizing relative levels of substrates after 30 minutes of reaction with the purified TIR proteins indicated. Values range from 0 (green), indicating complete cleavage of substrate within 30 minutes, and 1 (red) indicating relatively unchanged levels of substrates. Data from (IL) were generated from at least three independent reaction experiments. Data are presented as mean±SEM; error bars represent SEM.

FIG. 3A-FIG. 3D are HPLC chromatograms of metabolites extracted from *E. coli* lysates expressing candidate prokaryotic TIR domains. Metabolites extracted from TcpO-TIR, and AbTir-TIR reveal a prominent previously unidentified peak (labeled "X") around retention time 1.7 minutes (FIG. 3C-FIG. 3D), which is not seen in metabolites extracted from SARM1-TIR or TirS-TIR (FIGS. 3A and 3B). FIG. 3E is a HPLC chromatogram showing purified TcpO-TIR cleaves $NAD^+$ into Nicotinamide, ADPR, and a metabolite close to retention time of Metabolite X. FIG. 2F is a HPLC chromatogram of cADPR standard. FIG. 3G shows a merge of HPLC chromatograms of metabolites generated from purified TcpO-TIR recombinant protein reaction (FIG. 3E) cADPR standard (FIG. 3F). FIG. 3H shows MS/MS spectra of product ion scan of m/z 542 of cADPR standard and TcpO-TIR generated metabolite X. FIG. 3I depicts the proposed structure of variant cADPR generated by TcpO-TIR with the N7 adenine position involved in cyclization.

FIG. 4A Endogenous $NAD^+$ levels in HEK293 cells expressing both wild type and mutant TirS-TIR and TcpC-TIR. FIG. 4B depicts a western blot of wild type and mutant TirS-TIR and TcpC-TIR proteins expressed in HEK293T cells. FIG. 4C shows a HPLC chromatogram showing purified full length TirS (TirS-FL) cleaves NAD+ into Nam and ADPR in NADase assay. FIG. 4D is the quantification of metabolites generated by TirS-FL NADase reaction as displayed in C (normalized to 0 min NAD+). FIG. 4E shows SYPRO Ruby gel of purified TirS (wild type and mutant). FIG. 4F shows endogenous NAD+ levels in HEK293T cells expressing both wild type and mutant TirS-FL. FIG. 4G depicts western blot of wild type and mutant TirS-FL proteins expressed in HEK293T cells. Data were generated from at least three independent experiments. Data are presented as mean±SEM; error bars represent SEM. ***p<0.001, unpaired two-tailed Student's t test.

FIG. 5A and FIG. 5B shows multiple sequence alignments of prokaryotic TIR domain containing sequences used in *E. coli* IPTG experiments. Sequences were aligned using the ClustalO multiple sequence alignment tool in HH Pred (SEQ ID NOs:1-10).

(FIG. 6A-FIG. 6F) Nicotinamide and ADPR were detected by mass spec in reactions catalyzed by TirS-TIR, TcpC-TIR, and TcpA-TIR. FIG. 6G depicts trace amount of cADPR were detected in the reactions catalyzed by TcpA-TIR, but not TirS-TIR or TcpC-TIR.

FIG. 7A, FIG. 7B, FIG. 7C, FIG. 7D and FIG. 7E show multiple sequence alignments and structure modeling of prokaryotic TIRs with MilB CMP hydrolase. FIG. 7A is a SYPRO gel showing purified proteins (wild type and mutant) used in NADase assay time course. FIG. 7B shows modeling of the TcpA-TIR domain on the crystal structure of CMP hydrolase bound to CMP. E267 aligns with the catalytic glutamate residue of CMP hydrolase. (FIG. 7C-7E) Amino acid sequence alignment of TirS-TIR, TcpC-TIR, and TcpA-TIR with MilB cytidine 5' monophosphate (CMP) hydrolase. CMP catalytic glutamic acid is highlighted by the red asterisk and aligns to a conserved glutamic acid in the prokaryotic TIR domains (SEQ ID NOs:1-3 and 11).

FIG. 8A are chemical structures of NAD+ and nucleotide analogs tested in NADase assay. Functional groups highlighted in red depict modifications in analogs compared to NAD+. Nucleotide analogs include NADP—Nicotinamide Adenine Dinucleotide Phosphate; 3apAD—3-acetylpyridine Adenine Dinucleotide; sNAD—thionicotinamide Adenine Dinucleotide; NHD—Nicotinamide Hypoxanthine Dinucleotide; NGD—Nicotinamide Guanine Dinucleotide; NaAD—Nicotinic Acid Adenine Dinucleotide; NADH—Nicotinamide Adenine Dinucleotide reduced; NMN—Nicotinamide Mononucleotide; ATP—Adenosine triphosphate; GTP—Guanine triphosphate. (FIG. 8B and FIG. 8C) Quantification of metabolites from reactions using purified proteins (TcpA-TIR and SARM1-TIR) and nucleotide analogs from A. Metabolites were measured by HPLC and LC-MS analyses, and normalized to 0 min controls.

FIG. 9A is a HPLC chromatogram of metabolites extracted from *E. coli* lysates expressing BtpA-TIR reveal a prominent, previously unidentified peak labeled X. FIG. 9B is a cADPR standard and Metabolite X from purified TcpO-TIR reaction have similar parent ion m/z of 542, but different retention times. The retention time for Metabolite X differ from than shown in A and FIG. 4 since these are two separate LC instruments. (FIG. 9C-FIG. 9E) The ion pair of 542/136 is confirmed in metabolites extracted from *E. coli* lysates expressing TcpO-TIR, AbTir-TIR, and BtpA-TIR.

FIG. 10A depicts the primary screen of compounds from the Pharmacon library identified Dequalinium as a potent inhibitor of the NADase activity of TcpC TIR. FIG. 10B depicts a dose response is shown for Dequalinium tested as an NADase inhibitor of the TIR domain from TcpC, *Staph aureus* TirS (called N=MSSA above), and SARM1 (called SAM-TIR). Note that dequalinium is a very potent inhibitor of TcpC-Tir with an IC50 of approximately 300 nM. FIG. 10C shows the inhibition by cetylpyridium of the NADase activity of the TIR domain from TcpC, *Staph aureus* TirS (called N=MSSA above), and SARM1 (called SAM-TIR). FIG. 10D shows the inhibition by amiloride of the NADase activity of the TIR domain from TcpC, *Staph aureus* TirS (called N=MSSA above), and SARM1 (called SAM-TIR).

FIG. 11A shows the primary screen of inhibitors from the Pharmakon library identified Acrinol and Akrinol as inhibitors of the NADase activity of the TirS Tir domain of MSSA inhibitors. FIG. 11B depicts components of acrinol and akrinol and additional acridine compounds (listed in figure) were tested as inhibitors of the NADase activity of TirS. The most potent inhibition is mediated by 9-Aminoacridine. FIG. 11C, structure of Acrinol; FIG. 11D, structure of Akrinol (9-aminoacridine and 4-hexylresorcinol).

Figure 1A:
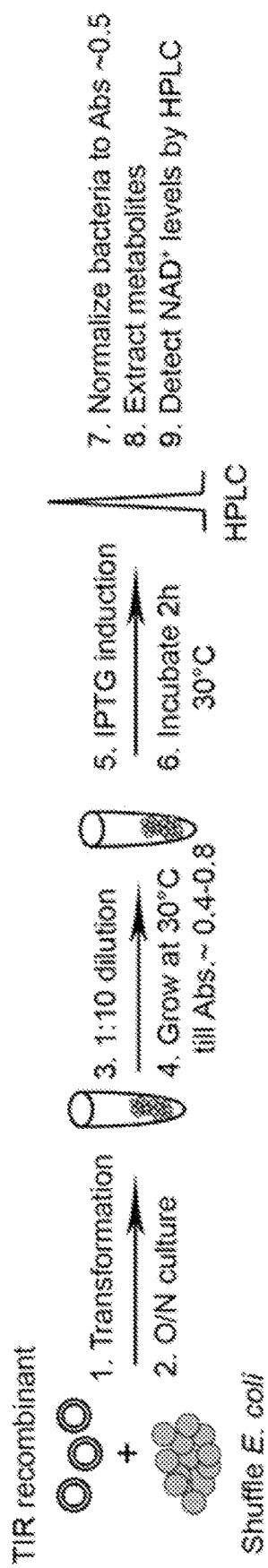
FIG. 1A, FIG. 1B and FIG. 1D shows multiple TIR domains from bacteria and archaea induce $NAD^+$ loss in host *E. coli

Reference to various embodiments does not limit the scope of the invention. Figures represented herein are not limitations to the various embodiments according to the invention and are presented for exemplary illustration of the invention.

DETAILED DESCRIPTION

The present disclosure provides, generally, methods and compositions for inhibiting NADase activity of TIR domain containing polypeptide. In particular, provided herein are compositions comprising TIR NADase inhibitor compounds such as dequalinium, cetylpyridium, amiloride, acrinol, akrinol, derivatives thereof or pharmaceutically acceptable salts thereof. Applicants have surprisingly discovered TIR domains constitute a new family of NADase enzymes. Hence, this large class of proteins is a central and previously unappreciated regulator of NAD+ biology and represents a new therapeutic window for modulating the virulence and/or survival of microbes.

Traditionally, the TIR domain is known as the signature domain of components of Toll-Like Receptor (TLR) signaling, and is present in numerous receptors and adaptor proteins in innate immune pathways (Akira et al., 2006; Burch-Smith and Dinesh-Kumar, 2007; O'Neill et al., 2013). These TIR domains serve as scaffolds that promote the assembly of signaling complexes to trigger activation of pro-inflammatory cytokines and other defense-related products (O'Neill et al., 2013). Bioinformatics analysis shows that TIR domains are present in proteins across all domains of life. In bacteria, TIR domain proteins are associated with virulence, and are thought to do so, in part, via blockade of innate immunity mediated by TLR signaling. While, a number of individual TIR domains from the pathogenic bacteria have been analyzed, the TIR domains from these pathogenic bacteria seem to differ in their modes of action and their roles in virulence. As a result targeting these domains for therapeutic intervention has been challenging and largely unsuccessful.

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular compound is disclosed and discussed and a number of modifications that can be made to a number of molecules of the compound are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

Various aspects of the invention are described in further detail in the following sections.

(I) Compositions

One aspect of the present disclosure provides an inhibitor of TIR NADase activity. As used herein, an inhibitor of TIR NADase activity, or "TIR NADase inhibitor" includes any compound capable of downregulating or inactivating the NADase activity of a TIR domain containing polypeptide. In some embodiments, the inhibitors for use with the invention may function to inhibit the NADase activity of a TIR domain containing polypeptide, thereby increasing the concentration of NAD+ in a biological sample compared to that of a control or decreasing the concentration of one or more of ADPR, cADPR or nicotinamide relative to a control. In some embodiments, compounds that decrease TIR NADase activity also decrease the associated downstream signaling pathways.

A composition of the invention may optionally comprise one or more additional drug or therapeutically active agent in addition to the TIR NADase inhibitor. A composition of the invention may further comprise a pharmaceutically acceptable excipient, carrier, or diluent. Further, a composition of the invention may contain preserving agents, solubilizing agents, stabilizing agents, wetting agents, emulsifiers, sweeteners, colorants, odorants, salts (substances of the present invention may themselves be provided in the form of a pharmaceutically acceptable salt), buffers, coating agents, or antioxidants.

Other aspects of the invention are described in further detail below.

(a) Dequalinium, Cetylpyridium, Amiloride, Acrinol, Akrinol, and Derivatives Thereof In general, the compounds detailed herein include compounds comprising dequalinium, structure as diagrammed below. Dequalinium is a bis-quinolinium compound. Its chemical elements are expressed as $C_{30}H_{40}N_4$, with a molecular weight of 527.578 g/mol. Dequalinium and its salts are commercially available, for example from Sigma Aldrich. Methods of making suitable derivatives are described in U.S. application Ser. No. 14/657,872, WO 97/48705, Galanakis et al. (1995) J. Med. Chem. 38: 595-606, Galanakis et al (1995) J. Med. Chem. 38: 3536-3546 and Galanakis et al (1996) J. Med. Chem. 39: 3592-3595, Abeywickrama et al. (2006) Bioorganic Medicinal Chem. 14: 7796-7803, Qin et al. (2000) J. Med. Chem. 43: 1413-1417, Campos Rosa et al (1996) J. Med. Chem. 39: 4247-4254, the contents of which are incorporated herein by reference in their entirety.

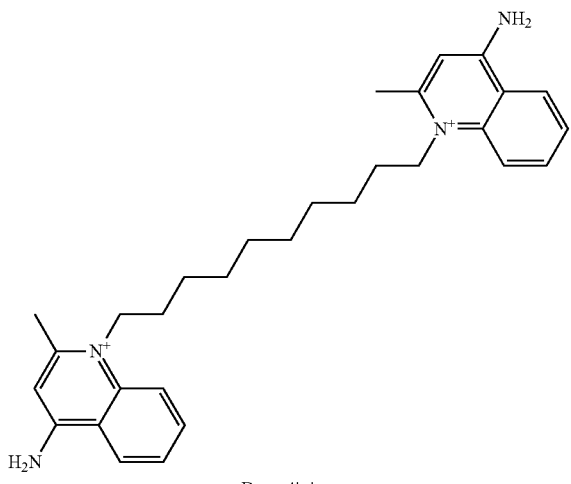

Dequalinium

Suitable derivatives of dequalinium include but are not limited to: 1-decanyl-2-methyl-4-aminoquinolinium iodide; 1-butyl-2-methyl-4-aminoquinolinium iodide; 1,1,1-triethyl-1-(10-iododecan-1-yl)ammonium iodide, 1-[1-(N,N,N-triethylammonium-1-yl)-2-methyl-4-aminoquinolinium diiodide; 1,1'-(decane-1,10-diyl)bis(4-aminopyridinium) diiodide; 1-(4-pentyn-1-yl)-4-aminopyridinium chloride; 1,1'-(deca-4,6-diyne-1,10-diyl)bis(4-aminopyridinium)dichloride dehydrate; 2,2'-N,N'-(decane-1,10-diyl)bis(2,4-diaminopyridine); 2,2'-N,N'-(decane-1,10-diyl)bis(2-aminopyridine); 2,2'-N,N'-(decane-1,10-diyl)bis(1-methyl-2-aminopyridinium)diiodide; 1-(4-pentyn-1-yl)-2-methyl-4-aminoquinolinium iodide; 1,1'-(deca-4,6-diyne-1,10-diyl)bis(4-amino-2-methylquinolinium)diiodide hydrate; 1,1'-(decane-1,10-diyl)bis(quinolinium)diiodide; 1,1'-(decane-1,10-diyl)bis(9-amino-1,2,3,4-tetra-hydroacridinium) dibromide hydrate; 2,2'-(decane-1,10-diyl)bis(quinoline); 2,2'-(decane-1,10-diyl)bis(1-methylquinolinium)diiodide hydrate; 2,2'-(decane-1,10-diyl)bis(4-methoxyquinoline); 2,2'-(decane-1,10-diyl)bis(1-methyl-4-methoxyquinolinium)diiodide; 2,2'-(dodecane-1,12-diyl)bis(1-methylquinolinium)diiodide; 2,2'-(decane-1,10-diyl)bis(isoquinolinium)diiodide; 1,1'-(decane-1,10-diyl)bis(4-bromoisoquinolinium)diiodide; 1,1'-(decane-1,10-diyl)bis(1H-benzimidazole); 1,1'-(decane-1,10-diyl)bis(3-methylbenzimidazolium)diiodide hemihydrate; 1,1'-(decane-1,10-diyl)bis(2-methylbenzimidazole); 1,1'-(decane-1,10-diyl)bis(2,3-dimethylbenzimidazolium) diiodide; 1,10-bis[N-(acridin-9-yl)amino]decane dihydrochloride dihydrate; 1,1'-(1,10-Decanediyl)bis[4-amino-2-methyl quinolinium]diiodide; 1,1'-(1,10-Decanediyl)bis[4-aminoquinolinium]diiodide; 1,1'41,10-Decanediyl)bis[4-N,N,dimethylaminoquinolinium]diiodide; 1,1'-(1,10-Decanediyl)bis[2-methylquinolinium]diiodide; 1,1'-(1,10-Decanediyl)bis[quinolinium]diiodide [0195] 1,6-Bis[N-(1-methylquinolinium-2-methyl)amino]hexane diiodide; 1,1'-(1,10-Decanediyl)bis[1-amino isoquinolinium] diiodide; 1,1'-(1,10-Decanediyl)bis[2-methylbenzoxazolium]diiodide; 1,1'41,10-Decanediyl)bis [2-methylbenzothiazolium]diiodide; 1,1'-(1,10-Decanediyl) bis[2-amino-1-methylbenzimidazolium]diiodide; 1,1'-[(E)-5-Decene-1,10-diyl]bis[4-amino-2-methylquinolinium], diiodide; 1,1'-[(Z)-5-Decene-1,10-diyl]bis[4-amino-2-methylquinolinium], diiodide; 1,1'41,12-Dodecanediyl)bis[4-amino-2-methylquinolinium], diiodide; 1,1'-(1,14-Tetradecanediyl)bis[4-amino-2-methylquinolinium], diiodide; 1,1'-(1,16-Hexadecanediyl)bis[4-amino-2-methylquinolinium], diiodide; N-Decyl-4-aminoquinaldinium Iodide; 1,1'-[Biphenyl-3,3'-diylbis(methylene)]-bis(4-aminoquinolinium); Dibromide Hydrate; 1,1'-[Biphenyl-4,4'-diylbis(methylene)] bis(4-aminoquinolinium)Ditrifluoro-acetate; 1,1'-(Phenanthrene-3,6-diylbis(methylene)]bis(4-aminoquinolinium)Dibromide Hydrate Ethanoate; 1,1'-[Fluorene-2,7-diylbis(methylene)]-bis(4-aminoquinolinium) Ditrifluoroacetate; 1,1'-[Methylenebis(benzene-1,4-diylmethylene)]bis(4-aminoquinolinium)Dibromide Hydrate; 1,1'-[Ethylenebis-(benzene-1,4-diylmethylene)]bis (4-aminoquinolinium)Dibromide Hydrate; (Z)-1,1'-[Stilbene-4,4'-diylbis(methylene)]-bis(4-aminoquinolinium)Dibromide Sesquihydrate; (E)-1,1'-[Stilbene-4,4'-diylbis(methylene)]-bis-(4-aminoquinolinium)Dibromide Dihydrate; 1,1'-[Ethyne-1,2-diylbis(benzene-1,4-diylmethylene)]bis(4-aminoquinolinium)Dibromide Sesquihydrate; 1,1'-[Propane-1,3-diylbis(benzene-1,4-diylmethylene)]bis (4-aminoquinolinium)Dibromide Hemihydrate Ethanoate; 1,1'-[Pyridine-2,6-diylbis(benzene-1,4-diylmethylene)]-bis (4-aminoquinolinium)Dibromide Hydrate; 1,1'-[Butane-1,4- diylbis(benzene-1,4-diylmethylene)]bis-(4-aminoquinolinium)Dibromide Hydrate; 1,1'-[1,1:4',1"-Terphenyl-4,4"-diylbis(methylene)]bis(4-aminoquinolinium)Dibromide Trihydrate; 1,1'-[Naphthalene-2,6-diyl(bis(methylene)]bis(4-aminoquinolinium)Dibromide Hydrate; 1,1'-[Benzene-1,4-diylbis(methylene)]-bis(4-aminoquinolinium)Dibromide Dihydrate; 1,1'-[Benzene-1,3-diylbis(methylene)]bis(4-aminoquinolinium)Dibromide Hemihydrate; 1,1'-(Propane-1,3-diyl)bis(4-aminoquinolinium)diiodide; 1,1'-(Butane-1,4-diyl)bis(4-aminoquinolinium)diiodide; 1,1'-(Pentane-1,5-diyl)bis(4-aminoquinolinium)diiodide [0225] 1,1'-(Hexane-1,6-diyl)bis(4-aminoquinolinium)diiodide; 1,1'-(Octane-1,8-diyl)bis(4-aminoquinolinium)diiodide; 1,1'-(Dodecane-1,12-diyl)bis(4-aminoquinolinium)dibromide hemihydrate; 1,10-Bis[N-(2-methylquinolin-4-yl)amino]decane; 1,12-Bis[N-(2-methylquinolin-4-yl)amino]dodecane; 1,10-Bis[(2-methylquinolin-4-yl)amino]decane; 1,12-Bis[(2-methylquinolin-4-yl)amino]dodecane; 1,10-Bis(N-quinolin-4-ylamino)decane; 4,4'-[Decane-1,10-diylbis(oxy)]bis[quinoline]; 4,4'-[Decane-1,10-diylbis(thio)]bis[quinoline]; 4,4'-Dodecane-1,12-diylbis[quinoline]; 1,8-Bis(N-quinolin-4-yldiamino)octane; 1,8-Bis[N-(1-methylquinolinium-4-yl)amino]octane Diiodide Hydrate; 1,10-Bis[N-(1-methylquinolinium-4-yl)amino]decane Diiodide; 4,4'-[Decane-1,10-diylbis(oxy)]bis[1-methylquinolinium]Diiodide; 4,4'-[Decane-1,10-diylbis(thio)]bis[1-methylquinolinium]Diiodide Hydrate; 1,1'-Dimethyl-4,4'-dodecane-1,12-diylbis[quinolinium]Diiodide; 4,4'-Decane-1,10-diylbis[quinoline]; 1,1'-Dimethyl-4,4'-decane-1,10-diylbis[quinolinium]Diiodide; 1,10-Bis[N-(1-benzylquinolinium-4-yl)amino]decane Dibromide; 1,10-Bis[N-(1-benzyl-2-methylquinolinium-4-yl)amino]-decane Bis(trifluoroacetate); 1,12-Bis[N-(1-benzyl-2-methylquinolinium-4-yl)amino]-dodecane Bis(trifluoroacetate); 1-[N-(1-Benzyl-2-methylquinolinium-4-yl)amino]-10-[N'-(2-methylquinoliniu-m-4-yl)amino]decane Bis(trifluoroacetate); 1-[N-(1-Benzyl-2-methylquinolinium-4-yl)amino]-12-(N'-(2-methylquinolinium-4-yl)amino]dodecane Bis(trifluoroacetate)-3,5-Dimethoxybenzyl iodide; 1,10-Bis[N-[1-(3,5-dimethoxybenzyl)-2-methylquinolinium-4-yl]amino-]decane Bis(trifluoroacetate); 1-[N-[1-(3,5-Dimethoxybenzyl)-2-methylquinolinium-4-yl]amino]-10-[N'-(2-m-ethylquinolinium-4-yl)amino]decane Bis(trifluoroacetate); 1,1'(3-Iodopropylidene)bis[benzene]; 1,10-Bis[N-[1-(3,3-diphenylprop-1-yl)-2-methylquinolinium-4-yl]amino]decane Bis(trifluoroacetate); 4,7-Dichloro-1-methylquinolinium Iodide; 1,10-Bis[N-(7-chloro-1-methylquinolinium-4-yl)amino]-decane Diiodide Dihydrate.

In some embodiments, the compounds detailed herein include compounds comprising cetylpyridinium, structure as diagrammed below. Cetylpyridinium is a cationic quaternary ammonium compound as described in The Merck Index (The Merck Index, 11th Ed.; Merck & Co., Rahway, N.J. (1989); p. 311). Its chemical elements are expressed as $C_{21}H_{38}CN^+$, with a molecular weight of 304.542 g/mol. Cetylpyridinium and its salts are commercially available, for example from Sigma Aldrich. Cetylpyridinium may be obtained by quaternization of pyridine with cetyl chloride. Methods of making suitable derivatives are described in WO 2016092499 A1, the contents of which are incorporated herein by reference in its entirety.

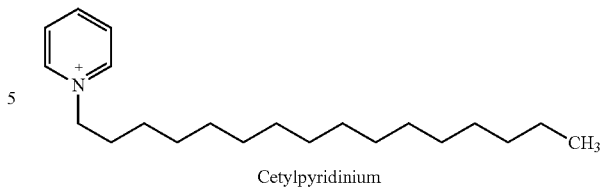

Cetylpyridinium

In some embodiments, the compounds detailed herein include compounds comprising amiloride, structure as diagrammed below. Amiloride, also known as Midamor or 3,5-diamino-6-chloro-N-(diaminomethylidene)pyrazine-2-carboxamide, is a pyrazine compound. Its chemical elements are expressed as $C_6H_8ClN_7O$, with a molecular weight of 229.628 g/mol. Amiloride is commercially available, for example from Chemieliva Pharmaceutical Co., Ltd. Methods of making amiloride and suitable derivatives are described Medicinal Chemistry Research February 2013, Volume 22, Issue 2, pp 1004-1010, Biochimica et Biophysica Acta (BBA)—Biomembranes Volume 1146, Issue 1, 23 Feb. 1993, Pages 59-64, U.S. Pat. No. 6,214,824 B1, the contents of which are incorporated herein by reference in their entirety. Suitable amiloride derivatives include but are not limited to, 5-(N-Ethyl-N-isopropyl)amiloride; 5-(N,N-Dimethyl)amiloride hydrochloride; 5-(N-Methyl-N-isobutyl)-amiloride; and 5-(N,N-Hexamethylene)amiloride.

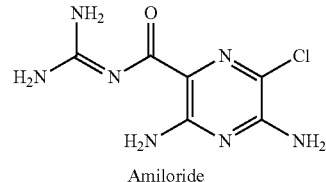 [SMILES: NC(N)=NC(=O)c1nc(Cl)c(N)nc1N]

Amiloride

In some embodiments, the compounds detailed herein include compounds comprising acrinol, structure as diagrammed below. Acrinol, also known as ethacridine monolactate monohydrate, 6,9-Diamino-2-ethoxyacridine-DL-lactate monohydrate, and Rivanol, is an aromatic organic compound based on acridine. Its chemical elements are expressed as $C_{18}H_{21}N_3O_4$, with a molecular weight of 343.383 g/mol. Acrinol is commercially available, for example from Chemieliva Pharmaceutical Co., Ltd. Methods of making acrinol and suitable derivatives are described Chinese Journal of Organic Chemistry 38(3):594 (2018), the contents of which are incorporated herein by reference in their entirety. Suitable acrinol derivatives include but are not limited to, 6,9-Dichloro-2-methoxyacridine; 9-Amino-6-chloro-2-methoxyacridine; (4-(9-Acridinylamino)phenoxy) acetic acid; 2-[4-(Acridin-9-ylamino)phenoxy]pentanoic acid 2-[4-(acridin-9-ylamino)phenoxy]butanoic Acid; 2-[4-[(4-methylacridin-9-yl)amino]phenoxy]propanoic acid; 2-[4-(Acridin-9-ylamino)phenoxy]propanoic acid; 2-[4-[(4-methylacridin-9-yl)amino]phenoxy]butanoic acid; Ethacridine lactate monohydrate; (6,9-diamino-2-ethoxyacridin-1-yl) 2-hydroxypropanoate hydrate; 2-ethoxyacridine-1,3-diamine with 2-hydroxypropanoic acid; 7-ethoxyacridine-1,3-diamine with 2-hydroxypropanoic acid; 6-ethoxyacridine-3,9-diamine with 2-hydroxypropanoic acid; 7-ethoxyacridine-2,3-diamine with 2-hydroxypropanoic acid; and 1,3-Dihydroxy-9-acridinecarboxylic acid.

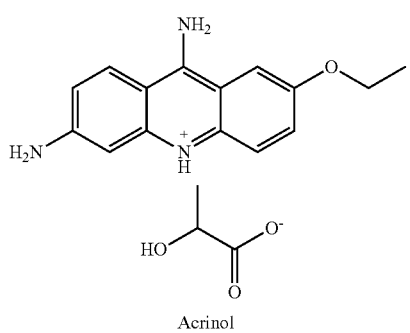

Acrinol

In some embodiments, the compounds detailed herein include compounds comprising akrinol, structure as diagrammed below. Akrinol, also known as acrisorcin, is comprised of two active ingredients, 9-aminoacridine and 4-hexylresorcinol. Its chemical elements are expressed as $C_{25}H_{28}N_2O_2$, with a molecular weight of 388.511 g/mol. Akrinol is commercially available, for example from Chemieliva Pharmaceutical Co., Ltd. Suitable akrinol derivatives include but are not limited to, 2-(acridin-9-ylamino) benzene-1,3-diol.

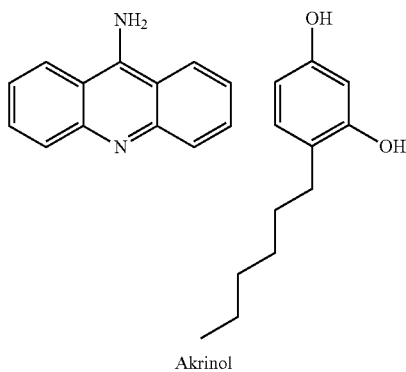

Akrinol

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention. Such compounds are useful, for example, as analytical tools, as probes in biological assays, or as therapeutic agents in accordance with the present invention.

(b) Components of the Composition

The present disclosure also provides pharmaceutical compositions. The pharmaceutical composition comprises a TIR NADase inhibitor, as an active ingredient, and at least one pharmaceutically acceptable excipient.

The pharmaceutically acceptable excipient may be a diluent, a binder, a filler, a buffering agent, a pH modifying agent, a disintegrant, a dispersant, a preservative, a lubricant, taste-masking agent, a flavoring agent, or a coloring agent. The amount and types of excipients utilized to form pharmaceutical compositions may be selected according to known principles of pharmaceutical science.

In each of the embodiments described herein, a composition of the invention may optionally comprise one or more additional drug or therapeutically active agent in addition to a TIR NADase inhibitor. Thus, in addition to the therapies described herein, one may also provide to the subject other therapies known to be efficacious for treatment of the disease, disorder, or condition. In some embodiments, the additional drug or therapeutic agent maybe a small molecule, a polypeptide, a nucleic acid, a cell or parts thereof, and antibody or the like. In some embodiments, the administration of a TIR NADase inhibitor maybe administered before concurrently or after administration of an additional drug or therapeutic agent. In some embodiments, the additional drug or therapeutically active agent induces anti-inflammatory effects. In some embodiments, the secondary agent is selected from a corticosteroid, a non-steroidal anti-inflammatory drug (NSAID), an intravenous immunoglobulin, a kinase inhibitor, a fusion protein, a monoclonal antibody directed against one or more pro-inflammatory cytokines, and a combination thereof. In some embodiments, anti-inflammatory drugs include, but are not limited to, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, curcumin, deflazacort, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen picolnol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, lysofylline, meclofenamate sodium, meclofenamic acid, meclorisone dibutyrate, mefenamic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecorlimus, mepolizumab, prodrugs thereof, and a combination thereof.

(i) Diluent

In one embodiment, the excipient may be a diluent. The diluent may be compressible (i.e., plastically deformable) or abrasively brittle. Non-limiting examples of suitable compressible diluents include microcrystalline cellulose (MCC), cellulose derivatives, cellulose powder, cellulose esters (i.e., acetate and butyrate mixed esters), ethyl cellulose, methyl cellulose, hydroxypropyl cellulose, hydroxypropyl methylcellulose, sodium carboxymethylcellulose, corn starch, phosphated corn starch, pregelatinized corn starch, rice starch, potato starch, tapioca starch, starch-lactose, starch-calcium carbonate, sodium starch glycolate, glucose, fructose, lactose, lactose monohydrate, sucrose, xylose, lactitol, mannitol, malitol, sorbitol, xylitol, maltodextrin, and trehalose. Non-limiting examples of suitable abrasively brittle diluents include dibasic calcium phosphate (anhydrous or dihydrate), calcium phosphate tribasic, calcium carbonate, and magnesium carbonate.

(ii) Binder

In another embodiment, the excipient may be a binder. Suitable binders include, but are not limited to, starches, pregelatinized starches, gelatin, polyvinylpyrrolidone, cellulose, methylcellulose, sodium carboxymethylcellulose, ethylcellulose, polyacrylamides, polyvinyloxoazolidone, polyvinylalcohols, $C_{12}$-$C_{18}$ fatty acid alcohol, polyethylene glycol, polyols, saccharides, oligosaccharides, polypeptides, oligopeptides, and combinations thereof.

(iii) Filler

In another embodiment, the excipient may be a filler. Suitable fillers include, but are not limited to, carbohydrates, inorganic compounds, and polyvinylpyrrolidone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, or sorbitol.

(iv) Buffering Agent

In still another embodiment, the excipient may be a buffering agent. Representative examples of suitable buffering agents include, but are not limited to, phosphates, carbonates, citrates, tris buffers, and buffered saline salts (e.g., Tris buffered saline or phosphate buffered saline).

(v) pH Modifier

In various embodiments, the excipient may be a pH modifier. By way of non-limiting example, the pH modifying agent may be sodium carbonate, sodium bicarbonate, sodium citrate, citric acid, or phosphoric acid.

(vi) Disintegrant

In a further embodiment, the excipient may be a disintegrant. The disintegrant may be non-effervescent or effervescent. Suitable examples of non-effervescent disintegrants include, but are not limited to, starches such as corn starch, potato starch, pregelatinized and modified starches thereof, sweeteners, clays, such as bentonite, microcrystalline cellulose, alginates, sodium starch glycolate, gums such as agar, guar, locust bean, karaya, pecitin, and tragacanth. Non-limiting examples of suitable effervescent disintegrants include sodium bicarbonate in combination with citric acid and sodium bicarbonate in combination with tartaric acid.

(vii) Dispersant

In yet another embodiment, the excipient may be a dispersant or dispersing enhancing agent. Suitable dispersants may include, but are not limited to, starch, alginic acid, polyvinylpyrrolidones, guar gum, kaolin, bentonite, purified wood cellulose, sodium starch glycolate, isoamorphous silicate, and microcrystalline cellulose.

(viii) Excipient

In another alternate embodiment, the excipient may be a preservative. Non-limiting examples of suitable preservatives include antioxidants, such as BHA, BHT, vitamin A, vitamin C, vitamin E, or retinyl palmitate, citric acid, sodium citrate; chelators such as EDTA or EGTA; and antimicrobials, such as parabens, chlorobutanol, or phenol.

(ix) Lubricant

In a further embodiment, the excipient may be a lubricant. Non-limiting examples of suitable lubricants include minerals such as talc or silica; and fats such as vegetable stearin, magnesium stearate, or stearic acid.

(x) Taste-Masking Agent

In yet another embodiment, the excipient may be a taste-masking agent. Taste-masking materials include cellulose ethers; polyethylene glycols; polyvinyl alcohol; polyvinyl alcohol and polyethylene glycol copolymers; monoglycerides or triglycerides; acrylic polymers; mixtures of acrylic polymers with cellulose ethers; cellulose acetate phthalate; and combinations thereof.

(xi) Flavoring Agent

In an alternate embodiment, the excipient may be a flavoring agent. Flavoring agents may be chosen from synthetic flavor oils and flavoring aromatics and/or natural oils, extracts from plants, leaves, flowers, fruits, and combinations thereof.

(xii) Coloring Agent

In still a further embodiment, the excipient may be a coloring agent. Suitable color additives include, but are not limited to, food, drug and cosmetic colors (FD&C), drug and cosmetic colors (D&C), or external drug and cosmetic colors (Ext. D&C).

The weight fraction of the excipient or combination of excipients in the composition may be about 99% or less, about 97% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

The agents and compositions described herein can be formulated by any conventional manner using one or more pharmaceutically acceptable carriers or excipients as described in, for example, Remington's Pharmaceutical Sciences (A. R. Gennaro, Ed.), 21st edition, ISBN: 0781746736 (2005), incorporated herein by reference in its entirety. Such formulations will contain a therapeutically effective amount of a biologically active agent described herein, which can be in purified form, together with a suitable amount of carrier so as to provide the form for proper administration to the subject.

The term "formulation" refers to preparing a drug in a form suitable for administration to a subject, such as a human. Thus, a "formulation" can include pharmaceutically acceptable excipients, including diluents or carriers.

The term "pharmaceutically acceptable" as used herein can describe substances or components that do not cause unacceptable losses of pharmacological activity or unacceptable adverse side effects. Examples of pharmaceutically acceptable ingredients can be those having monographs in United States Pharmacopeia (USP 29) and National Formulary (NF 24), United States Pharmacopeial Convention, Inc, Rockville, Maryland, 2005 ("USP/NF"), or a more recent edition, and the components listed in the continuously updated Inactive Ingredient Search online database of the FDA. Other useful components that are not described in the USP/NF, etc. may also be used.

The term "pharmaceutically acceptable excipient," as used herein, can include any and all solvents, dispersion media, coatings, antibacterial and antifungal agents, isotonic, or absorption delaying agents. The use of such media and agents for pharmaceutical active substances is well known in the art (see generally Remington's Pharmaceutical Sciences (A. R. Gennaro, Ed.), 21st edition, ISBN: 0781746736 (2005)). Except insofar as any conventional media or agent is incompatible with an active ingredient, its use in the therapeutic compositions is contemplated. Supplementary active ingredients can also be incorporated into the compositions.

A "stable" formulation or composition can refer to a composition having sufficient stability to allow storage at a convenient temperature, such as between about 0° C. and about 60° C., for a commercially reasonable period of time, such as at least about one day, at least about one week, at least about one month, at least about three months, at least about six months, at least about one year, or at least about two years.

The formulation should suit the mode of administration. The agents of use with the current disclosure can be formulated by known methods for administration to a subject using several routes which include, but are not limited to, parenteral, pulmonary, oral, topical, intradermal, intramuscular, intraperitoneal, intravenous, subcutaneous, intranasal, epidural, ophthalmic, buccal, and rectal. The individual agents may also be administered in combination with one or more additional agents or together with other biologically active or biologically inert agents. Such biologically active or inert agents may be in fluid or mechanical communication with the agent(s) or attached to the agent(s) by ionic, covalent, Van der Waals, hydrophobic, hydrophilic or other physical forces.

Controlled-release (or sustained-release) preparations may be formulated to extend the activity of the agent(s) and reduce dosage frequency. Controlled-release preparations can also be used to effect the time of onset of action or other characteristics, such as blood levels of the agent, and consequently affect the occurrence of side effects. Controlled-release preparations may be designed to initially release an amount of an agent(s) that produces the desired therapeutic effect, and gradually and continually release other amounts of the agent to maintain the level of therapeutic effect over an extended period of time. In order to maintain a near-constant level of an agent in the body, the agent can be released from the dosage form at a rate that will replace the amount of agent being metabolized or excreted from the body. The controlled-release of an agent may be stimulated by various inducers, e.g., change in pH, change in temperature, enzymes, water, or other physiological conditions or molecules.

(d) Administration (i) Dosage Forms

The composition can be formulated into various dosage forms and administered by a number of different means that will deliver a therapeutically effective amount of the active ingredient. Such compositions can be administered orally (e.g. inhalation), parenterally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, intra-articular, or intrasternal injection, or infusion techniques. Formulation of drugs is discussed in, for example, Gennaro, A. R., Remington's Pharmaceutical Sciences, Mack Publishing Co., Easton, Pa. (18th ed, 1995), and Liberman, H. A. and Lachman, L., Eds., Pharmaceutical Dosage Forms, Marcel Dekker Inc., New York, N.Y. (1980). In a specific embodiment, a composition may be a food supplement or a composition may be a cosmetic.

Solid dosage forms for oral administration include capsules, tablets, caplets, pills, powders, pellets, and granules. In such solid dosage forms, the active ingredient is ordinarily combined with one or more pharmaceutically acceptable excipients, examples of which are detailed above. Oral preparations may also be administered as aqueous suspensions, elixirs, or syrups. For these, the active ingredient may be combined with various sweetening or flavoring agents, coloring agents, and, if so desired, emulsifying and/or suspending agents, as well as diluents such as water, ethanol, glycerin, and combinations thereof. For administration by inhalation, the compounds are delivered in the form of an aerosol spray from pressured container or dispenser which contains a suitable propellant, e.g., a gas such as carbon dioxide, or a nebulizer.

For parenteral administration (including subcutaneous, intraocular, intradermal, intravenous, intramuscular, intra-articular and intraperitoneal), the preparation may be an aqueous or an oil-based solution. Aqueous solutions may include a sterile diluent such as water, saline solution, a pharmaceutically acceptable polyol such as glycerol, propylene glycol, or other synthetic solvents; an antibacterial and/or antifungal agent such as benzyl alcohol, methyl paraben, chlorobutanol, phenol, thimerosal, and the like; an antioxidant such as ascorbic acid or sodium bisulfite; a chelating agent such as etheylenediaminetetraacetic acid; a buffer such as acetate, citrate, or phosphate; and/or an agent for the adjustment of tonicity such as sodium chloride, dextrose, or a polyalcohol such as mannitol or sorbitol. The pH of the aqueous solution may be adjusted with acids or bases such as hydrochloric acid or sodium hydroxide. Oil-based solutions or suspensions may further comprise sesame, peanut, olive oil, or mineral oil. The compositions may be presented in unit-dose or multi-dose containers, for example sealed ampoules and vials, and may be stored in a freeze-dried (lyophilized) condition requiring only the addition of the sterile liquid carried, for example water for injections, immediately prior to use. Extemporaneous injection solutions and suspensions may be prepared from sterile powders, granules, and tablets.

For topical (e.g., transdermal or transmucosal) administration, penetrants appropriate to the barrier to be permeated are generally included in the preparation. Pharmaceutical compositions adapted for topical administration may be formulated as ointments, creams, suspensions, lotions, powders, solutions, pastes, gels, sprays, aerosols, or oils. In some embodiments, the pharmaceutical composition is applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base. Pharmaceutical compositions adapted for topical administration to the eye include eye drops wherein the active ingredient is dissolved or suspended in a suitable carrier, especially an aqueous solvent. Pharmaceutical compositions adapted for topical administration in the mouth include lozenges, pastilles, and mouth washes. Transmucosal administration may be accomplished through the use of nasal sprays, aerosol sprays, tablets, or suppositories, and transdermal administration may be via ointments, salves, gels, patches, or creams as generally known in the art.

In certain embodiments, a composition comprising the TIR NADase inhibitor, is encapsulated in a suitable vehicle to either aid in the delivery of the compound to target cells, to increase the stability of the composition, or to minimize potential toxicity of the composition. As will be appreciated by a skilled artisan, a variety of vehicles are suitable for delivering a composition of the present invention. Non-limiting examples of suitable structured fluid delivery systems may include nanoparticles, liposomes, microemulsions, micelles, dendrimers, and other phospholipid-containing systems. Methods of incorporating compositions into delivery vehicles are known in the art.

In one alternative embodiment, a liposome delivery vehicle may be utilized. Liposomes, depending upon the embodiment, are suitable for delivery of the TIR NADase inhibitor, in view of their structural and chemical properties. Generally speaking, liposomes are spherical vesicles with a phospholipid bilayer membrane. The lipid bilayer of a liposome may fuse with other bilayers (e.g., the cell membrane), thus delivering the contents of the liposome to cells. In this manner, the TIR NADase inhibitor may be selectively delivered to a cell by encapsulation in a liposome that fuses with the targeted cell's membrane.

Liposomes may be comprised of a variety of different types of phosolipids having varying hydrocarbon chain lengths. Phospholipids generally comprise two fatty acids linked through glycerol phosphate to one of a variety of polar groups. Suitable phospholids include phosphatidic acid (PA), phosphatidylserine (PS), phosphatidylinositol (PI), phosphatidylglycerol (PG), diphosphatidylglycerol (DPG), phosphatidylcholine (PC), and phosphatidylethanolamine (PE). The fatty acid chains comprising the phospholipids may range from about 6 to about 26 carbon atoms in length, and the lipid chains may be saturated or unsaturated. Suitable fatty acid chains include (common name presented in parentheses) n-dodecanoate (laurate), n-tretradecanoate (myristate), n-hexadecanoate (palmitate), n-octadecanoate (stearate), n-eicosanoate (arachidate), n-docosanoate (behenate), n-tetracosanoate (lignocerate), cis-9-hexadecenoate (palmitoleate), cis-9-octadecanoate (oleate), cis,cis-9,12-octadecandienoate (linoleate), all cis-9, 12, 15-octadecatrienoate (linolenate), and all cis-5,8,11,14-eicosatetraenoate (arachidonate). The two fatty acid chains of a phospholipid may be identical or different. Acceptable phospholipids include dioleoyl PS, dioleoyl PC, distearoyl PS, distearoyl PC, dimyristoyl PS, dimyristoyl PC, dipalmitoyl PG, stearoyl, oleoyl PS, palmitoyl, linolenyl PS, and the like.

The phospholipids may come from any natural source, and, as such, may comprise a mixture of phospholipids. For example, egg yolk is rich in PC, PG, and PE, soy beans contains PC, PE, PI, and PA, and animal brain or spinal cord is enriched in PS. Phospholipids may come from synthetic sources too. Mixtures of phospholipids having a varied ratio of individual phospholipids may be used. Mixtures of different phospholipids may result in liposome compositions having advantageous activity or stability of activity properties. The above mentioned phospholipids may be mixed, in optimal ratios with cationic lipids, such as N-(1-(2,3-dioleolyoxy)propyl)-N,N,N-trimethyl ammonium chloride, 1,1'-dioctadecyl-3,3,3',3'-tetramethylindocarbocyanine perchloarate, 3,3'-deheptyloxacarbocyanine iodide, 1,1'-dedodecyl-3,3,3',3'-tetramethylindocarbocyanine perchloarate, 1,1'-dioleyl-3,3,3',3'-tetramethylindo carbocyanine methanesulfonate, N-4-(delinoleylaminostyryl)-N-methylpyridinium iodide, or 1,1,-dilinoleyl-3,3,3',3'-tetramethylindocarbocyanine perchloarate.

Liposomes may optionally comprise sphingolipids, in which spingosine is the structural counterpart of glycerol and one of the one fatty acids of a phosphoglyceride, or cholesterol, a major component of animal cell membranes. Liposomes may optionally contain pegylated lipids, which are lipids covalently linked to polymers of polyethylene glycol (PEG). PEGs may range in size from about 500 to about 10,000 daltons.

Liposomes may further comprise a suitable solvent. The solvent may be an organic solvent or an inorganic solvent. Suitable solvents include, but are not limited to, dimethylsulfoxide (DMSO), methylpyrrolidone, N-methylpyrrolidone, acetonitrile, alcohols, dimethylformamide, tetrahydrofuran, or combinations thereof.

Liposomes carrying a TIR NADase inhibitor, may be prepared by any known method of preparing liposomes for drug delivery, such as, for example, detailed in U.S. Pat. Nos. 4,241,046; 4,394,448; 4,529,561; 4,755,388; 4,828,837; 4,925,661; 4,954,345; 4,957,735; 5,043,164; 5,064,655; 5,077,211; and 5,264,618, the disclosures of which are hereby incorporated by reference in their entirety. For example, liposomes may be prepared by sonicating lipids in an aqueous solution, solvent injection, lipid hydration, reverse evaporation, or freeze drying by repeated freezing and thawing. In a preferred embodiment the liposomes are formed by sonication. The liposomes may be multilamellar, which have many layers like an onion, or unilamellar. The liposomes may be large or small. Continued high-shear sonication tends to form smaller unilamellar lipsomes.

As would be apparent to one of ordinary skill, all of the parameters that govern liposome formation may be varied. These parameters include, but are not limited to, temperature, pH, concentration of a TIR NADase inhibitor, concentration and composition of lipid, concentration of multivalent cations, rate of mixing, presence of and concentration of solvent.

In another embodiment, a composition of the invention may be delivered to a cell as a microemulsion. Microemulsions are generally clear, thermodynamically stable solutions comprising an aqueous solution, a surfactant, and "oil." The "oil" in this case, is the supercritical fluid phase. The surfactant rests at the oil-water interface. Any of a variety of surfactants are suitable for use in microemulsion formulations including those described herein or otherwise known in the art. The aqueous microdomains suitable for use in the invention generally will have characteristic structural dimensions from about 5 nm to about 100 nm. Aggregates of this size are poor scatterers of visible light and hence, these solutions are optically clear. As will be appreciated by a skilled artisan, microemulsions can and will have a multitude of different microscopic structures including sphere, rod, or disc shaped aggregates. In one embodiment, the structure may be micelles, which are the simplest microemulsion structures that are generally spherical or cylindrical objects. Micelles are like drops of oil in water, and reverse micelles are like drops of water in oil. In an alternative embodiment, the microemulsion structure is the lamellae. It comprises consecutive layers of water and oil separated by layers of surfactant. The "oil" of microemulsions optimally comprises phospholipids. Any of the phospholipids detailed above for liposomes are suitable for embodiments directed to microemulsions. The TIR NADase inhibitor may be encapsulated in a microemulsion by any method generally known in the art.

In yet another embodiment, a TIR NADase inhibitor, may be delivered in a dendritic macromolecule, or a dendrimer. Generally speaking, a dendrimer is a branched tree-like molecule, in which each branch is an interlinked chain of molecules that divides into two new branches (molecules) after a certain length. This branching continues until the branches (molecules) become so densely packed that the canopy forms a globe. Generally, the properties of dendrimers are determined by the functional groups at their surface. For example, hydrophilic end groups, such as carboxyl groups, would typically make a water-soluble dendrimer. Alternatively, phospholipids may be incorporated in the surface of a dendrimer to facilitate absorption across the skin. Any of the phospholipids detailed for use in liposome embodiments are suitable for use in dendrimer embodiments. Any method generally known in the art may be utilized to make dendrimers and to encapsulate compositions of the invention therein. For example, dendrimers may be produced by an iterative sequence of reaction steps, in which each additional iteration leads to a higher order dendrimer. Consequently, they have a regular, highly branched 3D structure, with nearly uniform size and shape. Furthermore, the final size of a dendrimer is typically controlled by the number of iterative steps used during synthesis. A variety of dendrimer sizes are suitable for use in the invention. Generally, the size of dendrimers may range from about 1 nm to about 100 nm.

Generally, a safe and effective amount of a TIR NADase inhibitor is, for example, that amount that would cause the desired therapeutic effect in a subject while minimizing undesired side effects. In various embodiments, an effective amount of a TIR NADase inhibitor described herein can substantially inhibit TIR NADase activity and treat associated diseases. In some embodiments, an effective amount is an amount capable of increasing the concentration of NAD+ in a biological sample compared to that of a control or decreasing the concentration of one or more of ADPR, cADPR or nicotinamide relative to a control and as such represent a therapeutic option for treatment of diseases and disorders associated with TIR NADase activity. In some embodiments, compositions provided herein contain and/or deliver an amount of a TIR NADase inhibitor that is effective to measurably inhibit such TIR NADase activity and/or treat, and/or decrease the infectivity, morbidity, and rate of mortality associated with an infection or infectious disease or disorder in or on a subject when administered to the subject in an appropriate dosing regimen.

When used in the treatments described herein, a therapeutically effective amount of a TIR NADase inhibitor can be employed in pure form or, where such forms exist, in pharmaceutically acceptable salt form and with or without a pharmaceutically acceptable excipient. For example, the compounds of the present disclosure can be administered, at a reasonable benefit/risk ratio applicable to any medical treatment, in a sufficient amount to modulate diseases and disorders, for example, microbial infections associated with TIR NADase activity.

The amount of a composition described herein that can be combined with a pharmaceutically acceptable carrier to produce a single dosage form will vary depending upon the host treated and the particular mode of administration. It will be appreciated by those skilled in the art that the unit content of agent contained in an individual dose of each dosage form need not in itself constitute a therapeutically effective amount, as the necessary therapeutically effective amount could be reached by administration of a number of individual doses.

Toxicity and therapeutic efficacy of compositions described herein can be determined by standard pharmaceutical procedures in cell cultures or experimental animals for determining the LD50 (the dose lethal to 50% of the population) and the ED50, (the dose therapeutically effective in 50% of the population). The dose ratio between toxic and therapeutic effects is the therapeutic index that can be expressed as the ratio LD50/ED50, where larger therapeutic indices are generally understood in the art to be optimal.

The specific therapeutically effective dose level for any particular subject will depend upon a variety of factors including the disorder being treated and the severity of the disorder; activity of the specific compound employed; the specific composition employed; the age, body weight, general health, sex and diet of the subject; the time of administration; the route of administration; the rate of excretion of the composition employed; the duration of the treatment; drugs used in combination or coincidental with the specific compound employed; and like factors well known in the medical arts (see e.g., Koda-Kimble et al. (2004) Applied Therapeutics: The Clinical Use of Drugs, Lippincott Williams & Wilkins, ISBN 0781748453; Winter (2003) Basic Clinical Pharmacokinetics, 4th ed., Lippincott Williams & Wilkins, ISBN 0781741475; Sharqel (2004) Applied Biopharmaceutics & Pharmacokinetics, McGraw-Hill/Appleton & Lange, ISBN 0071375503). For example, it is well within the skill of the art to start doses of the composition at levels lower than those required to achieve the desired therapeutic effect and to gradually increase the dosage until the desired effect is achieved. If desired, the effective daily dose may be divided into multiple doses for purposes of administration. Consequently, single dose compositions may contain such amounts or submultiples thereof to make up the daily dose. It will be understood, however, that the total daily usage of the compounds and compositions of the present disclosure will be decided by an attending physician within the scope of sound medical judgment.

Again, each of the states, diseases, disorders, and conditions, described herein, as well as others, can benefit from compositions and methods described herein. Generally, treating a state, disease, disorder, or condition includes preventing or delaying the appearance of clinical symptoms in a mammal that may be afflicted with or predisposed to the state, disease, disorder, or condition but does not yet experience or display clinical or subclinical symptoms thereof. Treating can also include inhibiting the state, disease, disorder, or condition, e.g., arresting or reducing the development of the disease or at least one clinical or subclinical symptom thereof. Furthermore, treating can include relieving the disease, e.g., causing regression of the state, disease, disorder, or condition or at least one of its clinical or subclinical symptoms. A benefit to a subject to be treated can be either statistically significant or at least perceptible to the subject or to a physician.

Administration of a TIR NADase inhibitor can occur as a single event or over a time course of treatment. For example, a TIR NADase inhibitor can be administered daily, weekly, bi-weekly, or monthly. For treatment of acute conditions, the time course of treatment will usually be at least several days. Certain conditions could extend treatment from several days to several weeks. For example, treatment could extend over one week, two weeks, or three weeks. For more chronic conditions, treatment could extend from several weeks to several months or even a year or more.

The present disclosure encompasses pharmaceutical compositions comprising a TIR NADase inhibitor as disclosed above, so as to facilitate administration and promote stability of the active agent. For example, a TIR NADase inhibitor of this disclosure may be admixed with at least one pharmaceutically acceptable carrier or excipient resulting in a pharmaceutical composition which is capably and effectively administered (given) to a living subject, such as to a suitable subject (i.e. "a subject in need of treatment" or "a subject in need thereof"). For the purposes of the aspects and embodiments of the invention, the subject may be a human or any other animal. In particular embodiments, the subject is selected from the group consisting of primate, equine, ovine, caprine, leporine, avian, feline, rodent, or canine. Methods of preparing and administering a TIR NADase inhibitor disclosed herein to a subject in need thereof are well known to or are readily determined by those skilled in the art. The route of administration of a TIR NADase inhibitor can be, for example, peripheral, oral, parenteral, by inhalation or topical.

In some embodiments, the compounds as presented herein are administered as part of a pharmaceutically acceptable composition. In some embodiments, the compounds as presented herein are administered orally. In some embodiments, the compounds as presented herein are administered in a range of 0.01-100 mg/kg body weight of the patient.

(II) Methods

The present disclosure encompasses a method of measurably inhibiting TIR NADase activity of a TIR domain containing polypeptide. The present disclosure provides methods of inhibiting TIR NADase activity use in vitro, in vivo, in situ or ex vivo. Generally, the method comprises administration of an effective amount of a TIR NADase inhibitor, so as to down-regulate the NADase activity of a TIR domain containing polypeptide. In some embodiments, the TIR NADase inhibitor is administered to a biological sample. The term "biological sample", as used herein, includes, without limitation, tissues, cells, cell cultures or extracts thereof; biopsied material obtained from a subject or extracts thereof; and blood, saliva, urine, feces, semen, tears, or other body fluids or extracts thereof. Inhibition of enzymes in a biological sample is useful for a variety of purposes that are known to one of skill in the art. Examples of such purposes include, but are not limited to biological assays, gene expression studies, and biological target identification. In some embodiments, the TIR NADase inhibitor is administered to a subject in need thereof. Suitable compositions comprising a TIR NADase inhibitor are disclosed herein, for instance those described in Section I.

As used herein, the term "measurably inhibit" refers to a measurable change in TIR NADase activity between a sample comprising a TIR domain containing polypeptide contacted with a TIR NADase inhibitor, and an equivalent sample contacted with a control composition (e.g. a carrier) or in the absence of a TIR NADase inhibitor. In some embodiments, a TIR NADase inhibitor "measurably inhibits" TIR NADase activity by at least 1-fold, 2-fold, 3-fold, 4-fold, or greater as compared to the control. In some embodiments, a TIR NADase inhibitor "measurably inhibits" TIR NADase activity by at least 1%, 2%, 3%, 4%, 5%, 6%, 7%, 8%, 9%, 10%, 15%, 20%, 25%, 50%, 75% or more as compared to control.

As used herein, the term "TIR NADase" refers to a polypeptide comprising a TIR domain and has NADase enzymatic activity. Unless otherwise indicated, "polypeptide" shall include a protein, protein domain, or peptide, and any fragment thereof. The Toll/Il-1 Receptor (TIR) domain was first characterized due to homology between the intracellular regions of the mammalian IL-1 receptor (IL-1R) and the *Drosophila* protein Toll. Subsequently, six Toll-Like Receptors (TLRs) have been identified in *Drosophila* and more than twenty TLRs and IL-1Rs have been recognized in humans. Several adaptor proteins containing TIR domains have also been described. In general, the TIR domain consists of three 'boxes' of conserved residues set in a core sequence ranging from about 135 to about 160 amino acids. Intervening residues may vary, as sequence conservation between domains is only 20-30%. Two interfaces are responsible for mediating TIR domain interactions, which include receptor/adaptor oligomerization and association between receptors and adaptors. TLR and IL-1R signaling pathways are key mediators of the innate immune response to bacteria and fungi in both *Drosophila* and mammals. TIR domain interactions between receptors and adaptors play a key role in activating conserved cellular signal transduction pathways in response to bacterial LPS, microbial and viral pathogens, cytokines and growth factors. Homotypic and heterotypic interactions are thought to mediate receptor signaling. Activation involves liberation of NF-κB resulting in lymphocyte activation, immunoglobulin isotype switching and expression of cytokines and their receptors.

The crystal structure of TIR domains from human TLR1 and TLR2 reveal a central five-stranded parallel β-sheet surrounded by a total of five helices on both sides. Conserved residues are located in the hydrophobic core and large insertions or deletions can be present in several loop regions of different TIR domains. The BB loop, containing three highly conserved residues, protrudes from a large conserved surface patch and is thought to mediate heterodimeric interactions with TIR domain-containing adaptor proteins.

TIR domain containing polypeptides can be identified using techniques standard in the art, for example, those described in the Examples below. Unless otherwise specified a "TIR-domain containing polypeptide" or "TIR NADase" refers to a full length wild-type polypeptide which optionally includes a tag. In some embodiments, a mutant or fragment of a TIR NADase is a TIR-domain containing mutant or fragment having NADase activity. In some embodiments, the full length, mutant or fragment of a TIR NADase can consist of or consist essentially of a full length, mutant or fragment TIR NADase from any species encoding a TIR domain containing polypeptide. In some embodiments, the TIR NADase is a full length, mutant or fragment is from a prokaryotic organism. In some embodiments, a full length, mutant or fragment is a viral TIR NADase. In some embodiments, the full length, mutant or fragment of a TIR NADase is from a mammal. In some embodiments, the full length, mutant or fragment mammalian TIR NADase is from a human, with the provision that the TIR NADase is not SARM1. In some embodiments a full length, mutant or fragment is an insect TIR NADase. In some embodiments, the TIR NADase may comprise the amino acid sequence as set forth in SEQ ID NO: 1, 2, 3, 4, 5, 6, 7, 8, 9, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, or 44. In another aspect, the TIR NADase may comprise an amino acid sequence with 80% identity, 81% identity, 82% identity, 83% identity, 84% identity, 85% identity, 86% identity, 87% identity, 88% identity, 89% identity, 90% identity, 91% identity, 92% identity, 93% identity, 94% identity, 95% identity, 96% identity, 97% identity, 98% identity, 99% identity to SEQ ID NO: 1, 2, 3, 4, 5, 6, 7, 8, 9, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, or 43.

According to an aspect of the present invention, the TIR NADase may comprise the amino acid sequence set forth in SEQ ID NO: 1, 2, 3, 4, 5, 6, 7, 8, 9, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43 or their functional homologues, including derivatives and fragments. Homologues of a TIR NADase can be obtained, for example, by mutation of a TIR NADase-encoding nucleotide sequence, respectively, and expression from the mutated sequence and/or by use or derivation from related gene sequences. Alternatively, homologues can be obtained, for example by identifying gene sequences homologous to TIR domain containing polypeptides by screening databases containing either protein sequences or nucleotide sequences encoding proteins, for example using homology-based search algorithms such as those commonly known and referred to as BLAST, FASTA, and Smith-Waterman. A local sequence alignment program, e.g., BLAST, can be used to search a database of sequences to find similar sequences, and the summary Expectation value (E-value) used to measure the sequence base similarity. As a protein hit with the best E-value for a particular organism may not necessarily be an ortholog or the only ortholog, a reciprocal query is used in the present invention to filter hit sequences with significant E-values for ortholog identification. The reciprocal query entails search of the significant hits against a database of amino acid sequences from the base organism that are similar to the sequence of the query protein. A hit is a likely ortholog, when the reciprocal query's best hit is the query protein itself or a protein encoded by a duplicated gene after speciation. An acceptable level of homology over the whole sequence is at least about 20%, for example 30% homology, 40% homology, 50% homology, 60% homology, 70% homology, 80% homology, 90% homology or greater. The homology of a functional fragment of a TIR NADase may be at least 10% homology. A "homologous" amino acid sequence, as used herein, refers to an amino acid sequence that differs from a reference amino acid sequence, only by one or more (e.g., 1, 2, 3, 4 or 5) conservative amino acid substitutions, or by one or more (e.g., 1, 2, 3, 4 or 5) non-conservative amino acid substitutions, deletions, or additions located at positions at which they do not adversely affect the activity of the polypeptide. For example, the NADase activity of a TIR domain containing polypeptide can be measured. In some embodiments, such a sequence is at least 75%, 80%, 85%, 90%, or 95% or greater identical to a reference amino acid sequence.

Homologous amino acid sequences include peptide sequences that are identical or substantially identical to a reference amino acid sequence. By "amino acid sequence substantially identical" is meant a sequence that is at least 90%, preferably 95%, more preferably 97%, and most preferably 99% identical to an amino acid sequence of reference and that preferably differs from the sequence of reference, if at all, by a majority of conservative amino acid substitutions.

Conservative amino acid substitutions typically include substitutions among amino acids of the same class. These classes include, for example, (a) amino acids having uncharged polar side chains, such as asparagine, glutamine, serine, threonine, and tyrosine; (b) amino acids having basic side chains, such as lysine, arginine, and histidine; (c) amino acids having acidic side chains, such as aspartic acid and glutamic acid; and (d) amino acids having nonpolar side chains, such as glycine, alanine, valine, leucine, isoleucine, proline, phenylalanine, methionine, tryptophan, and cysteine.

Another aspect of the present disclosure provides a method of inhibiting microbial NADase activity in a biological sample or in a subject in need thereof. In general, the method comprises administering a therapeutically effective amount of a composition comprising an inhibitor of TIR NADase activity for treatment of infections or infectious disorders. The inhibitors of TIR NADase activity as described herein are useful to decreasing the infectivity, morbidity, and rate of mortality associated with a variety of pathogenic organisms. According to one embodiment, the invention relates to a method of inhibiting microbial TIR NADase activity in a biological sample comprising the step of contacting said biological sample with a TIR NADase inhibitor as described herein. As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

In an aspect, the TIR NADase inhibitors are administered to treat a microbial infection. As used herein, "infection" and, equivalently, "infectious disease" shall refer to a disease arising from the presence of a foreign microorganism in and/or on the body of a subject. A foreign microorganism may be a virus, a bacterium, a fungus, or a parasite. Examples of infectious viruses include: Retroviridae (e.g., human immunodeficiency viruses, such as HIV-1 (also referred to as HTLV-III, LAV or HTLV-III/LAV, or HIV-III; and other isolates, such as HIV-LP; Picornaviridae (e.g., polio viruses, hepatitis A virus; enteroviruses, human coxsackie viruses, rhinoviruses, echoviruses); Calciviridae (e.g., strains that cause gastroenteritis); Togaviridae (e.g., equine encephalitis viruses, rubella viruses); Flaviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bungaviridae (e.g., Hantaan viruses, bunga viruses, phleboviruses and Nairo viruses); Arena viridae (hemorrhagic fever viruses); Reoviridae (e.g., reoviruses, orbiviurses and rotaviruses); Birnaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes viruses); Poxviridae (variola viruses, vaccinia viruses, pox viruses); and Iridoviridae (e.g., African swine fever virus); and unclassified viruses (e.g., the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e., Hepatitis C); Norwalk and related viruses, and astroviruses).

Examples of infectious bacteria include: *Actinomyces israelii, Bacillus anthracis, Bacteroides* spp., *Borrelia burgdorferi, Chlamydia trachomatis, Clostridium perfringens, Clostridium tetani, Corynebacterium diphtheriae, Corynebacterium* spp., *Enterobacter aerogenes, Enterococcus* sp., *Erysipelothrix rhusiopathiae, Escherichia coli, Fusobacterium nucleatum, Haemophilus influenzae, Helicobacter pyloris, Klebsiella pneumoniae, Legionella pneumophilia, Leptospira, Listeria monocytogenes, Mycobacteria* spp. (e.g., *M. tuberculosis, M. avium, M. intracellulare, M. kansasii, M. gordonae*), *Neisseria gonorrhoeae, Neisseria meningitidis, Pasteurella multocida*, pathogenic *Campylobacter* sp., *Staphylococcus aureus, Streptobacillus moniliformis, Streptococcus* (anaerobic spp.), *Streptococcus* (viridans group), *Streptococcus agalactiae* (Group B *Streptococcus*), *Streptococcus bovis, Streptococcus faecalis, Streptococcus pneumoniae, Streptococcus pyogenes* (Group A *Streptococcus*), *Treponema pallidum*, and *Treponema pertenue*.

Examples of infectious fungi include: *Candida albicans, Cryptococcus neoformans, Histoplasma capsulatum, Coccidioides immitis*, and *Blastomyces dermatitidis*.

Other infectious organisms (i.e., protists) include *Plasmodium* spp. such as *Plasmodium falciparum, Plasmodium malariae, Plasmodium ovale*, and *Plasmodium vivax*, and *Toxoplasma gondii*. Blood-borne and/or tissue parasites include *Plasmodium* spp., *Babesia microti, Babesia divergens, Leishmania tropica, Leishmania* spp., *Leishmania braziliensis, Leishmania donovani, Trypanosoma gambiense* and *Trypanosoma rhodesiense* (African sleeping sickness), *Trypanosoma cruzi* (Chagas' disease), and *Toxoplasma gondii*.

The foregoing list of viruses, bacteria, fungi and other infectious microorganisms is understood to be representative and not limiting. Other medically relevant microorganisms have been described extensively in the literature, e.g., see C. G. A Thomas, Medical Microbiology, Bailliere Tindall, Great Britain 1983, the entire contents of which is hereby incorporated by reference.

In another aspect, the present teachings include a host cell, that harbors a nucleic acid or product thereof that encodes an exogenous full length, mutant or fragment TIR NADase. As used herein, when referring to nucleic acids or a product thereof, the term "exogenous" refers to any nucleic acid sequence or polypeptide that is not naturally expressed in the particular cell where expression is desired. As used herein, the term "host cell" refers to any eukaryotic or prokaryotic cell (e.g., bacterial cells such as *E. coli*, yeast cells, mammalian cells, avian cells, amphibian cells, fish cells and insect cells). Methods of transforming cells are well known in the art.

The nucleic acid can be DNA or RNA. In one embodiment the DNA can be present in a vector. The nucleic acid sequences which encode the reporter molecule of the invention can be operatively linked to expression control sequences. "Operatively linked" refers to a juxtaposition wherein the components so described are in a relationship permitting them to function in their intended manner. An expression control sequence operatively linked to a coding sequence is achieved under conditions compatible with the expression control sequences. As used herein, the phrase "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a protein-encoding gene, splicing signals for introns, and maintenance of the correct reading frame of that gene to permit proper translation of the mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

By "promoter" is meant minimal sequence sufficient to direct transcription. Also included in the invention are those promoter elements which are sufficient to render promoter-dependent gene expression controllable for cell-type specific expression, tissue-specific expression, or expression inducible by external signals or agents; such elements may be located in the 5' or 3' regions of the gene. Both constitutive and inducible promoters, are included in the invention (see e.g., Bitter et al., Methods in Enzymology 153:516-544, 1987). For example, when cloning in bacterial systems, inducible promoters such as pL of bacteriophage γ, plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the nucleic acid sequences of the invention.

In some embodiments, the nucleic acid sequences encoding a TIR domain containing polypeptide of the invention may be inserted into a recombinant expression vector. The term "recombinant expression vector" refers to a plasmid, virus or other vehicle known in the art that has been manipulated by insertion or incorporation of the nucleic acid sequences encoding the fusion peptides of the invention. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg, et al., Gene 56:125, 1987), the pMSXND expression vector for expression in mammalian cells (Lee and Nathans, J. Biol. Chem. 263:3521, 1988), baculovirus-derived vectors for expression in insect cells, cauliflower mosaic virus, CaMV; or tobacco mosaic virus, TMV. The nucleic acid sequences encoding a TIR domain containing polypeptide as described herein can also include a localization sequence to direct the indicator to particular cellular sites by fusion to appropriate organellar targeting signals or localized host proteins. A polynucleotide encoding a localization sequence, or signal sequence, can be used as a repressor and thus can be ligated or fused at the 5' terminus of a polynucleotide encoding the reporter polypeptide such that the signal peptide is located at the amino terminal end of the resulting fusion polynucleotide/polypeptide. The construction of expression vectors and the expression of genes in transfected cells involve the use of molecular cloning techniques also well known in the art. Sambrook et al., Molecular Cloning—A Laboratory Manual, Cold Spring Harbor Laboratory, Cold Spring Harbor, N.Y., 1989, and Current Protocols in Molecular Biology, M. Ausubel et al., eds., (Current Protocols, a joint venture between Greene Publishing Associates, Inc. and John Wiley & Sons, Inc., most recent Supplement). These methods include in vitro recombinant DNA techniques, synthetic techniques and in vivo recombination/genetic recombination. (See, for example, the techniques described in Maniatis, et al., Molecular Cloning A Laboratory Manual, Cold Spring Harbor Laboratory, N.Y., 1989).

Depending on the vector utilized, any of a number of suitable transcription and translation elements, including constitutive and inducible promoters, transcription enhancer elements, transcription terminators, etc. may be used in the expression vector (see, e.g., Bitter, et al., Methods in Enzymology 153:516-544, 1987). These elements are well known to one of skill in the art.

By "transformation" is meant a permanent genetic change induce in a cell following incorporation of new DNA (i.e., DNA exogenous to the cell). Where the cell is a mammalian cell, the permanent genetic change is generally achieved by introduction of the DNA into the genome of the cell.

Transformation of a host cell with recombinant DNA may be carried out by conventional techniques well known to those skilled in the art. Where the host is prokaryotic, such as E. coli, competent cells which are capable of DNA uptake can be prepared from cells harvested after exponential growth phase and subsequently treated by the CaCl2) method by procedures well known in the art. Alternatively, MgCl2 or RbCl can be used. Transformation can also be performed after forming a protoplast of the host cell or by electroporation.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be co-transfected with DNA sequences encoding the reporter molecules of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (Eukaryotic Viral Vectors, Cold Spring Harbor Laboratory, Gluzman ed., 1982). Preferably, a eukaryotic host is utilized as the host cell as described herein. The eukaryotic cell may be a yeast cell (e.g., Saccharomyces cerevisiae), or may be a mammalian cell. In one embodiment, the mammalian cell is a human cell.

Eukaryotic systems, and preferably mammalian expression systems, allow for proper post-translational modifications of expressed mammalian proteins to occur. Eukaryotic cells which possess the cellular machinery for proper processing of the primary transcript, glycosylation, phosphorylation, and, advantageously secretion of the gene product should be used as host cells for the expression of fluorescent indicator. Such host cell lines may include but are not limited to NRK1-HEK293T, CHO, VERO, BHK, HeLa, COS, MDCK, Jurkat, HEK-293, and W138. In one embodiment, the eukaryotic cell is a human cell.

Mammalian cell systems which utilize recombinant viruses or viral elements to direct expression may be engineered. For example, when using adenovirus expression vectors, the nucleic acid sequences encoding a TIR domain containing polypeptide of the invention may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the fluorescent indicator in infected hosts (e.g., see Logan & Shenk, Proc. Natl. Acad. Sci. USA, 81:3655-3659, 1984). Alternatively, the vaccinia virus 7.5K promoter may be used. (e.g., see, Mackett, et al., Proc. Natl. Acad. Sci. USA, 79:7415-7419, 1982; Mackett, et al., J. Virol. 49:857-864, 1984; Panicali, et al., Proc. Natl. Acad. Sci. USA 79:4927-4931, 1982). Also contemplated are vectors based on bovine papilloma virus which have the ability to replicate as extrachromosomal elements (Sarver, et al., Mol. Cell.

Biol. 1:486, 1981). Shortly after entry of this DNA into mouse cells, the plasmid replicates to about 100 to 200 copies per cell. Transcription of the inserted cDNA does not require integration of the plasmid into the host's chromosome, thereby yielding a high level of expression. These vectors can be used for stable expression by including a selectable marker in the plasmid, such as the neo gene. Alternatively, the retroviral genome can be modified for use as a vector capable of introducing and directing the expression of the fluorescent indicator gene in host cells (Cone & Mulligan, Proc. Natl. Acad. Sci. USA, 81:6349-6353, 1984). High level expression may also be achieved using inducible promoters, including, but not limited to, the metallothionine IIA promoter and heat shock promoters.

For long-term, high-yield production of recombinant proteins, stable expression may be preferred. Rather than using expression vectors which contain viral origins of replication, host cells can be transformed with the cDNA encoding a TIR domain containing polypeptide of the invention controlled by appropriate expression control elements (e.g., promoter, enhancer, sequences, transcription terminators, polyadenylation sites, etc.), and a selectable marker. The selectable marker in the recombinant plasmid confers resistance to the selection and allows cells to stably integrate the plasmid into their chromosomes and grow to form foci which in turn can be cloned and expanded into cell lines. For example, following the introduction of foreign DNA, engineered cells may be allowed to grow for 1-2 days in an enriched media, and then are switched to a selective media. A number of selection systems may be used, including but not limited to the herpes simplex virus thymidine kinase (Wigler, et al., Cell, 11:223, 1977), hypoxanthine-guanine phosphoribosyltransferase (Szybalska & Szybalski, Proc. Natl. Acad. Sci. USA, 48:2026, 1962), and adenine phosphoribosyltransferase (Lowy, et al., Cell, 22:817, 1980) genes can be employed in tk-, hgprt- or aprt-cells respectively. Also, antimetabolite resistance can be used as the basis of selection for dhfr, which confers resistance to methotrexate (Wigler, et al., Proc. Natl. Acad. Sci. USA, 77:3567, 1980; O'Hare, et al., Proc. Natl. Acad Sci. USA, 8:1527, 1981); gpt, which confers resistance to mycophenolic acid (Mulligan & Berg, Proc. Natl. Acad. Sci. USA, 78:2072, 1981; neo, which confers resistance to the aminoglycoside G-418 (Colberre-Garapin, et al, J. Mol. Biol 150:1, 1981); and hygro, which confers resistance to hygromycin (Santerre, et al., Gene 30: 147, 1984) genes. Recently, additional selectable genes have been described, namely trpB, which allows cells to utilize indole in place of tryptophan; hisD, which allows cells to utilize histinol in place of histidine (Hartman & Mulligan, Proc. Natl. Acad. Sci. USA 85:8047, 1988); and ODC (ornithine decarboxylase) which confers resistance to the ornithine decarboxylase inhibitor, 2-(difluoromethyl)-DL-ornithine, DFMO (McConlogue L., In: Current Communications in Molecular Biology, Cold Spring Harbor Laboratory, ed., 1987).

A TIR domain containing polypeptide as described herein can be produced by expression of nucleic acid encoding the TIR domain containing polypeptide in prokaryotes. These include but are not limited to microorganisms such as bacteria transformed with recombinant bacteriophage DNA, plasmid DNA or cosmid DNA expression vectors encoding a TIR domain containing polypeptide. The constructs can also be expressed in E. coli in large scale. Purification from bacteria is simplified when the sequences include tags for one-step purification by nickel-chelate chromatography. The construct can also contain a tag to simplify isolation of the fluorescent indicator. For example, a polyhistidine tag of, e.g., six histidine residues, can be incorporated at the amino terminal end of the fluorescent protein. The polyhistidine tag allows convenient isolation of the protein in a single step by nickel-chelate chromatography. The TIR domain containing polypeptide of the invention can also be engineered to contain a cleavage site to aid in protein recovery.

Techniques for the isolation and purification of either microbially or eukaryotically expressed polypeptides of the invention may be by any conventional means such as, for example, preparative chromatographic separations and immunological separations such as those involving the use of monoclonal or polyclonal antibodies or antigen.

In yet another aspect, the present invention provides methods to determine if a TIR-domain containing polypeptide is a TIR NADase, Such methods comprise: a) expressing an exogenous TIR-domain containing polypeptide or TIR-domain containing fragment thereof in a host cell, and; b) quantifying one or more of $NAD^+$, ADPR, cADPR or nicotinamide in said TIR-domain expressing host cell or lysate thereof. In some embodiments, provided methods can further comprise c) identifying the TIR-domain containing polypeptide as a TIR NADase when the amount of $NAD^+$ is decreased in said host cell and/or when the amount of ADPR, cADPR, nicotinamide or combinations thereof are increased in said host cell. In alternative embodiments, provided methods can further comprise d) identifying the TIR-domain containing polypeptide as a TIR NADase when the amount of $NAD^+$ is decreased and/or ADPR cADPR, nicotinamide or combinations thereof are increased compared to a control host cell which does not express the TIR-domain containing polypeptide. In some embodiments, the host cell lysate is a NRK1-HEK293T cell. In some embodiments, one or more of $NAD^+$, ADPR, nicotinamide or any combination thereof is quantified by any available analytical method, such as, for example, performing an HPLC analysis, a chemiluminescence assay, a liquid chromatography-mass spectroscopy analysis or a combination thereof.

In some embodiments, the present invention provides methods to determine if a TIR-domain containing polypeptide is a TIR NADase, Such methods comprise: a) expressing an exogenous TIR-domain containing polypeptide or TIR-domain containing fragment thereof in a cell-free system, and; b) determining if the TIR-domain polypeptide cleaves $NAD^+$ by measuring $NAD^+$, nicotinamide, ADPR, and cADPR. In some embodiments, provided methods can further comprise d) identifying the TIR-domain containing polypeptide as a TIR NADase when the amount of $NAD^+$ is decreased in said cell-free system and/or when the amount of ADPR, cADPR, nicotinamide or combinations thereof are increased in said cell-free system. In alternative embodiments, provided methods can further comprise d) identifying the TIR-domain containing polypeptide as a TIR NADase when the amount of $NAD^+$ is decreased and/or ADPR cADPR, nicotinamide or combinations thereof are increased compared to a cell-free system which does not express the TIR-domain containing polypeptide. In some embodiments, one or more of NAD+, ADPR, nicotinamide or any combination thereof is quantified by any available analytical method, such as, for example, performing an HPLC analysis, a chemiluminescence assay, a liquid chromatography-mass spectroscopy analysis or a combination thereof.

In some embodiments, the present invention provides methods of identifying if a TIR-domain containing polypeptide is a TIR NADase, which comprises: a) providing a mixture comprising i) $NAD^+$ and; ii) a solid support to which is bound a polypeptide consisting of a TIR-domain containing polypeptide or fragment thereof; b) quantifying the $NAD^+$ in the mixture; and c) identifying the TIR-domain containing polypeptide as a TIR NADase if the concentration of $NAD^+$ is less than that of a control. By way of non-limiting example, the solid support to which a TIR domain containing polypeptide is bound may be beads, plastic, nitrocellulose, indium, tin, cadmium, silica, poly (ethylene glycol)methacrylate graft polymer, or variations thereof.

In some embodiments, the present invention provides methods of identifying a TIR NADase inhibitor. Such methods comprise: a) providing a mixture comprising i) a full length, mutant or fragment of a TIR NADase, ii) $NAD^+$, and iii) a candidate inhibitor, wherein the mutant or fragment optionally has constitutive NADase activity; b) incubating the mixture; and c) quantifying $NAD^+$, ADPR, nicotinamide or any combination thereof in the mixture after the incubating. In some embodiments, provided methods can further comprise d) determining the molar ratio of $NAD^+$/ADPR; and e) identifying a candidate inhibitor compound as an NADase inhibitor if the molar ratio of $NAD^+$/ADPR is greater than that of a control mixture that does not contain the candidate inhibitor. In some embodiments, one or more of $NAD^+$, ADPR, nicotinamide or any combination thereof is quantified by any available analytical method, such as, for example, performing an HPLC analysis, a chemiluminescence assay, a liquid chromatography-mass spectroscopy analysis or a combination thereof. In some embodiments, the mixture comprises a cell lysate comprising a full length, mutant or fragment of a TIR NADase. In some embodiments, the cell lysate is a lysate of mammalian cells comprising, consisting of, or consisting essentially of a full length, mutant or fragment of a TIR NADase polypeptide that has NADase activity. In some embodiments, the cell lysate is from a host cell comprising, consisting of, or consisting essentially of a full length, mutant or fragment of a TIR NADase that has NADase activity. In some embodiments, the cell lysate is a lysate of NRK1-HEK293T cells comprising, consisting of, or consisting essentially of a full length, mutant or fragment of a TIR NADase that has NADase activity. In some embodiments, the mixture can comprise a purified TIR NADase polypeptide. In some embodiments, the NRK1-HEK293T cells is treated with nicotinamide riboside (NR), which can be useful for maintaining high $NAD^+$ levels and increasing cell viability in the presence of constitutively active TIR NADase molecules. In some embodiments, an inhibitor is identified as an NADase inhibitor if the molar ratio of $NAD^+$ to ADPR is greater than 4:1. In some embodiments, the candidate inhibitor compound is identified as a NADase inhibitor if the molar ratio of $NAD^+$ to ADPR is greater than 1:1, 2:1, 3:1, 4:1, 5:1, 6:1, 7:1, 8:1, 9:1 or 10:1.

In some embodiments, a method of identifying a TIR NADase inhibitor comprises: a) providing a mixture comprising i) a full length mutant or fragment of a TIR NADase, ii) $NAD^+$ and iii) a candidate inhibitor, wherein the mutant or fragment optionally has constitutive NADase activity; b) incubating the mixture; c) quantifying $NAD^+$ in the mixture after the incubating; and d) identifying the candidate inhibitor compound as an NADase inhibitor if the amount of $NAD^+$ is greater than that of a control mixture that does not contain the candidate inhibitor. In some embodiments, the quantifying $NAD^+$ in the mixture comprises, consists of, or consists essentially of performing a chemiluminescence assay. In some embodiments, the quantifying $NAD^+$ in the mixture comprises, consists of, or consists essentially of performing an HPLC analysis. In some embodiments, the mixture can comprise a purified TIR containing fragment. In some embodiments, the mixture comprises a cell lysate comprising the mutant or fragment of a TIR NADase. In some embodiments, the cell lysate is a lysate of NRK1-HEK293T cells comprising the mutant or fragment of a TIR NADase. In some embodiments, the NRK1-HEK293T cells comprising the mutant or fragment of a TIR NADase is treated with NR.

In some embodiments, a TIR-domain containing polypeptide or TIR NADase comprises, consists of, or consists essentially of a) a full length, mutant or fragment of a TIR-domain containing polypeptide or TIR NADase, wherein the mutant or fragment optionally has constitutive NADase activity; and b) at least one tag. In non-limiting examples the at least one tag is a StrepTag, a polyhistidine tag, an antibody epitope (e.g., derived from myc), and the like and a combination thereof. In some embodiments, the polypeptide further includes at least one tag, such as an N-terminal tag. In some embodiments, the N-terminal tag is a tandem tag. In some embodiments, the at least one tag is a C-terminal tag. In some embodiments, the C-terminal tag is a polyhistidine tag. In some embodiments, the bead is a histidine tag purification bead. In some embodiments, the at least one tag is at least two tags. In some embodiments, the at least two tags is an N-terminal tag and a C-terminal tag. In some embodiments, the N-terminal tag is a tandem StrepTag and the C-terminal tag is a polyhistidine tag. In some embodiments, the polypeptide is immobilized on a solid support. In some embodiments, vectors include a plasmid or virus comprising a sequence encoding a polypeptide described herein.

In some embodiments, the present invention provides methods of identifying a TIR NADase inhibitor, which comprises: a) providing a mixture comprising $NAD^+$ and a solid support to which is bound a polypeptide consisting of a full length, mutant or fragment of a TIR NADase optionally having constitutive NADase activity; b) adding a candidate inhibitor to the mixture; c) incubating the mixture; d) quantifying the $NAD^+$ in the mixture; and e) identifying the candidate inhibitor compound as a TIR NADase inhibitor if the concentration of $NAD^+$ is greater than that of a control. In some embodiments, provided methods include stopping NADase activity (if any) in the mixture after the incubating. In some embodiments, the quantifying $NAD^+$ comprises performing an HPLC-based analysis. In some embodiments, the quantifying $NAD^+$ and ADPR comprises performing an LC/MS-based analysis. In some embodiments, a candidate inhibitor compound is identified as a TIR NADase inhibitor if the molar ratio of NAD to ADPR is greater than 4:1. In some embodiments, a candidate inhibitor compound is identified as a TIR NADase inhibitor if the molar ratio of NAD to ADPR is greater than 1:1, 2:1, 3:1, 4:1, 5:1, 6:1, 7:1, 8:1, 9:1, or 10:1.

In some embodiments, the present invention provides a full length TIR NADase polypeptide mutant or fragment. In some embodiments, a TIR NADase polypeptide, or mutant or fragment thereof may be bound to a solid support such as a bead. In some embodiments, the TIR NADase polypeptide, or mutant or fragment thereof bound to a solid support comprises, consists of, or consists essentially of a TIR domain, or a TIR NADase polypeptide deleted for an autoinhibitory domain. In some embodiments, the TIR NADase polypeptide mutant or fragment further comprises, consists of, or consists essentially of a tag. In some embodiments, a TIR NADase polypeptide mutant or fragment having NADase activity comprises, consists of, or consists essentially of a TIR NADase mutant or fragment bound to a solid support via a protein tag.

In some embodiments, a method of identifying a TIR NADase inhibitor comprises: a) providing a mixture comprising at least one cultured cell; b) adding a candidate TIR NADase inhibitor to the mixture; c) adding a labeled NAM to the mixture; d) incubating the mixture; and e) quantifying the amount of labeled and unlabeled NAD+ in the mixture. In some embodiments, provided methods can further comprise f) calculating the net rate of $NAD^+$ consumption, for example by calculating the % decrease of unlabeled over total $NAD^+$ (e.g., light NAD over total (light plus heavy) NAD+) over time. In some embodiments, the calculation is expressed, for example, as %/hr. In some embodiments, the labeled NAM is deuterium labeled ("heavy") NAM. In some embodiments, the labeled NAM is d4-NAM. In some embodiments, the quantifying of labeled and unlabeled $NAD^+$ is performed using analytical methods such as LC-MS/MS. In some embodiments, the at least one cultured cell is a mammalian cell.

In each of the above embodiments, the candidate TIR NADase inhibitor may be chosen from a library of compounds. Suitable compounds include small molecules, pharmaceutically active compounds (i.e., drugs), natural products, carbohydrates, lipid molecules, amino acid derivatives, peptides, peptide mimetics, nucleic acids, antisense oligonucleotides, microRNAs, and so forth. In exemplary embodiments, the compounds are from a library of small molecules. In general, a small molecule is defined as a molecule having a molecular weight of less than about 1000 daltons (Da). In other embodiments, the plurality of compounds may comprise larger molecules that are cell permeable.

Libraries of small molecules are available through repositories or commercial sources, and means for generating libraries of small molecules are well known in the art. In some embodiments, the compounds to be screened may comprise a tag. Suitable tags include biotin, fluorophores, dyes, fluorocarbon tags, click chemistry tags, affinity tags, and the like. The presence of the tag may permit isolation of a complex comprising the compound and a cellular target with which the compound interacts.

The compounds to be screened generally will be dissolved in a suitable solvent (such as, e.g., DMSO or ethanol) and contacted with a sample comprising a TIR domain containing polypeptide. The candidate compounds may be distributed to the wells of a multi-well system using multichannel pipette systems or robotic liquid handling systems. Initially, the samples comprising a TIR domain containing polypeptide will be contacted with a single concentration of each compound. Additionally, compounds that affect the NADase activity of the TIR domain containing polypeptide can be rescreened at several different concentrations to determine the half maximal effective concentration (EC50). For statistical purposes, contact with a compound of interest will be performed in at least duplicate or triplicate.

During each screening procedure, a small percentage of samples comprising the TIR domain containing polypeptide can serve as untreated controls. That is, the untreated samples will not be contacted with any compounds of interest but rather will be contacted only with the solvent used to dissolve the compounds of interest, as appropriate.

(III) Kits

Also provided are kits. Such kits can include an agent or composition described herein and, in certain embodiments, instructions for administration. Such kits can facilitate performance of the methods described herein. When supplied as a kit, the different components of the composition can be packaged in separate containers and admixed immediately before use. Components include, but are not limited to compositions and pharmaceutical formulations comprising a TIR NADase inhibitor, isolated nucleic acids encoding a TIR NADase or cells exogenously expressing a TIR NADase polypeptide, as described herein. Such packaging of the components separately can, if desired, be presented in a pack or dispenser device which may contain one or more unit dosage forms containing the composition. The pack may, for example, comprise metal or plastic foil such as a blister pack. Such packaging of the components separately can also, in certain instances, permit long-term storage without losing activity of the components.

Kits may also include reagents in separate containers such as, for example, sterile water or saline to be added to a lyophilized active component packaged separately. For example, sealed glass ampules may contain a lyophilized component and in a separate ampule, sterile water, sterile saline or sterile each of which has been packaged under a neutral non-reacting gas, such as nitrogen. Ampules may consist of any suitable material, such as glass, organic polymers, such as polycarbonate, polystyrene, ceramic, metal or any other material typically employed to hold reagents. Other examples of suitable containers include bottles that may be fabricated from similar substances as ampules, and envelopes that may consist of foil-lined interiors, such as aluminum or an alloy. Other containers include test tubes, vials, flasks, bottles, syringes, and the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, and the like.

In certain embodiments, kits can be supplied with instructional materials. Instructions may be printed on paper or other substrate, and/or may be supplied as an electronic-readable medium, such as a floppy disc, mini-CD-ROM, CD-ROM, DVD-ROM, Zip disc, videotape, audio tape, and the like. Detailed instructions may not be physically associated with the kit; instead, a user may be directed to an Internet web site specified by the manufacturer or distributor of the kit.

Compositions and methods described herein utilizing molecular biology protocols can be according to a variety of standard techniques known to the art (see, e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754; Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Definitions

When introducing elements of the present disclosure or the preferred aspects(s) thereof, the articles "a," "an," "the,"

and "said" are intended to mean that there are one or more of the elements. The terms "comprising," "including," and "having" are intended to be inclusive and mean that there may be additional elements other than the listed elements.

As used herein, the following definitions shall apply unless otherwise indicated. For purposes of this invention, the chemical elements are identified in accordance with the Periodic Table of the Elements, CAS version, and the Handbook of Chemistry and Physics, 75th Ed. 1994. Additionally, general principles of organic chemistry are described in "Organic Chemistry," Thomas Sorrell, University Science Books, Sausalito: 1999, and "March's Advanced Organic Chemistry," 5th Ed., Smith, M. B. and March, J., eds. John Wiley & Sons, New York: 2001, the entire contents of which are hereby incorporated by reference.

The term "mmol", as used herein, is intended to mean millimole. The term "equiv", as used herein, is intended to mean equivalent. The term "mL", as used herein, is intended to mean milliliter. The term "g", as used herein, is intended to mean gram. The term "kg", as used herein, is intended to mean kilogram. The term "µg", as used herein, is intended to mean micrograms. The term "h", as used herein, is intended to mean hour. The term "min", as used herein, is intended to mean minute. The term "M", as used herein, is intended to mean molar. The term "µL", as used herein, is intended to mean microliter. The term "µM", as used herein, is intended to mean micromolar. The term "nM", as used herein, is intended to mean nanomolar. The term "N", as used herein, is intended to mean normal. The term "amu", as used herein, is intended to mean atomic mass unit. The term "° C.", as used herein, is intended to mean degree Celsius. The term "wt/wt", as used herein, is intended to mean weight/weight. The term "v/v", as used herein, is intended to mean volume/volume. The term "MS", as used herein, is intended to mean mass spectroscopy. The term "HPLC", as used herein, is intended to mean high performance liquid chromatograph. The term "RT", as used herein, is intended to mean room temperature. The term "e.g.", as used herein, is intended to mean example. The term "N/A", as used herein, is intended to mean not tested.

Specific embodiments disclosed herein may be further limited in the claims using "consisting of" or "consisting essentially of" language, rather than "comprising". When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

As various changes could be made in the above-described reporter molecules and methods without departing from the scope of the invention, it is intended that all matter contained in the above description and in the examples given below, shall be interpreted as illustrative and not in a limiting sense.

EXAMPLES

The following examples are included to demonstrate various embodiments of the present disclosure. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Materials and Methods for Examples 1

Recombinant DNA and Endogenous $NAD^+$ Measurements in Host E. coli.

Double tagged (N-terminal tandem StrepTag and C-terminal 6×HisTag) bacterial or archaea TIRs (see sequence in FIG. 5) were cloned into a pET30a+ plasmid. These constructs as well as non-recombinant pET30a+ were transformed into Shuffle T7 Express Competent E-coli (New England BioLabs). Single colonies were grown overnight and the next day, cultures were diluted in LB media, grown at 30° C. until they reached A600 of approximately 0.4-0.8, when IPTG (0.1 mM final concentration) was added to induce protein expression. The cultures were then harvested approximately 2 hours later. The cultures were normalized to A600 of approximately 0.5±0.05 and the pellet from 500 µl of culture suspension was lysed by adding 200□□L 0.5M perchloric acid (HClO4). Samples were then placed on ice for at least 10 minutes, centrifuged, and supernatant collected. 180 □L of supernatant was then added to approximately 67 □L of 3M K2CO3. Samples were placed on ice for at least 10 minutes, and centrifuged. NAD+ metabolites were then measured by HPLC as described below.

Cell-free protein transcription and translation.

In vitro cell-free protein transcription and translation was performed using the PURExpress In Vitro Protein Synthesis Kit (New England BioLabs Catalog #E6800S). For a total reaction volume of about 25 µL, the reaction was assembled in the following order: 10 µL of Solution A, 7.5 µL of Solution B, 3 µL of RNase inhibitor (40 U/uL), water, and 0.5-1.0 µg of pET30a+ non-recombinant/recombinant DNA. The reaction was incubated at 37° C. for 2.5 hours and stopped by placing on ice. Typically, two 25 µL reactions were pooled together for Tandem Affinity purification of proteins, which is described below.

Mammalian Cell Culture and $NAD^+$ quantification.

HEK293T cells were maintained in 10% FBS in DMEM, supplemented with penicillin/streptomycin and glutamine, and passaged by suspending in 0.05% trypsin. For $NAD^+$ measurements in mammalian cells, HEK293T cells were seeded in 12-well dishes (approximately 2.5×105 cells per well) and transiently transfected the following day with 500 ng of the indicated plasmid using polyethylenimine (3:1 ratio to plasmid DNA). Twenty-four hours later, cells were washed in cold phosphate buffered saline and $NAD^+$ extracted using perchloric acid method. $NAD^+$ was measured after separation by HPLC.

Identification of prokaryotic TIR domains and database search.

Candidate pathogenic bacterial TIRs were selected from the published literature where at least seven bacterial TIR domain proteins have been reported to promote virulence (Waldhuber et al., 2016). A. baumannii was included since carbapenem-resistant A. baumannii is classified under 'Priority 1' of the 2017 WHO Priority Pathogens List for R&D of New Antibiotics. P. dentrificans TIR domain is not known to promote virulence but it was one of the first bacterial TIR domains where the crystal structure was available (Waldhuber et al., 2016). The archaeal TIR domains were identified by searching the non-redundant protein database in proteinBLAST, and selecting Archaea (taxaid: 2157) under Organism. The blastp (protein-protein blast) algorithm was utilized and the search was performed using the sequence of the bacterial TIR domains TirS-TIR and TcpC-TIR (see sequence in FIG. 5). Both *M. olleyae* and *T. archaeon* ranked as the top 2 hits with highest max score, and lowest e-value in the search using TirS-TIR, and *T. archaeon* ranked the highest in the max score and identity, and lowest e-value in the search using TcpC-TIR. The TIR domain from *Actinoplanes* was identified from bioinformatics analyses establishing a phylogenetic relationship between SARM1-TIR and other TIR domains.

HPLC metabolite measurement.

Supernatant (90 µL) containing the extracted metabolites was mixed with 0.5M Potassium Phosphate buffer (10 µL), and metabolites were analyzed by HPLC (Nexera X2) with Kinetex (100×3 mm, 2.6 µm; Phenomenex) column. Internal standards for $NAD^+$, Nicotinamide (Nam), ADP Ribose (ADPR), and cyclic ADPR were used to generate standard curves for quantification of the respective compounds. The levels for each compound in each experimental sample were normalized to the 0 min time point that was analyzed concurrently.

Native Protein Purification.

Cell-free synthesized proteins were first purified by Strep Tag affinity methods where proteins were incubated in binding buffer (50 mM Sodium Phosphate buffer pH 7.6, 300 mM Sodium Chloride, 0.01% Tween-20) and 20 µL MagStrep (Strep-Tactin) type 3 XT beads suspension (IBA Lifesciences) for 30 min. Proteins were then eluted from MagStrep type 3 XT beads with approximately 25 mM biotin (Sigma, B4501) for 25 min. The purified proteins were normally purified further by incubating the eluted protein with 10 µL $Co^{2+}$ Dynabead suspension (ThermoFisher) for 30 min to bind TIR proteins via the His tag. The beads were then washed at least two times with binding buffer and resuspended in 100 µL of binding buffer for downstream applications.

NADase assay and metabolite extraction.

For purified TIR domains, typically, 10 µL of cobalt beads laden with purified protein were incubated with 5 µM $NAD^+$ and reaction buffer (92.4 mM NaCl and 0.64×PBS), for a total reaction volume of 50 µL. Reactions were carried out at room temperature (25° C.) for the indicated amount of time. For TirS-FL, 20 µL of biotin eluted protein was incubated with 5 µM $NAD^+$, under the same buffer and temperature conditions. Reaction was stopped by addition of 1M of perchloric acid ($HClO_4$) and placing the tube on ice for at least 10 min. Neutralization was performed with 3M $K_2CO_3$. Samples were placed on ice for 10 min, and then separated by centrifugation. $NAD^+$ metabolites were quantified by HPLC (see HPLC metabolite measurement). For LC-MS analysis, the extraction was performed using 50% Methanol in distilled water, and chloroform extraction (see LC-MS metabolite measurement for further details).

LC-MS metabolite measurement.

Samples were prepared by mixing the reactions with 50% methanol in distilled water. The samples were placed on ice, centrifuged, soluble metabolites in the supernatant were extracted with chloroform, and the aqueous phase was lyophilized and stored at −20° C. until LC-MS analysis. For LC-MS, the metabolite samples were reconstituted with 5 mM ammonium formate, centrifuged 12,000×g for 10 min, and the cleared supernatant was applied to the LC-MS for metabolite identification and quantification. Liquid chromatography was performed by HPLC system (1290; Agilent) with Atlantis T3 (2.1×150 mm, 3 µm; Waters) column. Samples (10 µl) were injected at a flow rate of 0.15 ml/min with 5 mM ammonium formate for mobile phase A and 100% methanol for mobile phase B and metabolites were eluted with gradients of 2-6 min, 0-20% B; 6-8 min, 20-50% B; 8-10 min 50% B; 10-15 min, 50-0% B. The metabolites were detected with Triple Quad mass spectrometer (6460; Agilent) under positive ESI multiple reaction monitoring (MRM). Metabolites were quantified by MassHunter quantitative analysis tool (Agilent) with standard curves. Standard curves for each compound were generated by analyzing $NAD^+$, cADPR, ADPR, and Nam reconstituted in 5 mM ammonium formate.

SYPRO Ruby Gel Staining.

Purified proteins were boiled in Laemmli buffer for 5-10 min and separated on a 4-12% Bis-Tris Plus gel. After electrophoresis, the gel was fixed in 50% Methanol/7% acetic acid for 30 min×2, then incubated overnight in SYPRO Ruby Protein Gel stain (Thermo Fisher). The next day, the gel was washed with 10% methanol/7% acetic acid solution for 30 min, rinsed in distilled water for 5 minutes×2, and stained proteins were visualized with a UV transilluminator.

Enzyme kinetics studies.

$V_{max}$, and $K_m$ were determined from the initial reaction velocity or reaction velocity in the first 60 s of product (ADPR) formation, and fitting the data to the Michaelis-Menten equation using nonlinear curve fit in GraphPad Prism 7. Data are presented as Mean±SEM from two independents biological samples and a total of four independent reaction measurements.

Structural Modeling of bacterial TIR domains.

SWISS-Model (Arnold et al., 2006) was used to generate structural models of bacterial TIR domains. The crystal structure of MilB CMP hydrolase (PDB 4JEM) was used as the template. The modeled bacterial TIR domain and MilB crystal structures were visualized and superimposed with Chimera (www.rbvi.ucsf.edu/chimera). tan—modeled bacterial TIR; cyan—MilB CMP hydrolase; yellow—cytidine-5'-monophosphate (ligand for MilB).

HH Pred Protein Identification.

TirS-TIR, TcpC-TIR, and TcpA-TIR were analyzed for structural homologs using HH Pred. (Alva et al., 2016). Only known nucleotide enzymes with an E-value lower than 0.1 and a probability above 95% are shown in Table 1.

TABLE 1

Nucleotide hydrolase/transferase enzymes identified via HHPred. TirS-TIR, TcpC-TIR, and TcpA-TIR were each used as a query sequence in HHPred to identify candidate enzymes.

| PDB | Protein Identification | Probability | E-value |
|---|---|---|---|
| | TirS-TIR | | |
| 4JEM_B | CMP/hydroxymethyl CMP hydrolase; CMP N-glycosidase, Hydrolase; HET: C5P; 1.553A {*Streptomyces rimofaciens*} | 97.83 | 0.000013 |

TABLE 1-continued

Nucleotide hydrolase/transferase enzymes identified via HHPred. TirS-TIR, TcpC-TIR, and TcpA-TIR were each used as a query sequence in HHPred to identify candidate enzymes.

| PDB | Protein Identification | Probability | E-value |
| --- | --- | --- | --- |
| 4JEM_A | CMP/hydroxymethyl CMP hydrolase; CMP N-glycosidase, Hydrolase; HET: C5P; 1.553A {*Streptomyces rimofaciens*} | 97.83 | 0.000013 |
| 2KLH_B | c-Myc-responsive protein Rcl; Protein, GMP, N-Glycosidase, Nucleus, Phosphoprotein; HET: 5GP; NMR {*Rattus norvegicus*} | 97.73 | 0.000012 |
| 4JEN_B | Putative uncharacterized protein; CMP N-glycosidase, bacimethrin biosynthesis, Hydrolase; HET: PO4; 3.0A {*Clostridium botulinum* A} | 97.51 | 0.000084 |
| 4JEN_C | Putative uncharacterized protein; CMP N-glycosidase, bacimethrin biosynthesis, Hydrolase; HET: PO4; 3.0A {*Clostridium botulinum* A} | 97.51 | 0.000084 |
| 4HX9_C | Nucleoside deoxyribosyltransferase (E.C.2.4.2.6); Non-natural and design enzyme; HET: SO4, PG4; 2.68A {*Lactobacillus leichmannii*} | 96.73 | 0.0034 |
| 1S2D_B | purine trans deoxyribosylase (E.C.2.4.2.6); ribosylate intermediate, PTD, AraA, TRANSFERASE; HET: ADE; 2.1A {*Lactobacillus helveticus*} SCOP: c.23.14.1 | 96.62 | 0.0029 |
| 4P5E_B | 2'-deoxynucleoside 5'-phosphate N-hydrolase 1 (E.C.3.2.2.-); RCL, DNPH1, Inhibitor, Rossmann Fold; HET: N6P; 1.35A {*Homo sapiens*} | 96.57 | 0.002 |
| 1F8Y_B | NUCLEOSIDE 2-DEOXYRIBOSYLTRANSFERASE; active site, alpha/beta protein, biocatalyst; HET: 5MD; 2.4A {*Lactobacillus leichmannii*} SCOP: c.23.14.1 | 96.55 | 0.0064 |
| 2F62_B | Nucleoside 2-deoxyribosyltransferase (E.C.2.4.2.6); SGPP, Structural GENOMICS, PSI, PROTEIN; HET: GOL, 12M, SO4; 1.5A {*Trypanosoma brucei*} SCOP: c.23.14.1 | 96.02 | 0.0096 |
| 2F2T_B | Nucleoside 2-deoxyribosyltransferase (E.C.2.4.2.6); SGPP, Structural GENOMICS, PSI, PROTEIN; HET: GOL, 5IQ, SO4; 1.7A {*Trypanosoma brucei*} SCOP: c.23.14.1 | 96.02 | 0.0096 |

TcpC-TIR

| PDB | Protein Identification | Probability | E-value |
| --- | --- | --- | --- |
| 4JEN_B | Putative uncharacterized protein; CMP N-glycosidase, bacimethrin biosynthesis, Hydrolase; HET: PO4; 3.0A {*Clostridium botulinum* A} | 97.38 | 0.0002 |
| 4JEN_C | Putative uncharacterized protein; CMP N-glycosidase, bacimethrin biosynthesis, Hydrolase; HET: PO4; 3.0A {*Clostridium botulinum* A} | 97.38 | 0.0002 |
| 4JEM_B | CMP/hydroxymethyl CMP hydrolase; CMP N-glycosidase, Hydrolase; HET: C5P; 1.553A {*Streptomyces rimofaciens*} | 97.34 | 0.00024 |
| 4JEM_A | CMP/hydroxymethyl CMP hydrolase; CMP N-glycosidase, Hydrolase; HET: C5P; 1.553A {*Streptomyces rimofaciens*} | 97.34 | 0.00024 |
| 2KLH_B | c-Myc-responsive protein Rcl; Protein, GMP, N-Glycosidase, Nucleus, Phosphoprotein; HET: 5GP; NMR {*Rattus norvegicus*} | 97.18 | 0.00039 |
| 4HX9_C | Nucleoside deoxyribosyltransferase (E.C.2.4.2.6); Non-natural and design enzyme; HET: SO4, PG4; 2.68A {*Lactobacillus leichmannii*} | 96.29 | 0.012 |
| 1S2D_B | purine trans deoxyribosylase (E.C.2.4.2.6); ribosylate intermediate, PTD, AraA, TRANSFERASE; HET: ADE; 2.1A {*Lactobacillus helveticus*} SCOP: c.23.14.1 | 96.21 | 0.014 |
| 2F2T_B | Nucleoside 2-deoxyribosyltransferase (E.C.2.4.2.6); SGPP, Structural GENOMICS, PSI, PROTEIN; HET: GOL, 5IQ, SO4; 1.7A {*Trypanosoma brucei*} SCOP: c.23.14.1 | 96.05 | 0.024 |
| 2F62_B | Nucleoside 2-deoxyribosyltransferase (E.C.2.4.2.6); SGPP, Structural GENOMICS, PSI, PROTEIN; HET: GOL, 12M, SO4; 1.5A {*Trypanosoma brucei*} SCOP: c.23.14.1 | 96.05 | 0.024 |
| 4P5E_B | 2'-deoxynucleoside 5'-phosphate N-hydrolase 1 (E.C.3.2.2.-); RCL, DNPH1, Inhibitor, Rossmann Fold; HET: N6P; 1.35A {*Homo sapiens*} | 96 | 0.017 |
| 1F8Y_B | NUCLEOSIDE 2-DEOXYRIBOSYLTRANSFERASE; active site, alpha/beta protein, biocatalyst; HET: 5MD; 2.4A {*Lactobacillus leichmannii*} SCOP: c.23.14.1 | 95.79 | 0.053 |

TcpA-TIR

| PDB | Protein Identification | Probability | E-value |
| --- | --- | --- | --- |
| 4JEM_A | CMP/hydroxymethyl CMP hydrolase; CMP N-glycosidase, Hydrolase; HET: C5P; 1.553A {*Streptomyces rimofaciens*} | 97.97 | 0.000003 |

TABLE 1-continued

Nucleotide hydrolase/transferase enzymes identified via HHPred. TirS-TIR, TcpC-TIR, and TcpA-TIR were each used as a query sequence in HHPred to identify candidate enzymes.

| PDB | Protein Identification | Probability | E-value |
|---|---|---|---|
| 4JEM_B | CMP/hydroxymethyl CMP hydrolase; CMP N-glycosidase, Hydrolase; HET: C5P; 1.553A {*Streptomyces rimofaciens*} | 97.97 | 0.000003 |
| 4JEN_B | Putative uncharacterized protein; CMP N-glycosidase, bacimethrin biosynthesis, Hydrolase; HET: PO4; 3.0A {*Clostridium botulinum* A} | 97.86 | 0.000025 |
| 4JEN_C | Putative uncharacterized protein; CMP N-glycosidase, bacimethrin biosynthesis, Hydrolase; HET: PO4; 3.0A {*Clostridium botulinum* A} | 97.86 | 0.000025 |
| 2KLH_B | c-Myc-responsive protein Rcl; Protein, GMP, N-Glycosidase, Nucleus, Phosphoprotein; HET: 5GP; NMR {*Rattus norvegicus*} | 97.6 | 0.00004 |
| 4HX9_C | Nucleoside deoxyribosyltransferase (E.C.2.4.2.6); Non-natural and design enzyme; HET: SO4, PG4; 2.68A {*Lactobacillus leichmannii*} | 97.16 | 0.00056 |
| 1S2D_B | purine trans deoxyribosylase (E.C.2.4.2.6); ribosylate intermediate, PTD, AraA, TRANSFERASE; HET: ADE; 2.1A {*Lactobacillus helveticus*} SCOP: c.23.14.1 | 97.02 | 0.0006 |
| 1F8Y_B | NUCLEOSIDE 2-DEOXYRIBOSYLTRANSFERASE; active site, alpha/beta protein, biocatalyst; HET: 5MD; 2.4A {*Lactobacillus leichmannii*} SCOP: c.23.14.1 | 96.92 | 0.002 |
| 2F2T_B | Nucleoside 2-deoxyribosyltransferase (E.C.2.4.2.6); SGPP, Structural GENOMICS, PSI, PROTEIN; HET: GOL, 5IQ, SO4; 1.7A {*Trypanosoma brucei*} SCOP: c.23.14.1 | 96.35 | 0.0048 |
| 2F62_B | Nucleoside 2-deoxyribosyltransferase (E.C.2.4.2.6); SGPP, Structural GENOMICS, PSI, PROTEIN; HET: GOL, 12M, SO4; 1.5A {*Trypanosoma brucei*} SCOP: c.23.14.1 | 96.35 | 0.0048 |
| 4P5E_B | 2'-deoxynucleoside 5'-phosphate N-hydrolase 1 (E.C.3.2.2.-); RCL, DNPH1, Inhibitor, Rossmann Fold; HET: N6P; 1.35A {*Homo sapiens*} | 96.28 | 0.012 |

Quantification and Statistical analysis.

Number of n is indicated in each figure legend. Unpaired two-tailed t-tests were used for individual comparisons with an assumption of equal variance between groups. All error bars represent SEM. Other data analyses were done with Graph Pad Prism 7, Microsoft Excel, Adobe Illustrator and Photoshop.

Example 1

This example illustrates a diverse set of prokaryotic TIR domains are capable of regulating levels of the central metabolic regulator NAD+ and thereby elucidate a previously unappreciated function of TIR domains separate from the scaffolding functions in TLR signaling and opening a new therapeutic window. Furthermore, this example illustrates a TIR domain assay for NADase activity.

Identification of prokaryotic TIR domains that induce $NAD^+$ loss in host *E. coli*.

Figure 1B:
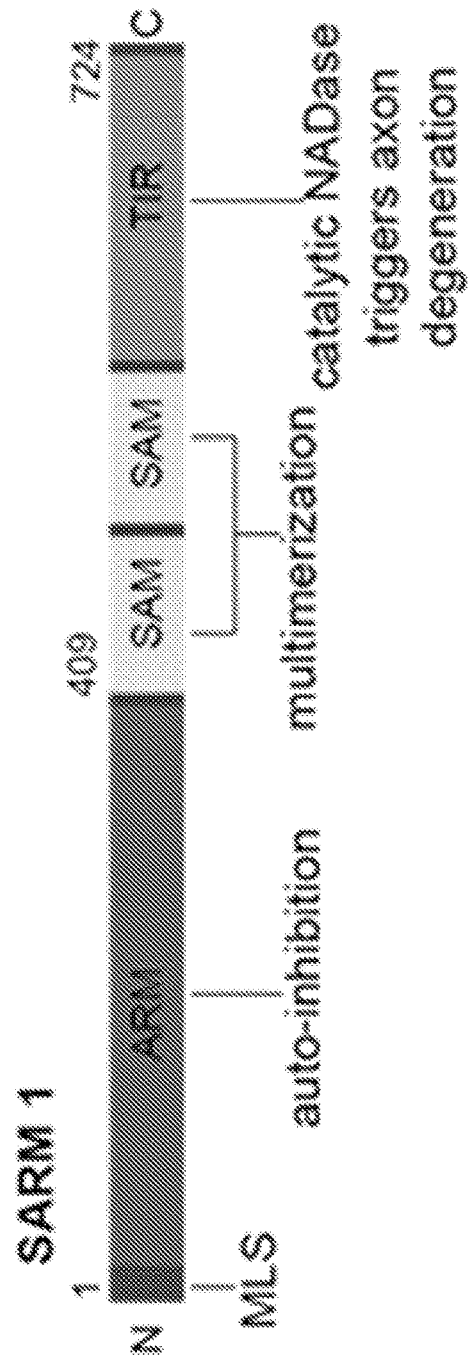
Figure 1C:
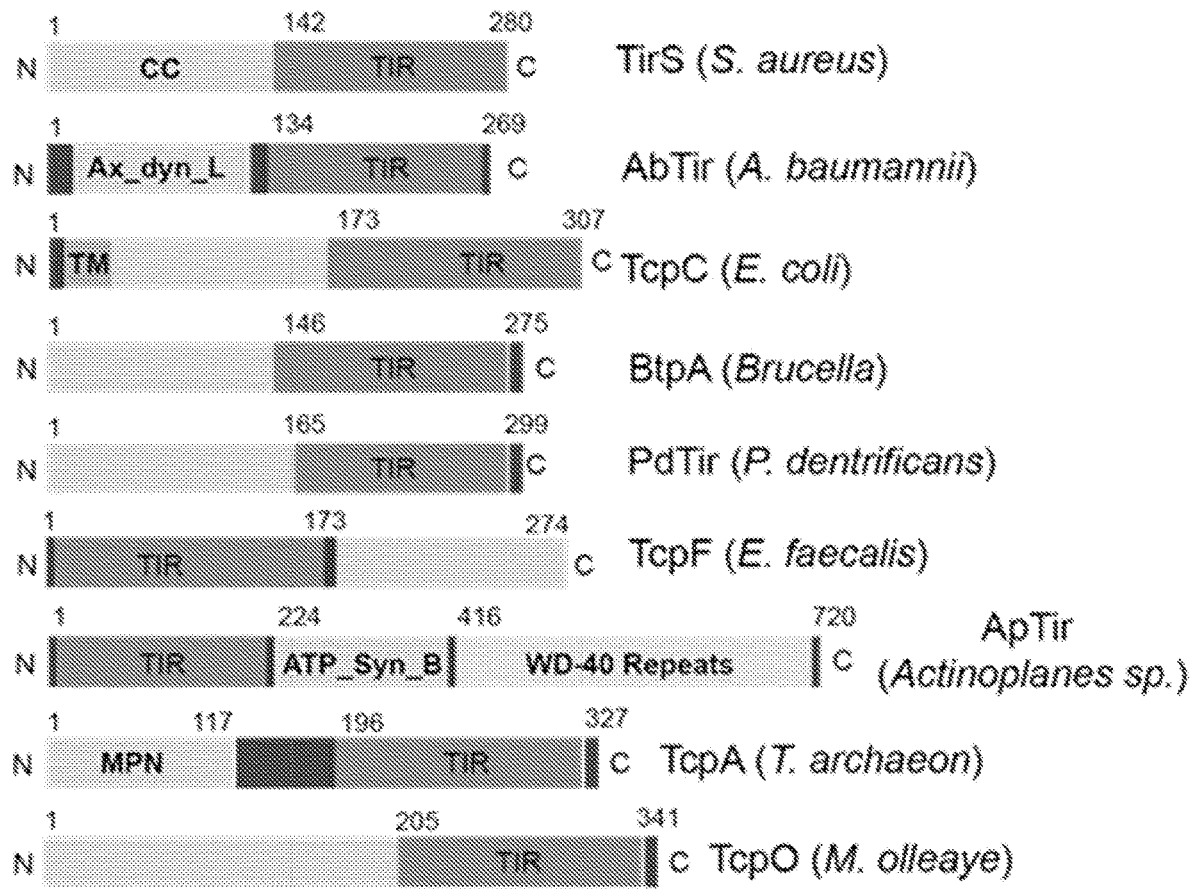
Figure 1D:
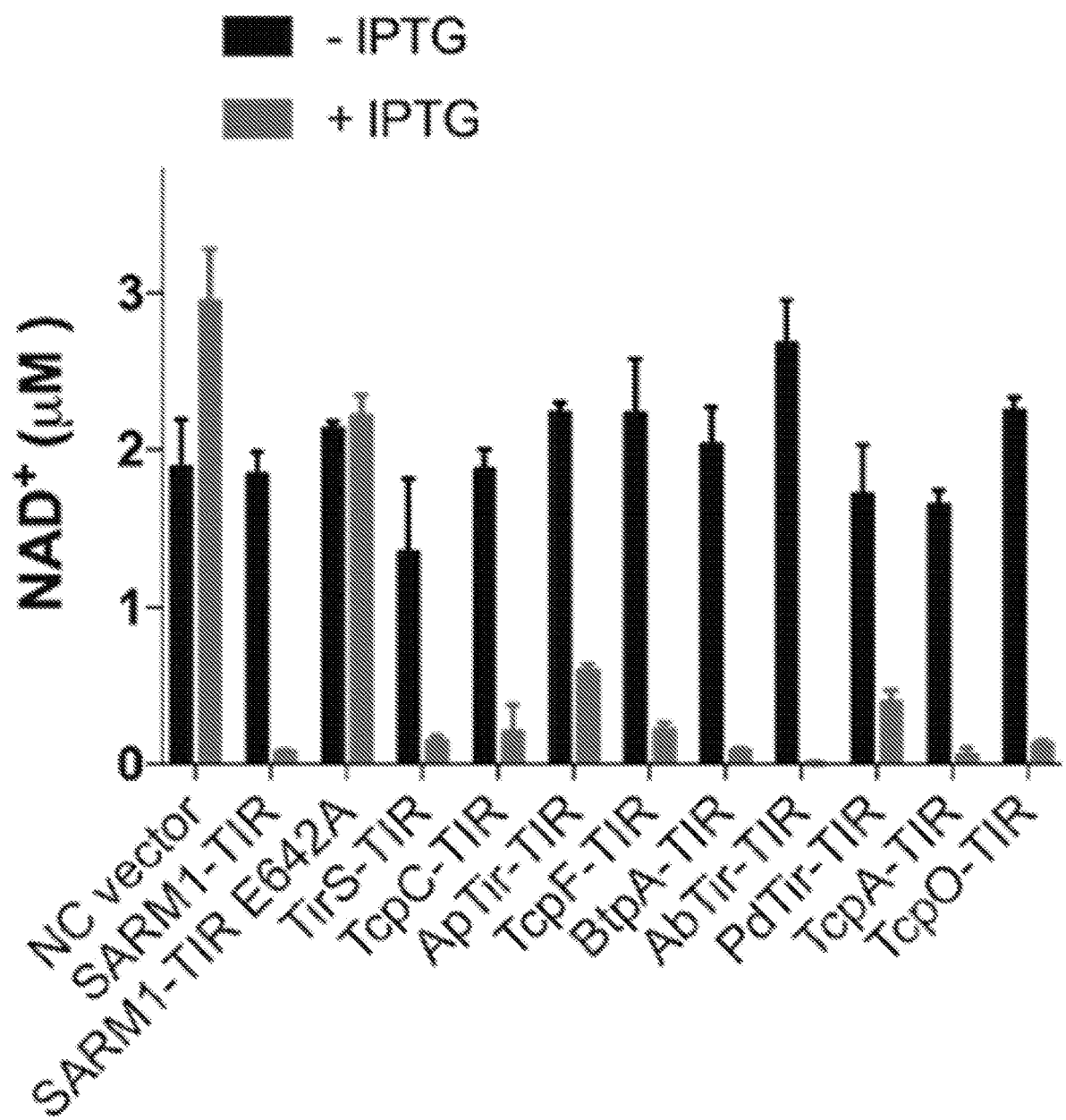
Figure 5A:
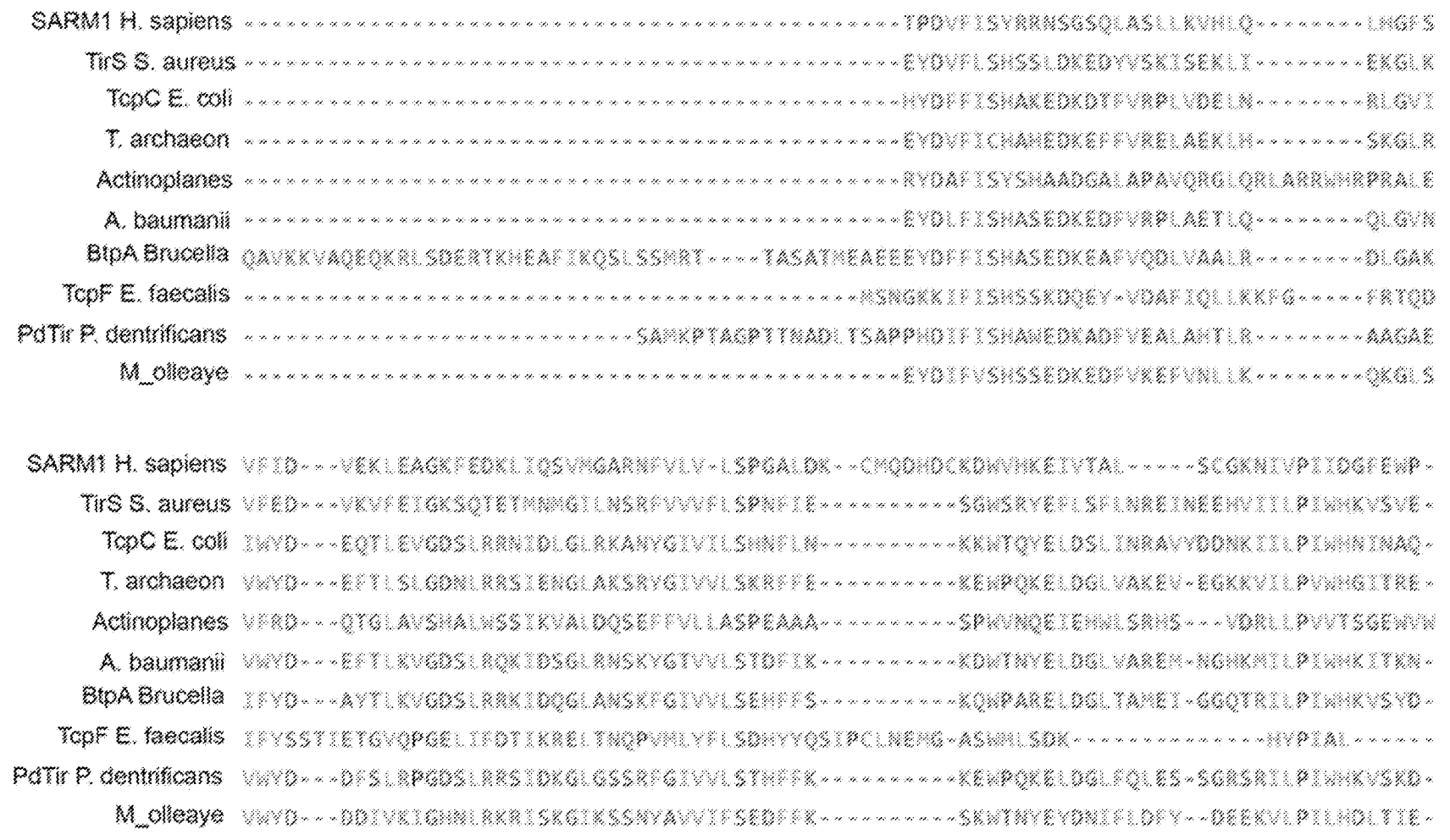
Figure 5B:
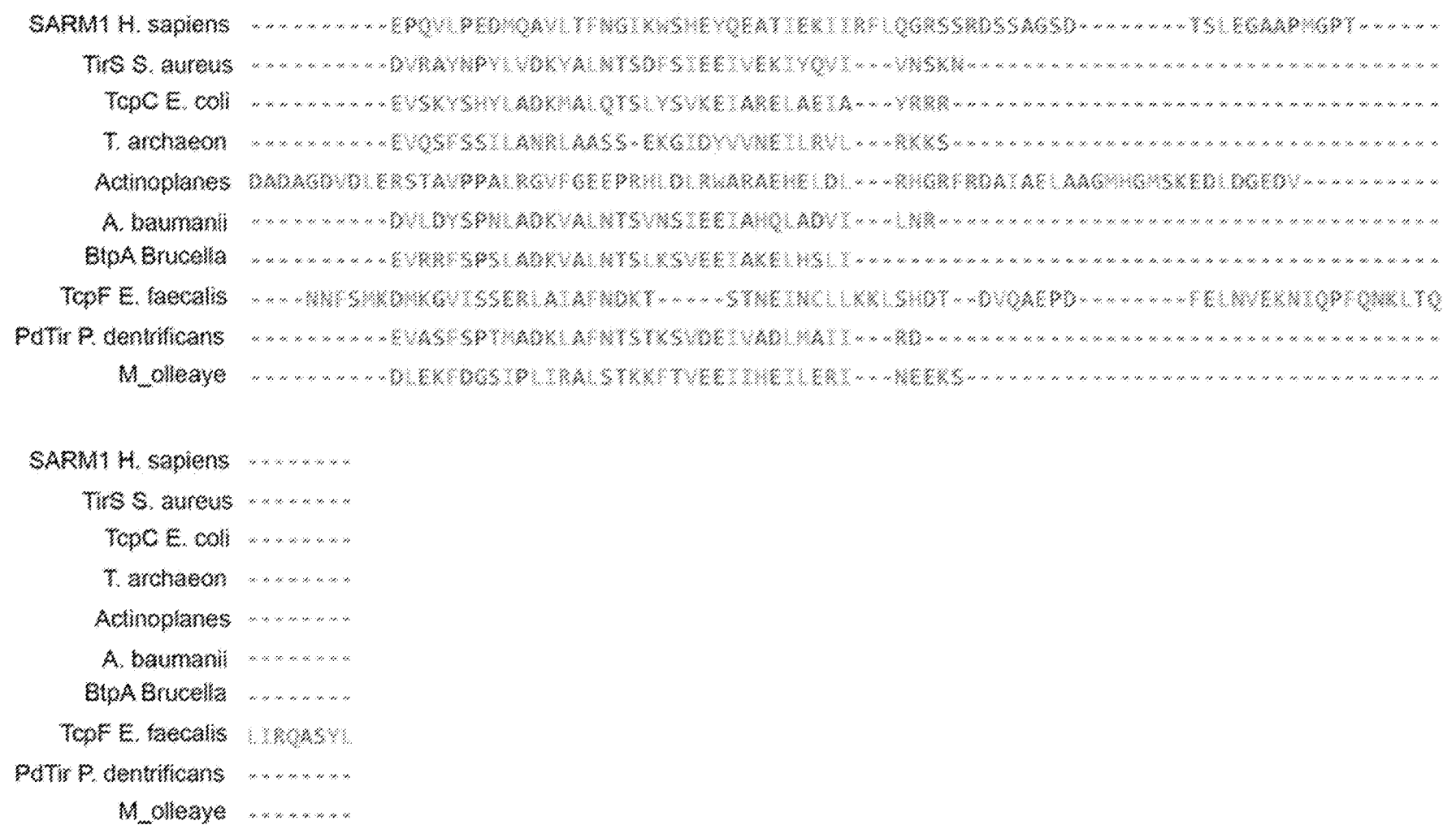

Phylogenetic studies suggest that the TIR domain of SARM1, the NADase serving as the central executioner of injury-induced axonal death, is closely related to prokaryotic TIR domains (Zhang et al., 2011). This raises the question of whether TIR NADase activity is an evolved function unique to SARM1, or whether such an enzymatic activity may be the primordial function of TIR domains. To distinguish between these two possibilities, we developed an assay to screen for NADase activity in host *E. coli* expressing candidate TIR domains (FIG. 1A). We tested TIR domains from pathogenic bacteria, including those noted for extreme antibiotic resistance, TIR domains from non-pathogenic bacteria, TIR domains from archaea, as well as the SARM1 TIR domain (FIG. 1B, FIG. 1C; FIG. 5). As previously observed, IPTG protein induction of wild type (enzymatically active) SARM1-TIR induces NAD+ loss in host *E. coli* (FIG. 1D; Essuman et al., 2017). In contrast, $NAD^+$ was not depleted after IPTG induction in *E. coli* harboring either a control plasmid or a plasmid encoding enzymatically dead SARM1-TIR (SARM1-TIR(E642A)) (FIG. 1D). We therefore reasoned that $NAD^+$ levels would be lower in *E. coli* expressing enzymatically active prokaryotic TIR domains. Consistent with this hypothesis, we found that expression of TIR domains from many pathogenic bacteria like *Staphylococcus aureus* (methicillin sensitive and methicillin resistant), uropathogenic *Escherichia coli*, and *Acinetobacter baumannii* induced $NAD^+$ depletion in the host *E. coli*. Further, TIR domains from bacteria considered non-virulent such as *Paracoccus dentrificans* and *Actinoplanes* species, or from the archaea *Theionarchaea archaeon*, also caused loss of $NAD^+$ in host *E. coli* (FIG. 1D). These observations indicate that, like SARM1, TIR domains from diverse prokaryotes induce losses of $NAD^+$ in *E. coli* host.

Characterization of an Intrinsic NADase Activity in Prokaryotic TIR Domains.

Figure 2A:
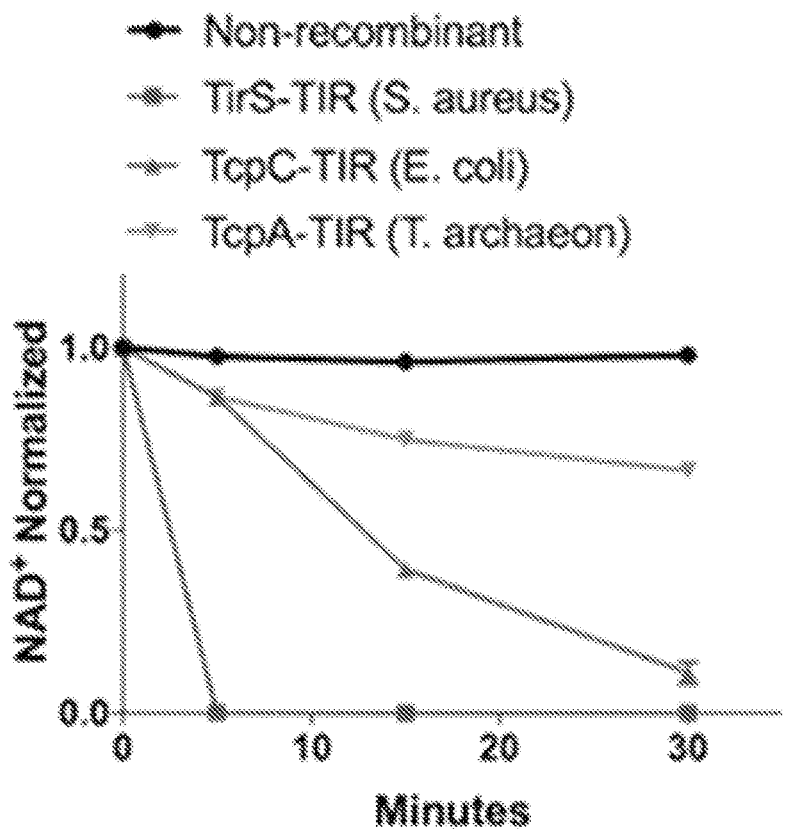
FIG. 2A, FIG. 2B, FIG. 2C, FIG. 2D, FIG. 2E FIG. 2F, FIG. 2G, FIG. 2H, FIG. 2I, FIG. 2J, FIG. 2K and FIG. 2L depicts the characterization of an intrinsic $NAD^+$ glycohydrolase activity in a subset of prokaryotic TIR domains.
Figure 2B:
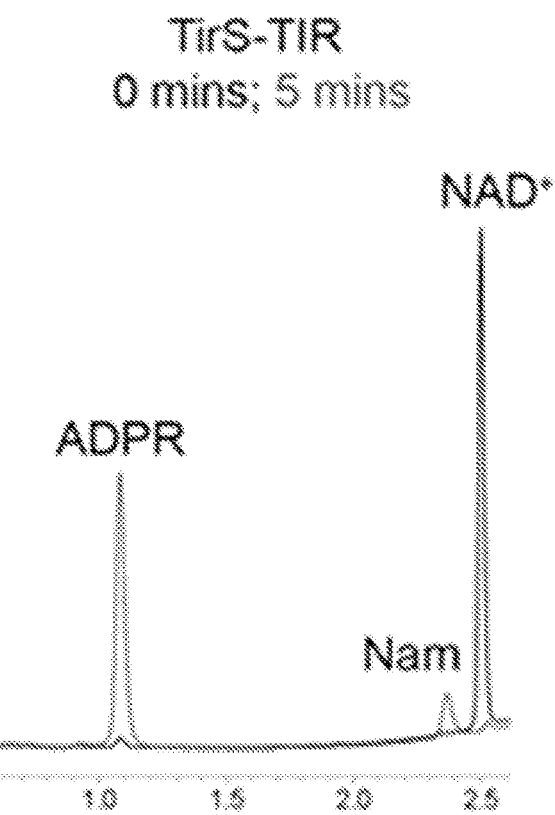
Figure 2C:
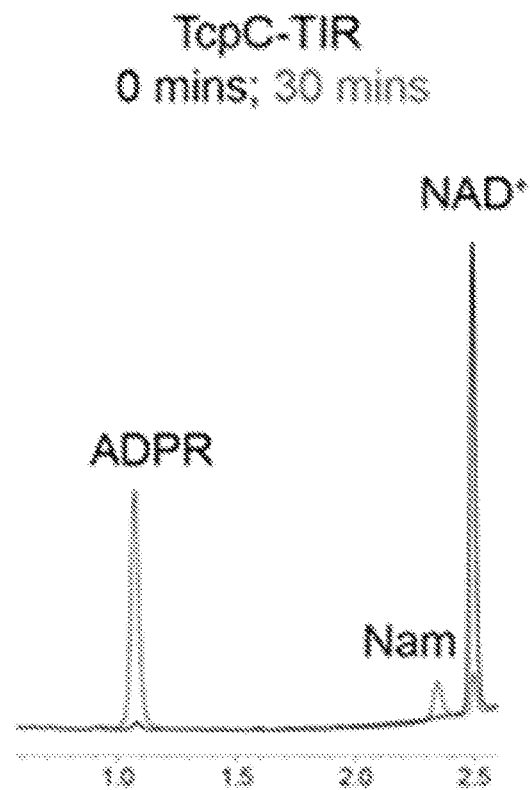

The $NAD^+$ depletion observed in *E. coli* expressing TIR domains from multiple prokaryotic proteins stimulated us to test whether this was due to an intrinsic $NAD^+$ cleavage activity, or was a secondary effect on *E. coli* metabolism. To test the intrinsic TIR enzymatic activity hypothesis, we adopted a cell-free protein transcription and translation system reconstituted from purified components from *E. coli* to synthesize recombinant TIR protein (Shimizu et al., 2001). This system does not contain known NADases, and we experimentally verified that it is devoid of $NAD^+$ cleavage activity (Essuman et al., 2017). We programmed this cell-free system with recombinant DNA encoding double tagged (StrepTag and 6×His) TIR domains of TirS and TcpC, from the Gram-positive bacteria *Staphylococcus aureus* and Gram-negative bacteria *Escherichia coli* CFT073 respectively. We also tested a TIR domain from the archaea *Theionarchaea archaeon*, which we name TcpA-TIR. We purified the synthesized TIR proteins by tandem affinity purification and tested their ability to cleave NAD+. Cobalt beads laden with purified TIR proteins were incubated with NAD+ (5 µM), and metabolites were extracted and analyzed using High Performance Liquid Chromatography (HPLC). We found that all three prokaryotic TIR domains cleave NAD$^+$, with the TIR domain of *Staphylococcus aureus* showing the most rapid cleavage (FIG. 2A).

Figure 2D:
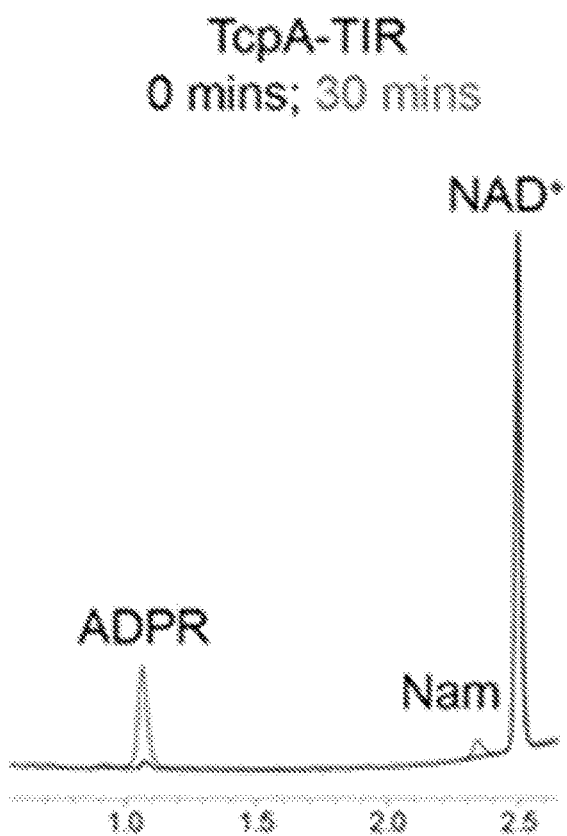
Figure 2E:
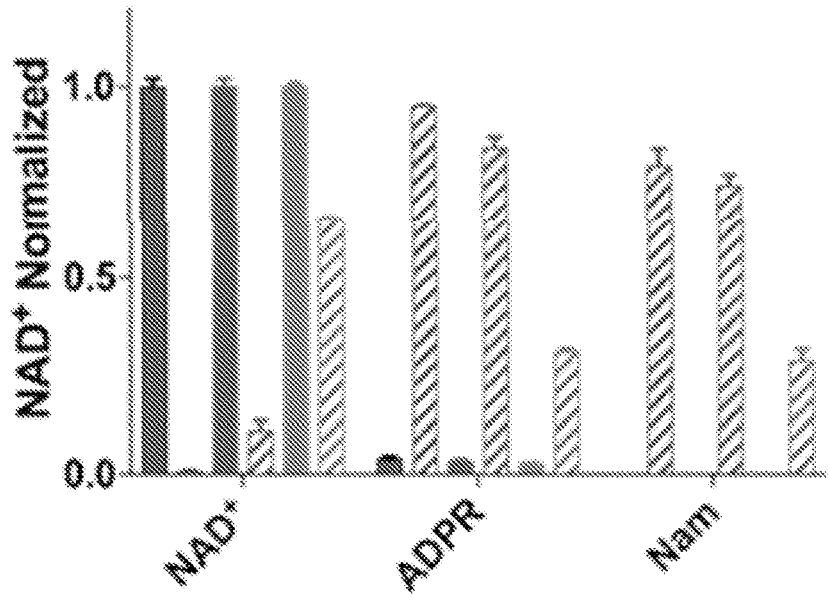
Figure 6A:
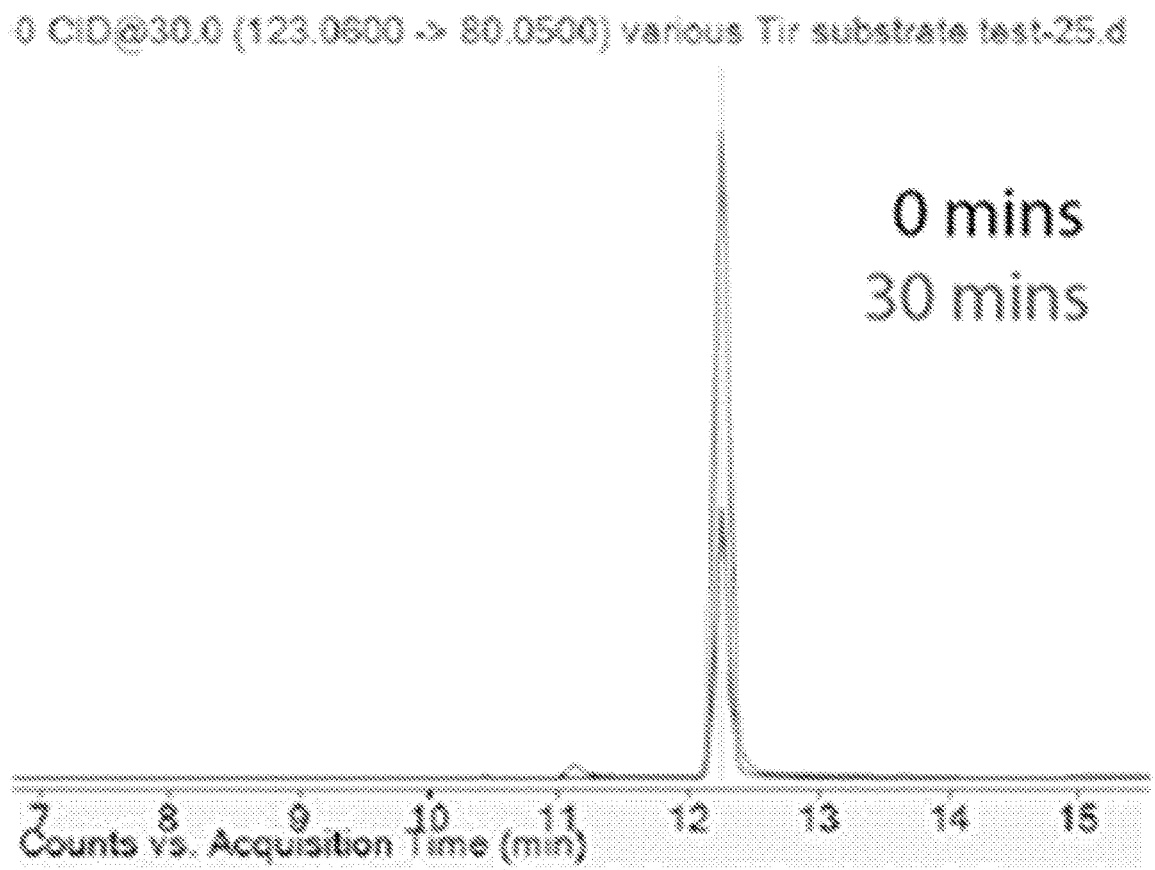
FIG. 6A, FIG. 6B, FIG. 6C, FIG. 6D, FIG. 6E, FIG. 6F and FIG. 6G show mass spectra identifying products of prokaryotic TIR $NAD^+$ cleavage reactions.
Figure 6B:
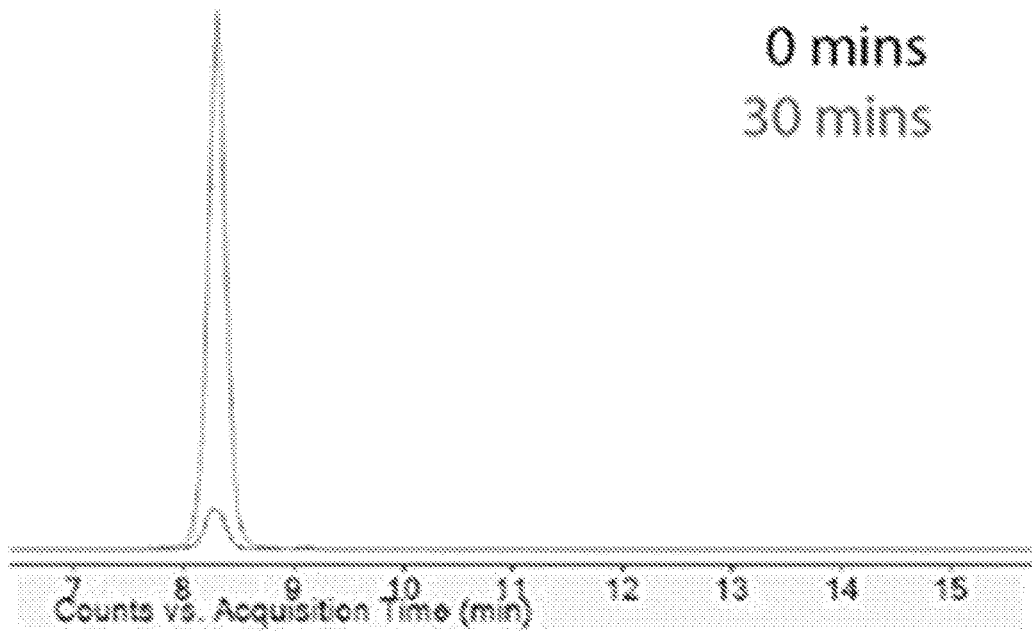
Figure 6C:
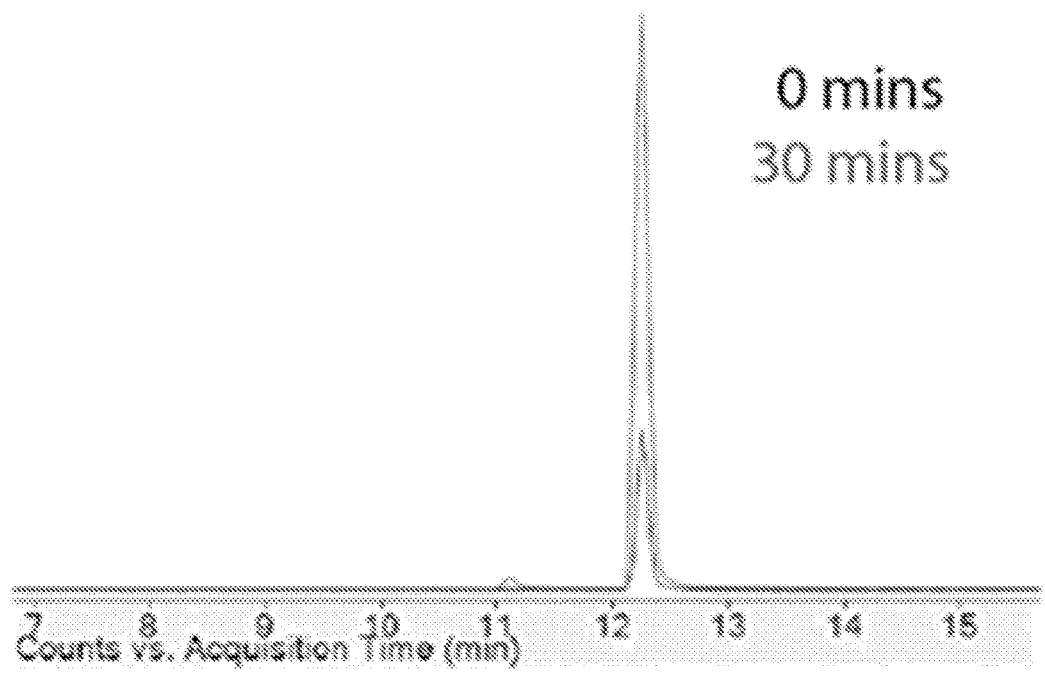
Figure 6D:
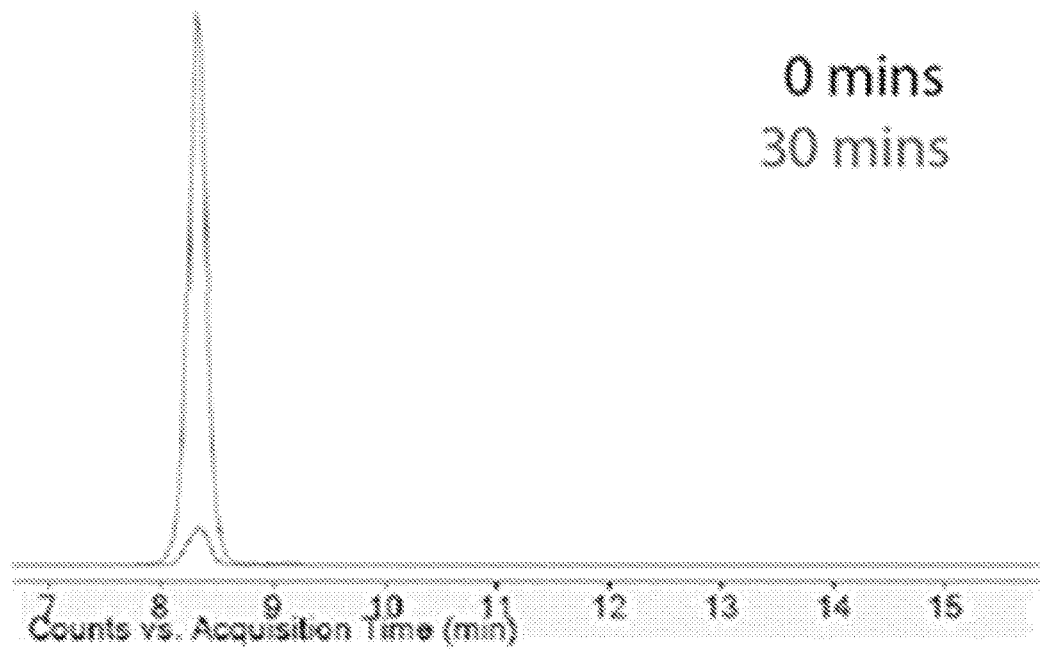
Figure 6E:
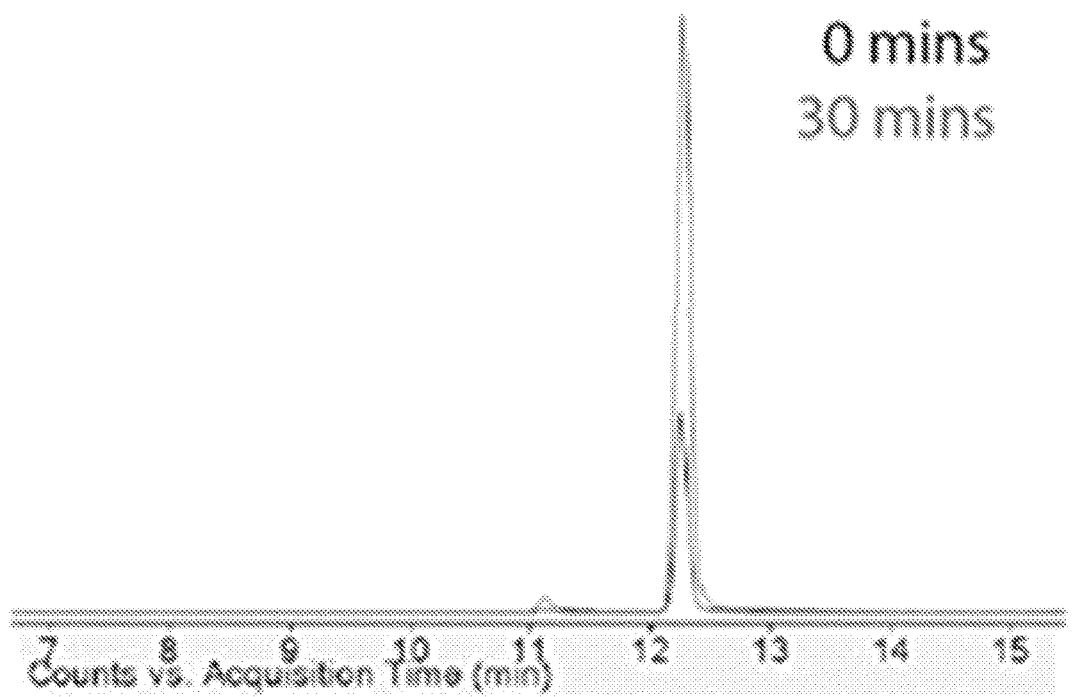
Figure 6F:
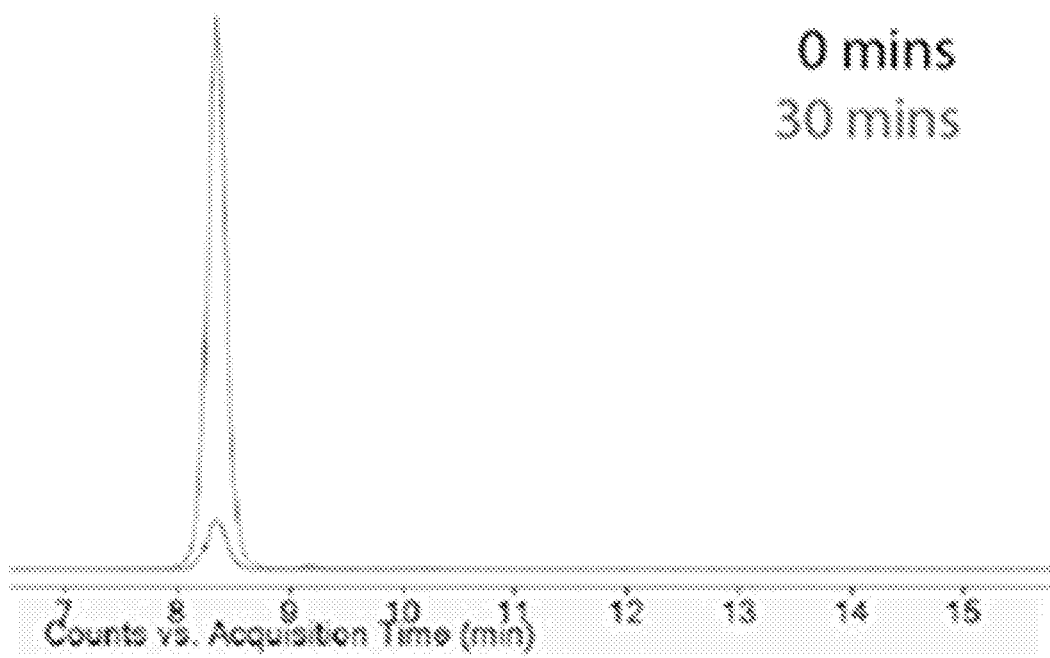
Figure 6G:

Since different NAD$^+$ consuming enzymes display uniquely characteristic reaction product profiles, we asked what products were formed by these prokaryotic TIR domains. Using HPLC and LC-MS, we found that all three prokaryotic TIR domains cleave NAD$^+$ into Nicotinamide (Nam) and ADP-Ribose (ADPR) (FIG. 2B-2E; FIG. 6). However, unlike SARM1, the *Staphylococcus aureus* TirS-TIR and *Escherichia coli* CFT073 TcpC-TIR did not produce cADPR as a product (FIG. 6G). A minor trace peak corresponding to cADPR was detected in LC-MS samples of the archaeal protein TcpA-TIR, but was not observed on HPLC chromatograms (FIG. 6G and FIG. 2D). Hence, we conclude that the prokaryotic TIR domains from *S. aureus* and *E. coli* CFT073 possess a pure NAD$^+$ glycohydrolase activity, which is distinct from the dual NAD$^+$ glycohydrolase and cyclase activity of SARM1-TIR.

Figure 2F:
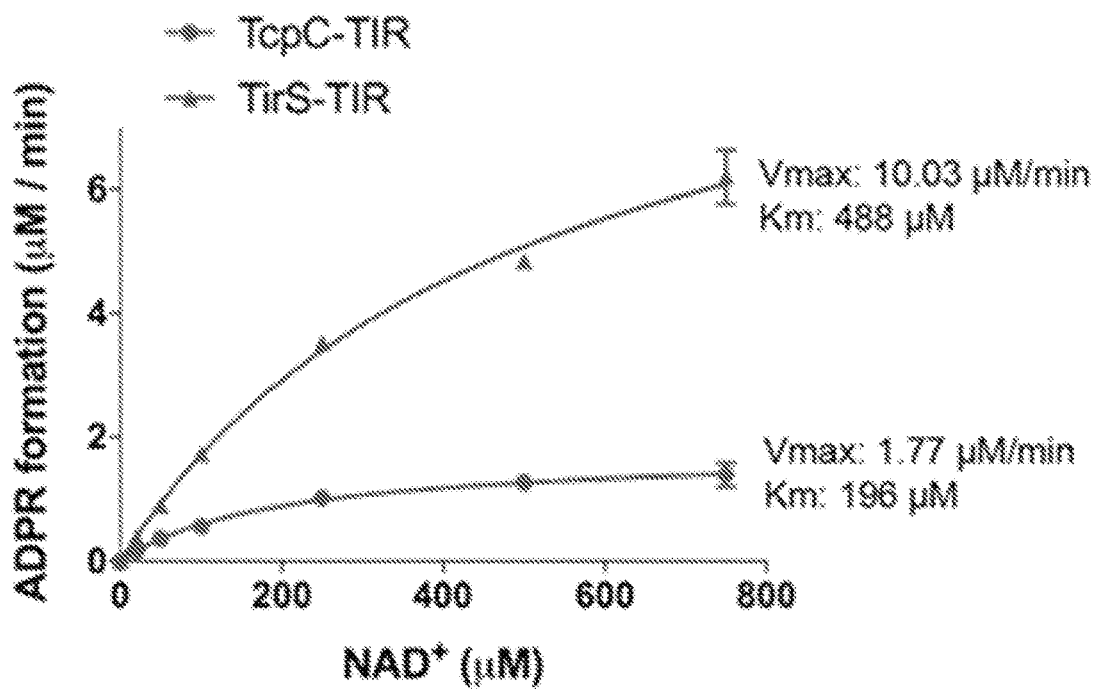

In characterizing the activity of these prokaryotic TIR domains, we examined their Michaelis-Menten parameters using the purified TIR proteins. The *E. coli* TcpC-TIR exhibited an estimated $K_m$ of 196 µM and a $V_{max}$ of approximately 1.8 µM/min, while the *S. aureus* TirS-TIR displayed an estimated $K_m$ of 490 µM and a $V_{max}$ of ~10 µM/min (FIG. 2F). The *E. coli* TcpC-TIR $K_m$ of 196 µM is very close to the reported 188 µM $K_m$ value of the bacterial virulence effector SPN (*Streptococcus Pyogenes* NAD$^+$ glycohydrolase) that is implicated in its virulence (Ghosh et al., 2010). Further, the $K_m$ values of both TcpC-TIR and TirS-TIR fall within the range of total NAD$^+$ content in *E. coli* and mammalian cells (Canto et al., 2015; Zhou et al., 2011), suggesting that these TIRs could influence NAD$^+$ levels in both eukaryotes and prokaryotes.

Figure 2G:
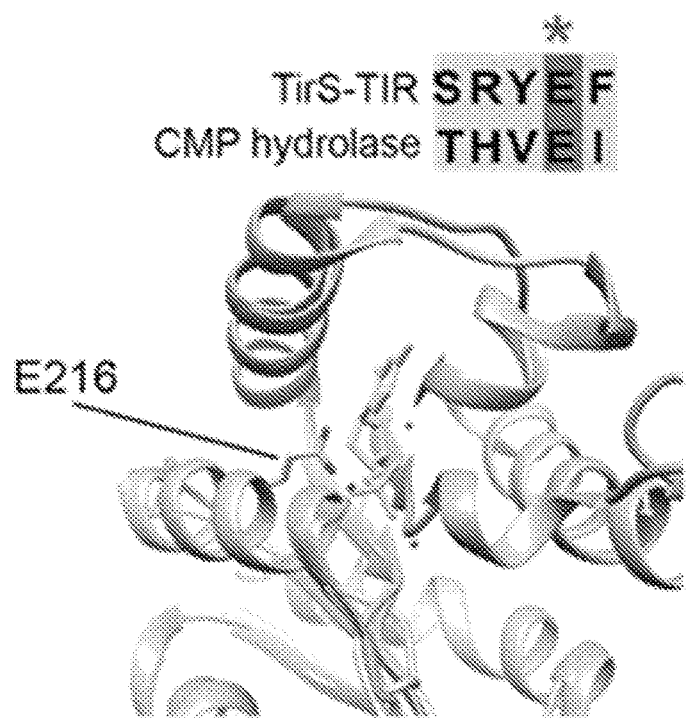
Figure 2H:
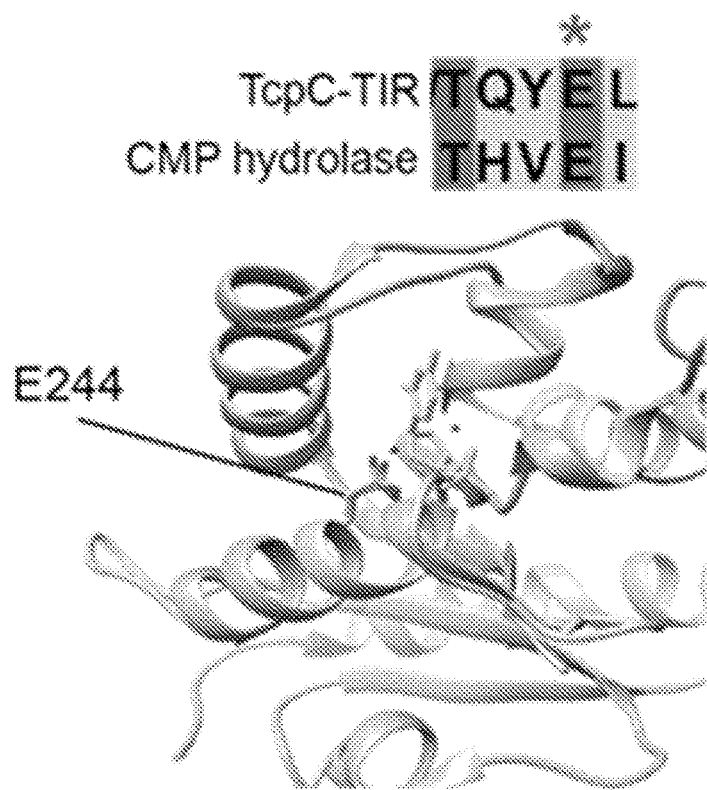
Figure 2I:
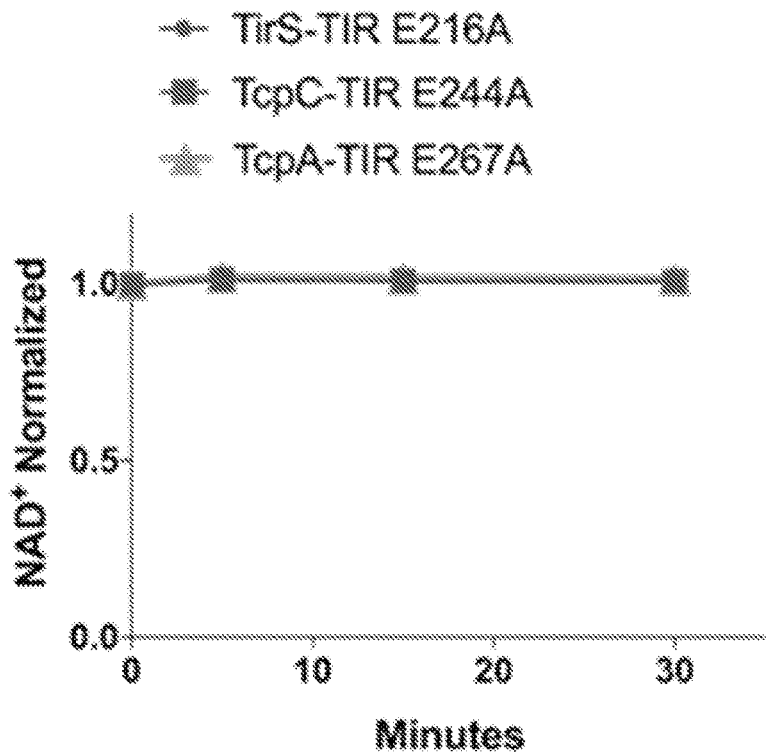
Figure 7A:
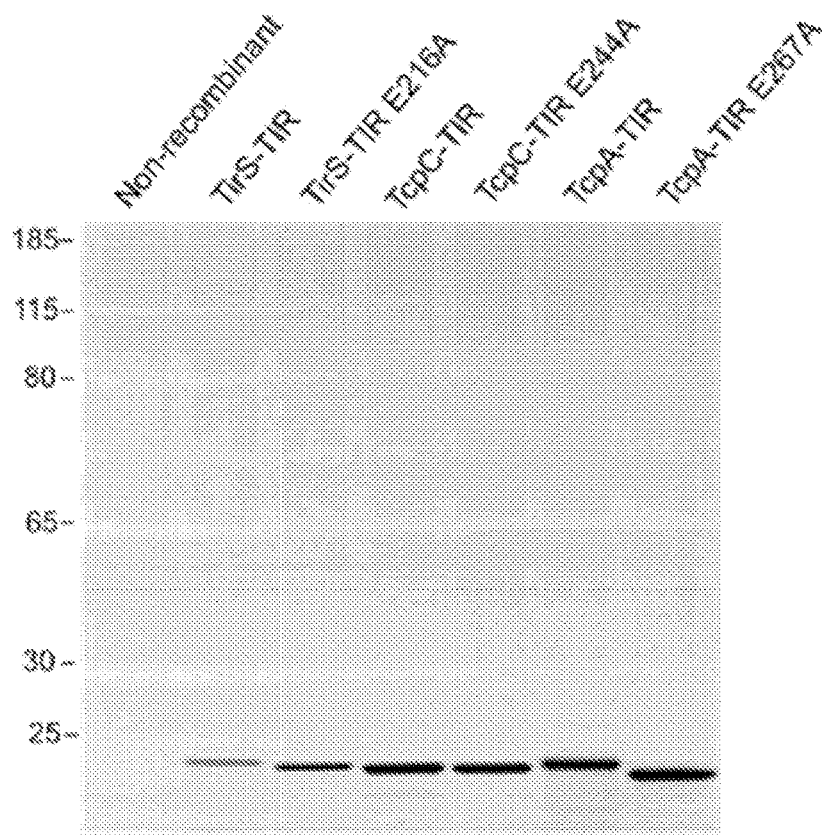
Figure 7B:
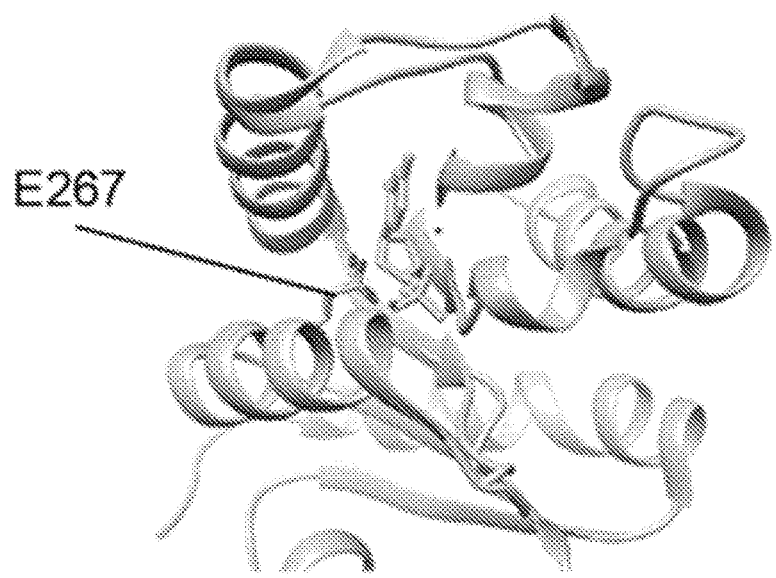

We next investigated structural elements within these prokaryotic TIR domains that contribute to NAD$^+$ cleavage. The SARM1 TIR domain has structural similarities to nucleotide hydrolases, which led us to the identification of a glutamate residue within the proposed active site of SARM1-TIR that is absolutely essential for its catalytic activity (Essuman et al., 2017). Structural motif homology searches revealed that these prokaryotic TIRs share structural similarity with other nucleotide enzymes including cytidine monophosphate (CMP) hydrolase, and nucleoside 2-deoxyribosyltransferase (Table 1). No crystal structures have been reported for SARM1 TIR or the three prokaryotic TIRs; so using SWISS modeling (Arnold et al., 2006) and the known CMP hydrolase structure (PDB: 4JEM), we generated structural models of the prokaryotic TIR domains. This analysis demonstrated that the catalytic glutamate of CMP hydrolase aligned with a conserved glutamate in the prokaryotic TIR domains (FIG. 2G, FIG. 2H and FIG. 7B). This glutamate is also the residue in SARM1-TIR that was essential for its catalytic activity (FIG. 5). We mutated this glutamate to alanine in each of the prokaryotic TIRs and found, in each case, that this abolished NADase activity (FIG. 2I). These experiments show that these TIR domains share structural homology to a family of nucleotidases, and that a conserved catalytic glutamic acid in the TIR proteins is essential for catalytic cleavage of NAD$^+$.

Figure 8A:
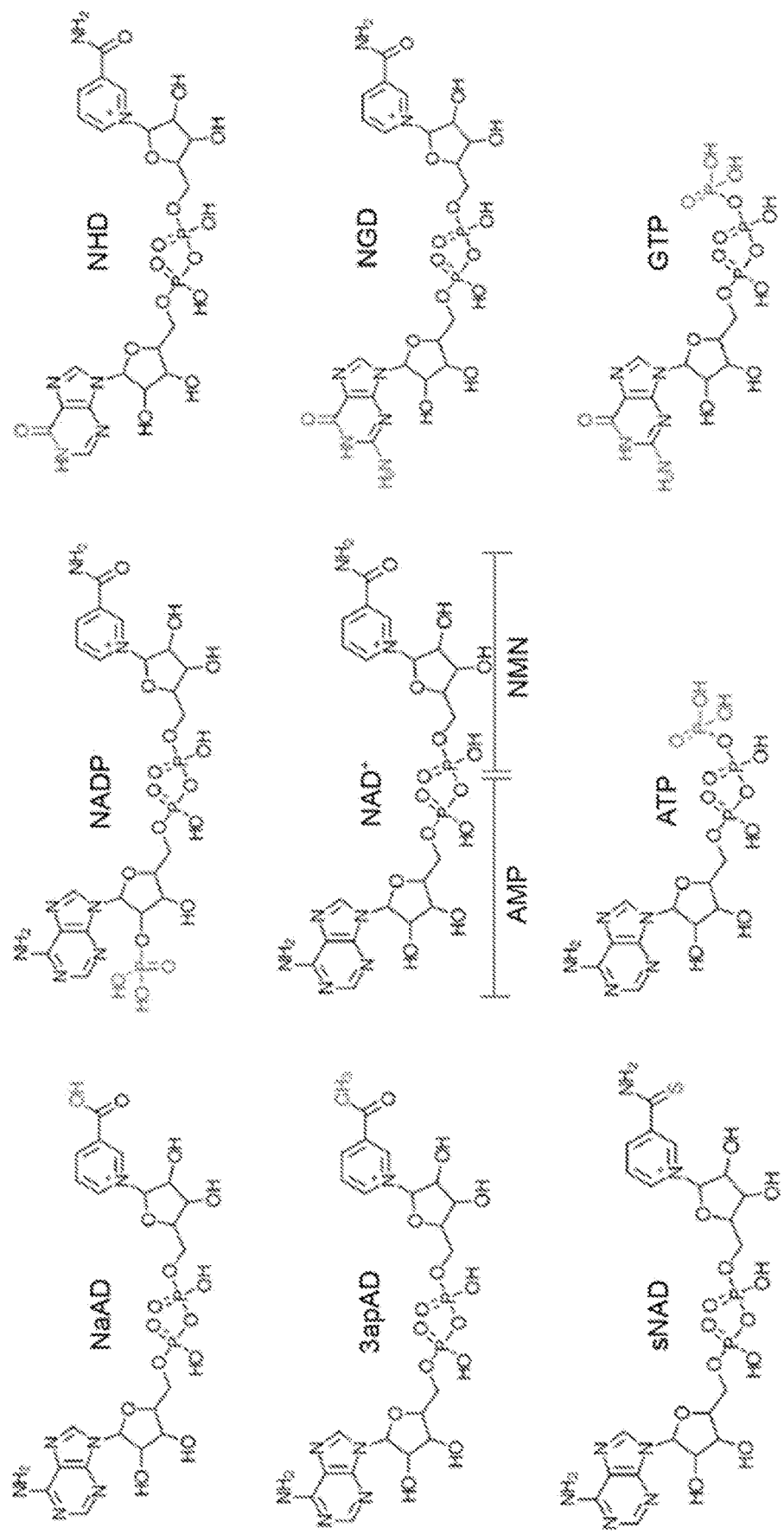
FIG. 8A.
Figure 8B:
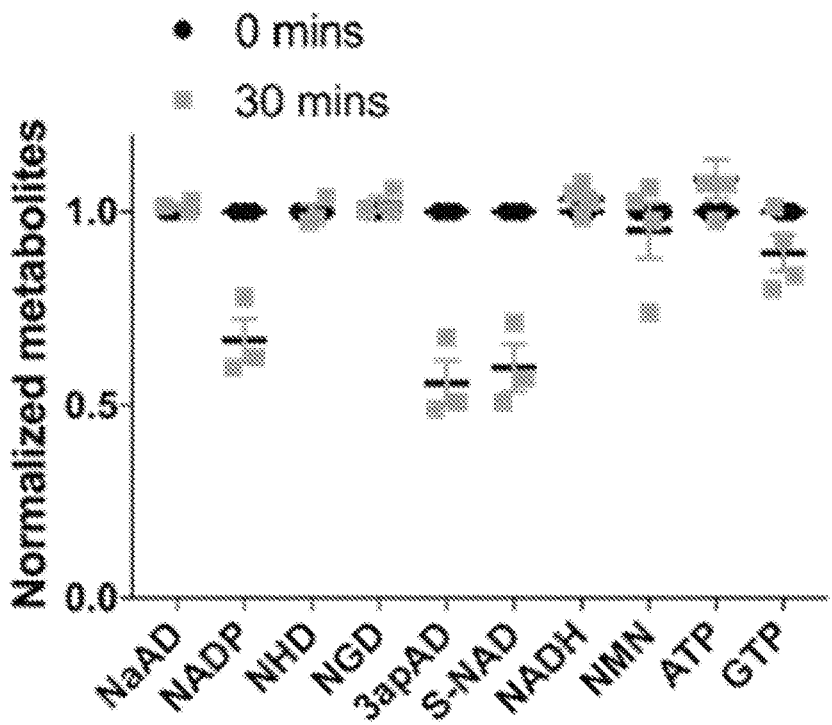
FIG. 8B and FIG. 8C show TIR domains cleave other substrates besides NAD+.
Figure 8C:
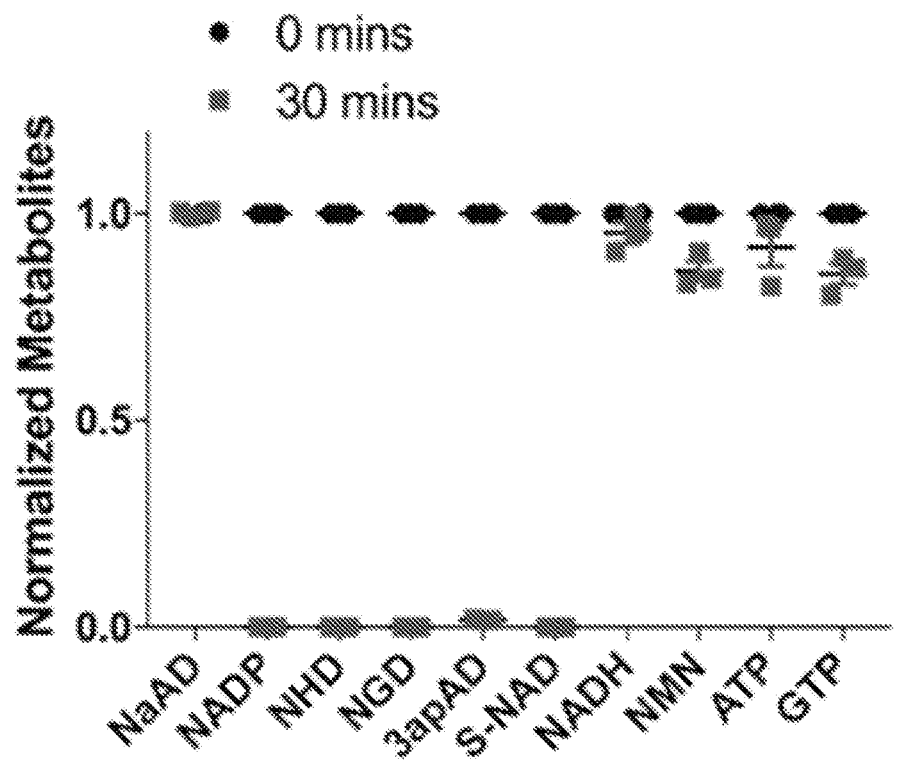

In some instances, NADases are capable of cleaving a number of related molecules, such as the NAD+ precursor Nicotinamide Mononucleotide (NMN) in the case of CD38 (Sauve et al., 1998). Further, we wanted to determine whether prokaryotic TIRs could cleave additional substrates, providing additional paths to modifying cell metabolism. To examine the substrate specificity of the prokaryotic TIR domains, we tested their activity using a wide variety of metabolites and analogs. These included biologically important NAD$^+$ analogs such as NADH and Nicotinamide Adenine Dinucleotide Phosphate (NADP$^+$) that help maintain cellular redox state (Ying, 2008), key cellular energetic nucleotides like ATP and GTP, as well as NAD$^+$ analogs like 3-acetylpyridine adenine dinucleotide (3-apAD), Nicotinic Acid Adenine Dinucleotide (NaAD), Nicotinamide Guanine Dinucleotide (NGD), and Nicotinamide Hypoxanthine Dinucleotide (NHD), which possess minor modifications compared to NAD+ that could indicate functional groups important for catalysis (FIG. 2J-2L; FIG. 8).

Figure 2J:
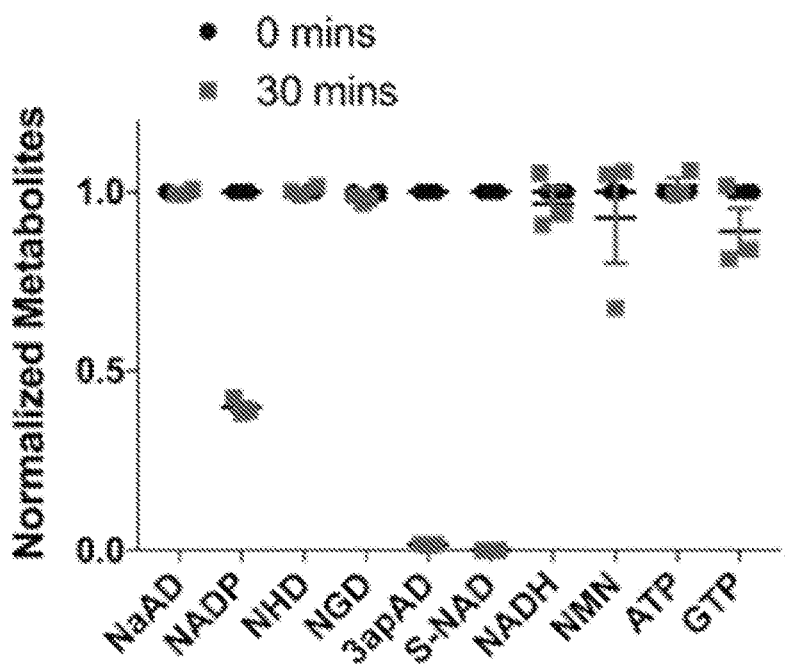
Figure 2K:
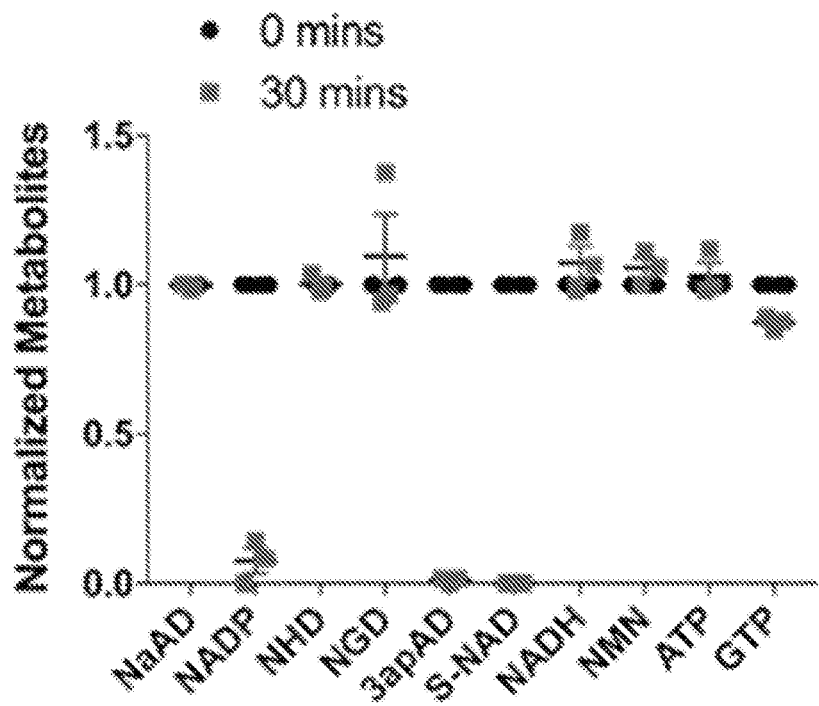
Figure 2L:
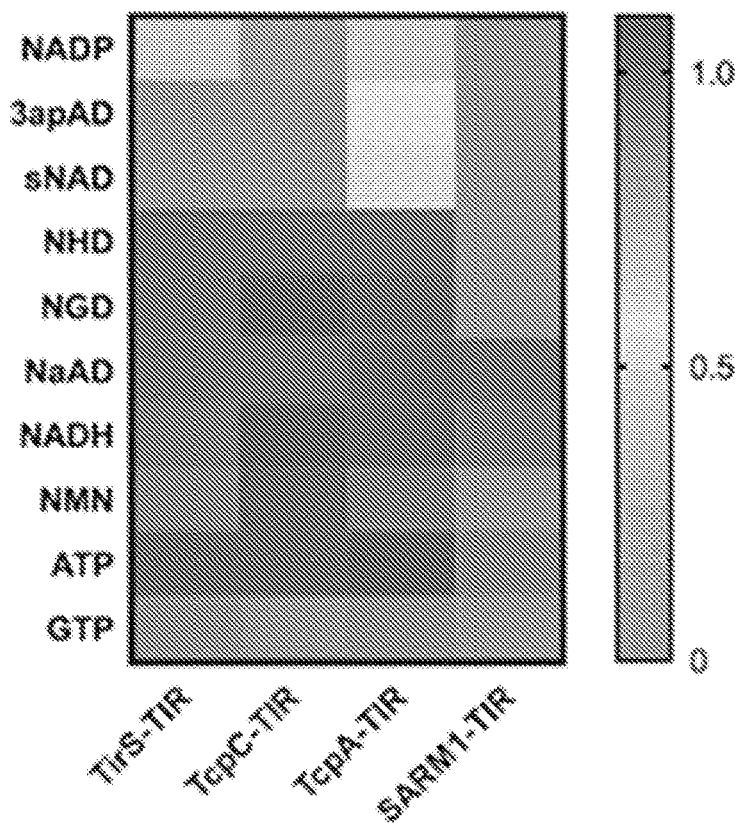

These studies demonstrated that all three prokaryotic TIR domains cleave NADP$^+$, but have little effect on NMN (FIG. 2J-2L; FIG. 8). The cleavage of NADP$^+$ suggests that these prokaryotic TIRs could modulate cellular function by altering the cellular NADP$^+$ pools necessary for maintaining levels of NADPH needed for reductive biosynthesis and protection against reactive oxygen species (Ying, 2008). Interestingly, we also found that the SARM1-TIR domain cleaves NADP$^+$, which provides an additional mechanism by which SARM1 could promote axon degeneration.

Next, we found that while all TIRs substantially cleaved 3-acetylpyridine adenine dinucleotide (3-apAD), and thionicotinamide adenine dinucleotide (sNAD), none cleaved Nicotinic Acid Adenine Dinucleotide (NaAD). These three NAD$^+$ analogs possess only a single functional group modification on the NAD$^+$ nicotinamide ring. For NaAD and 3apAD in particular, the amide (—NH2) group of the nicotinamide ring is substituted for a hydroxyl (—OH) in NaAD or a methyl (—CH3) group in 3apAD (FIG. 8A). The differential cleavage pattern suggests that this position on the NAD$^+$ molecule is important for substrate recognition or catalysis by prokaryotic TIR domains.

Additionally, we noted that while prokaryotic TIRs did not cleave NHD or NGD, SARM1-TIR cleaved both of these substrates (FIG. 2J-2L; FIG. 8). Interestingly, both NHD and NGD are also cleaved by ADP-Ribosyl cyclases like CD38 (Graeff et al., 1994; Graeff et al., 1996). In particular, NGD has been used to probe the activity of proteins in the ADP-Ribosyl cyclase family that generate cADPR (Graeff et al., 1994; Graeff et al., 1996). These results clearly show clear differences between these prokaryotic TIR domains and their mammalian homolog SARM1, and are consistent with the lack of observed cyclase activity in the prokaryotic TirS-TIR and TcpC-TIR proteins.

Finally, we were unable to detect substantial cleavage of either ATP or GTP by any TIR domain, suggesting the substrate specificity may be limited to nucleotide analogs that more closely resemble the NAD$^+$ molecule. Altogether, our results indicate that the prokaryotic TIRs are positioned to influence various aspects of cellular metabolism through their cleavage of NAD$^+$ or its close analogs, and that functional groups associated with the nicotinamide ring of the NAD$^+$ molecule dictate specificity for this class of enzymes.

Identification of a Variant Cyclic ADPR Generated by a Subset of TIR Domains.

Figure 9A:
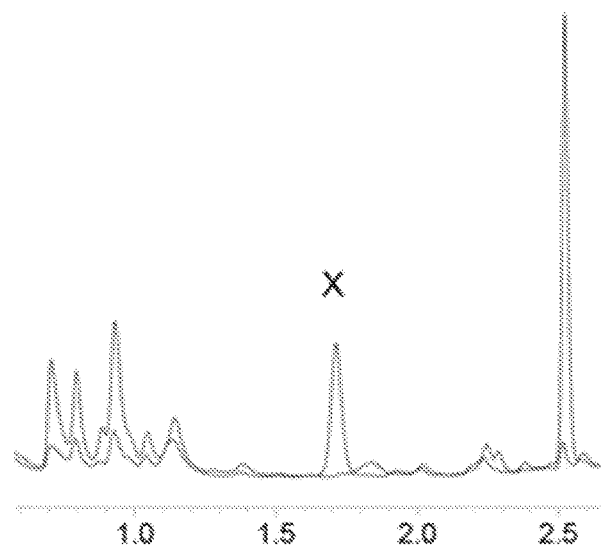
FIG. 9A, FIG. 9B, FIG. 9C, FIG. 9D and FIG. 9E show HPLC chromatograms identifying a variant cADPR molecule.

Our findings demonstrate that many prokaryotic TIR domains cleave NAD$^+$ to produce nicotinamide and ADPR. However, our results with the archaea TcpA-TIR suggested that, like SARM1, some prokaryotic TIR NADases may also be able to generate cADPR (FIG. 6G). Moreover, in our initial HPLC metabolite screen using the E. coli lysate assay, we observed a distinct and prominent peak (Metabolite X) produced by three different prokaryotic TIRs including the archaea Methanobrevibacter olleyae (TcpO-TIR), and the pathogenic bacteria, *Acinetobacter baumannii* (AbTir-TIR) and *Brucella* sp. (BtpA-TIR)(FIG. 3A-30; FIG. 9A). The HPLC retention time of this Metabolite X did not correspond to retention times of any known NAD$^+$ cleavage product such as ADPR, cADPR, or nicotinamide (FIG. 2B-2D) suggesting Metabolite X could be a previously unidentified product.

Figure 3A:
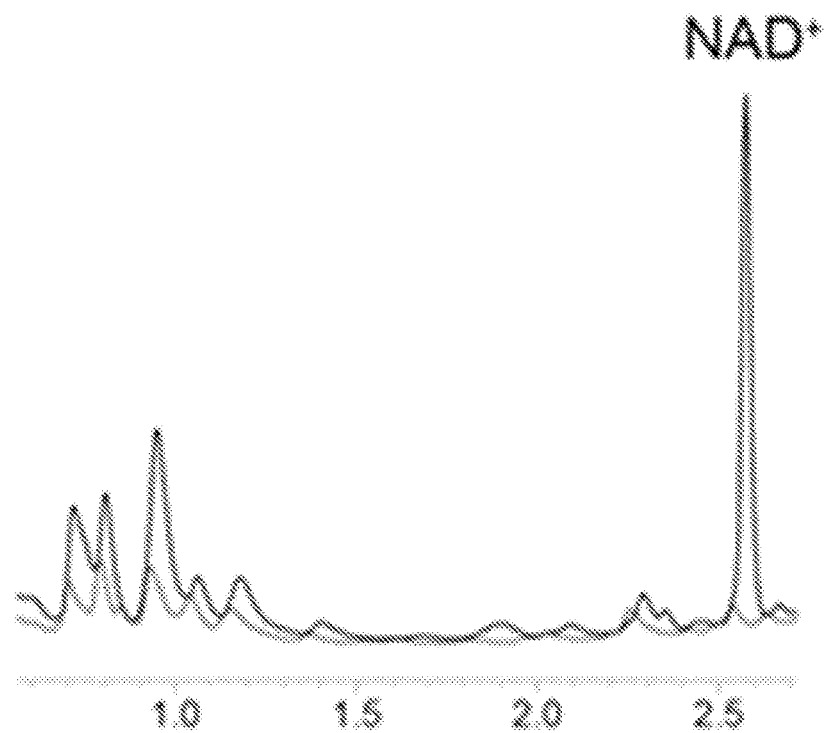
FIG. 3A, FIG. 3B, FIG. 3C, FIG. 3D, FIG. 3E, FIG. 3F, FIG. 3G, FIG. 3H and FIG. 3I depicts a variant cyclic ADPR is generated by a subset of prokaryotic TIR domains.
Figure 3B:
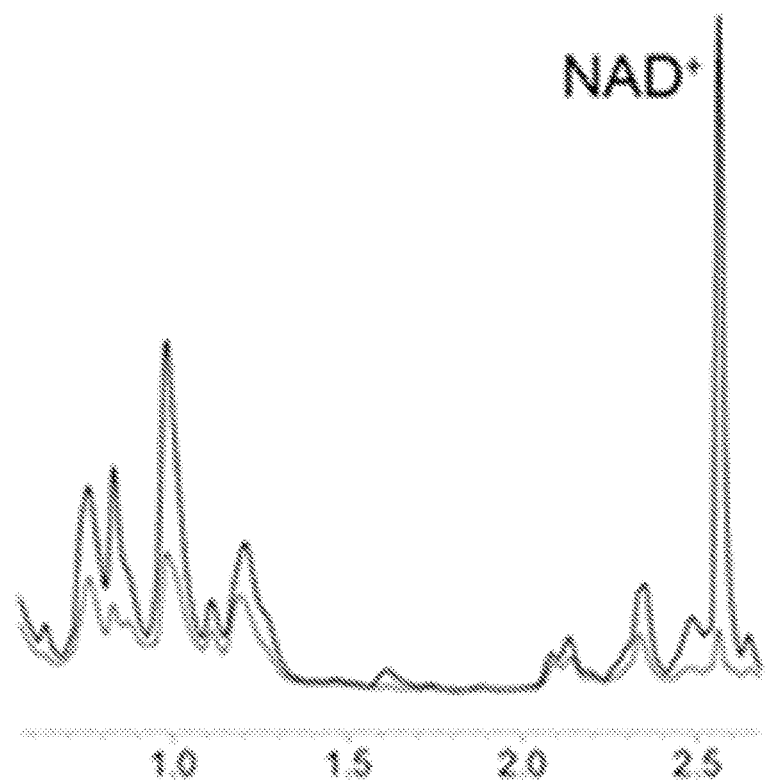
Figure 3C:
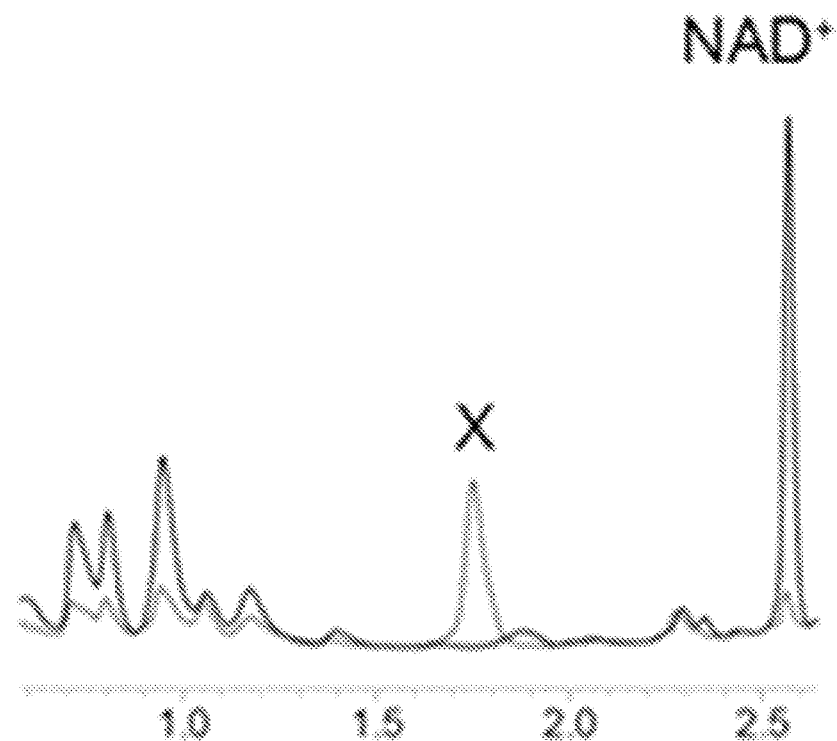
Figure 3D:
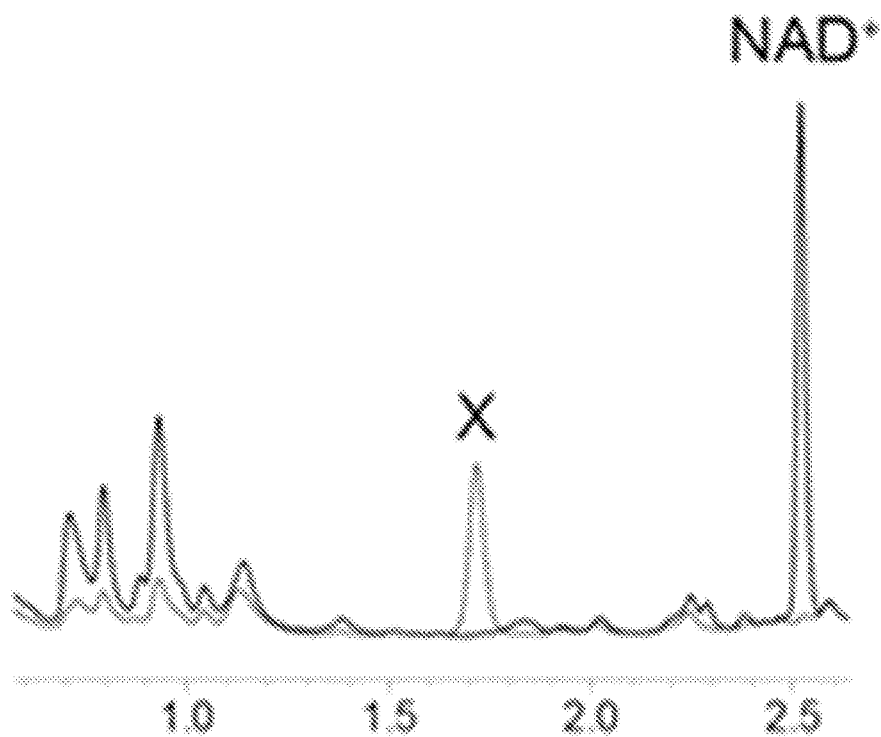
Figure 3E:
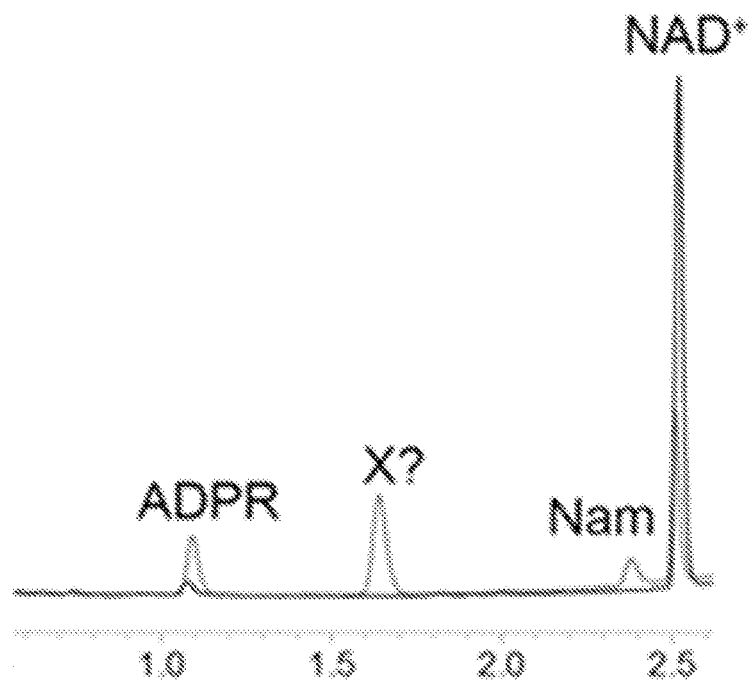
Figure 3F:
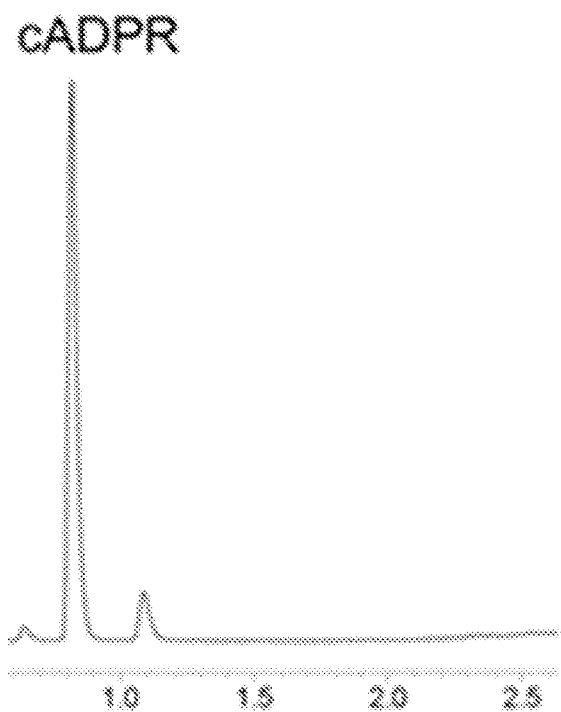
Figure 3G:
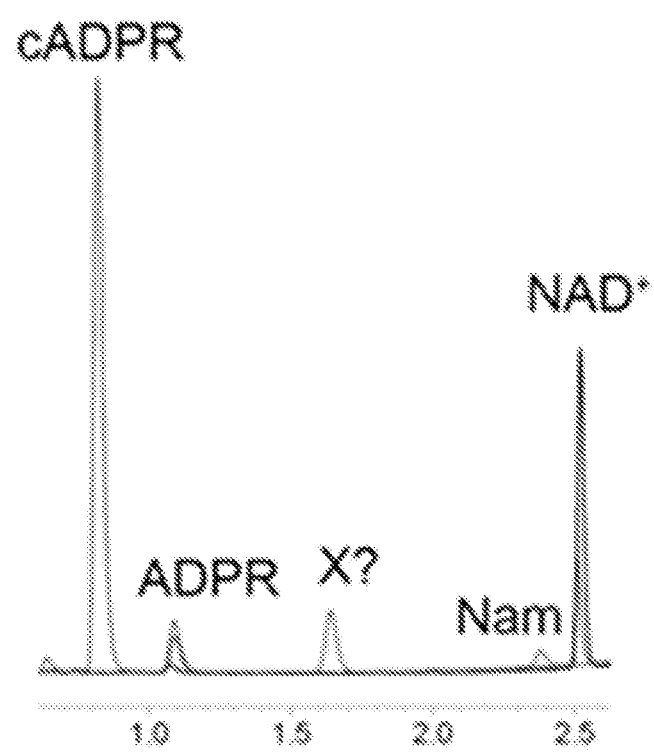

To identify Metabolite X, we asked if it was a direct cleavage product of NAD$^+$, or if it was an E. coli response secondary to TIR signaling. Using our cell-free protein translation NADase assay, we tested the TIR domain from the archaea Methanobrevibacter olleyae (TcpO-TIR). We found that it cleaved NAD$^+$ into Nicotinamide, ADP-Ribose, and a metabolite that had a retention time very close to that of Metabolite X (FIG. 3E). These data indicate that Metabolite X is a product of NAD$^+$ cleavage and raises the intriguing possibility that these TIR domains metabolize NAD$^+$ to a novel product.

Figure 9B:
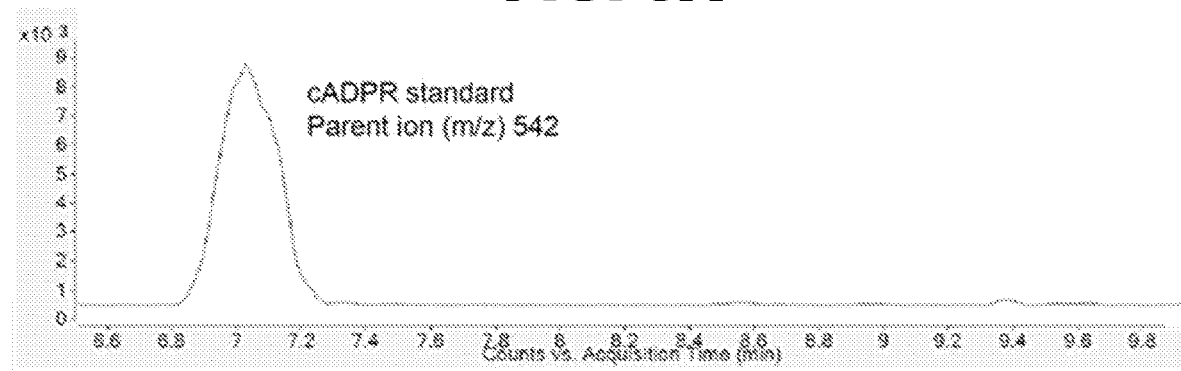
Figure 9B:
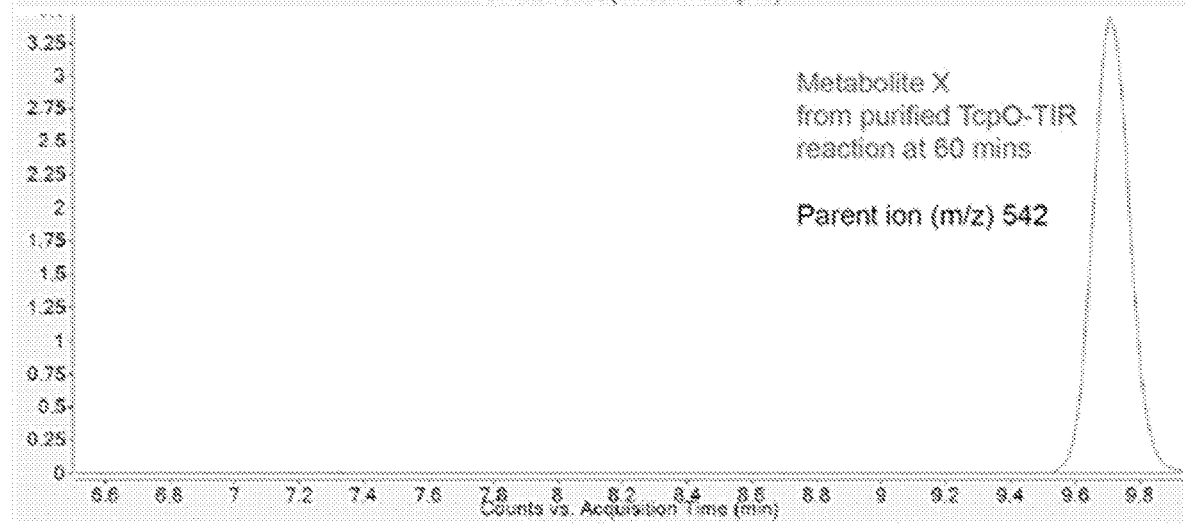

To further identify Metabolite X, we performed LC-MS analysis on the extracted metabolites from the TcpO-TIR reaction. Examination of the MS spectra (m/z=70-1200) revealed metabolites produced by the reaction (compare 0 vs. 30 min) with m/z of 664, 123, 560, and 542, which correspond to NAD$^+$, Nicotinamide, ADP-Ribose, and cADPR respectively (FIG. 9B and data not shown). Metabolite X is a molecule with an m/z of 542, which corresponds to cADPR; however, the LC retention time of m/z 542 was dramatically different from that of the cADPR standard (FIG. 9B). Further, on a separate LC instrument, both commercially available cADPR preparations (FIG. 3F and FIG. 3G) and cADPR generated from a SARM1-TIR programmed reaction (Essuman et al., 2017), had retention times distinct from Metabolite X indicating it is not cADPR.

Figure 3H:
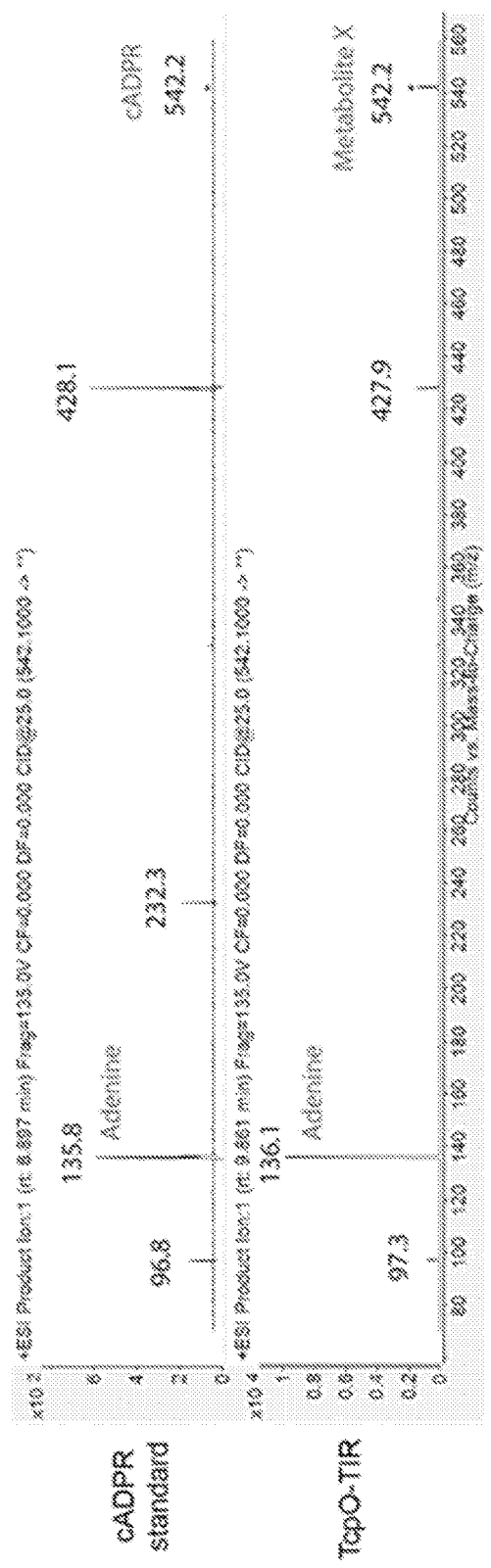
Figure 3I:
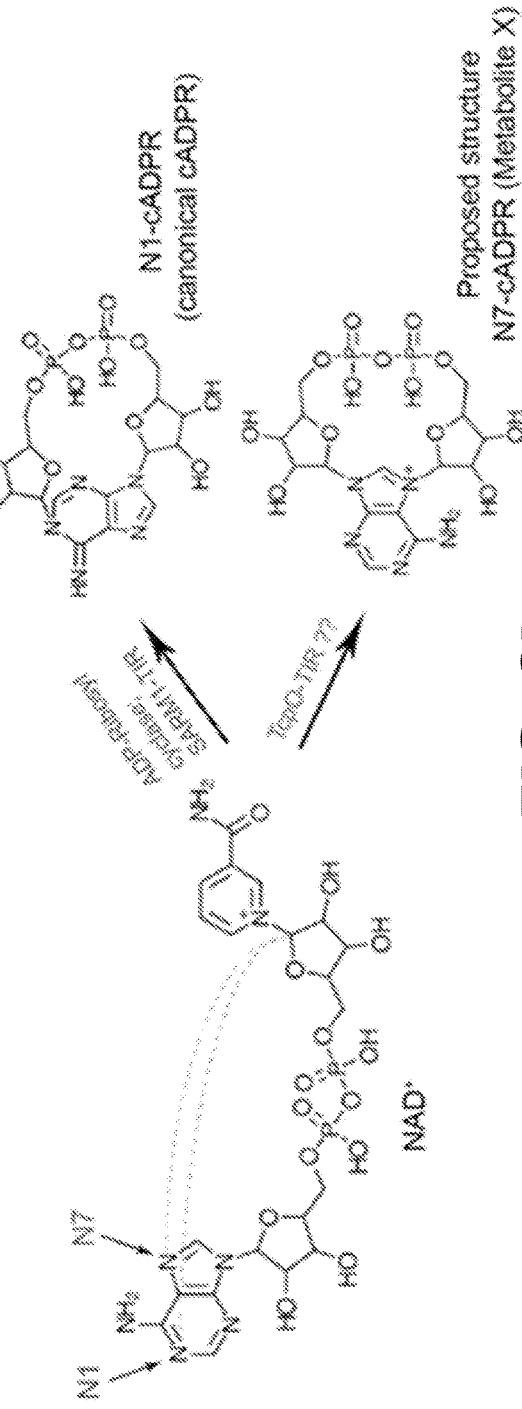
Figure 9C:
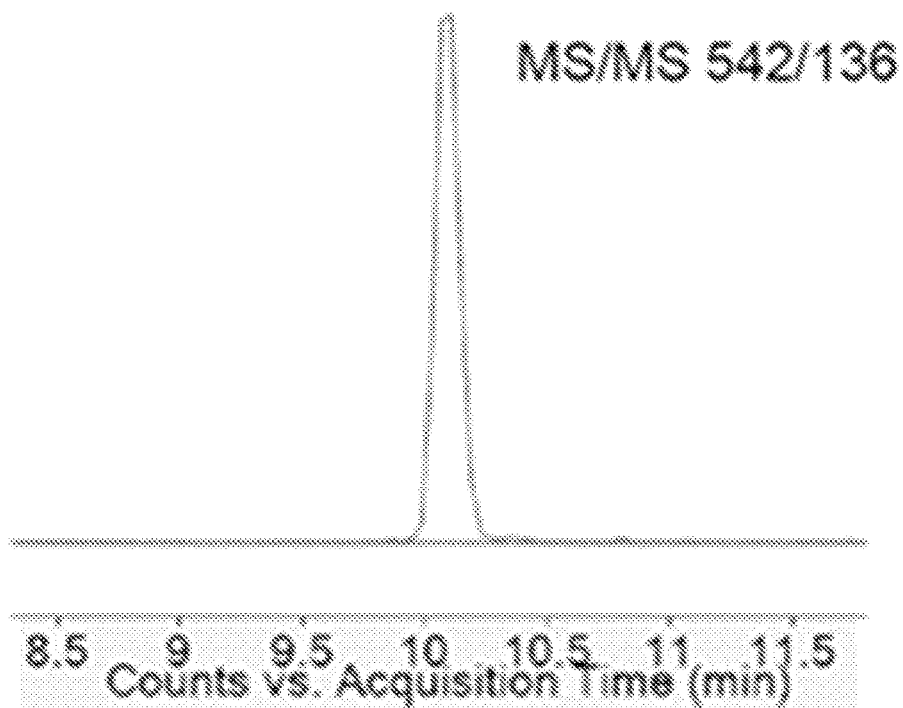
Figure 9D:
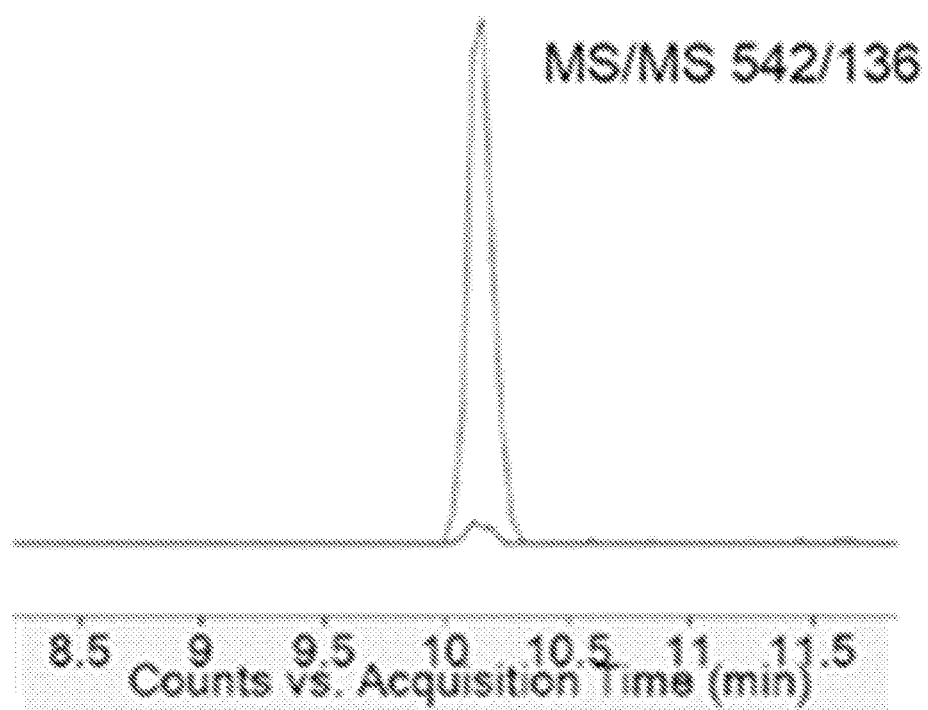
Figure 9E:
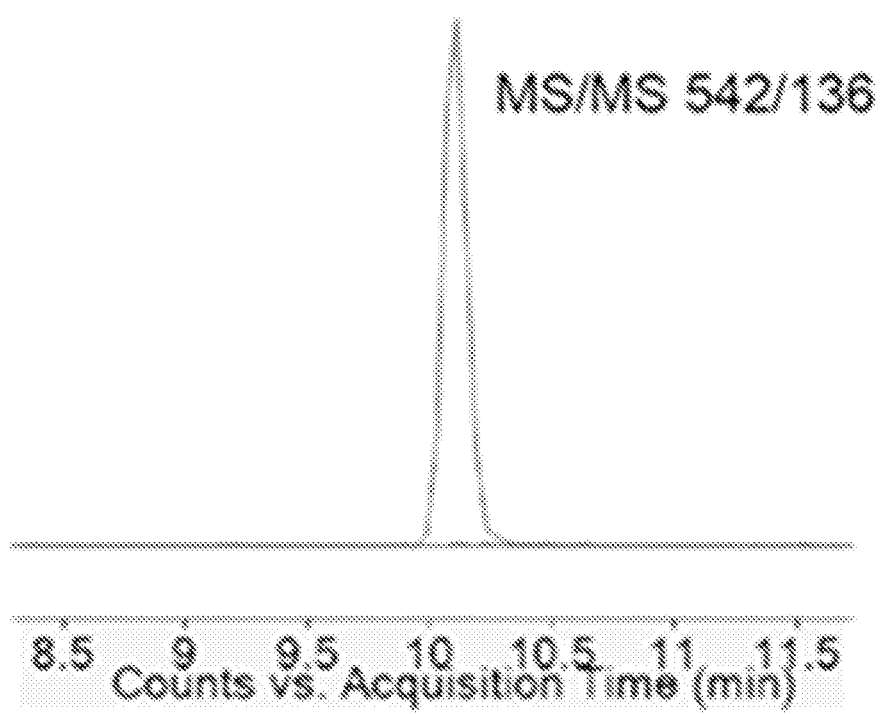
Figure 10A:
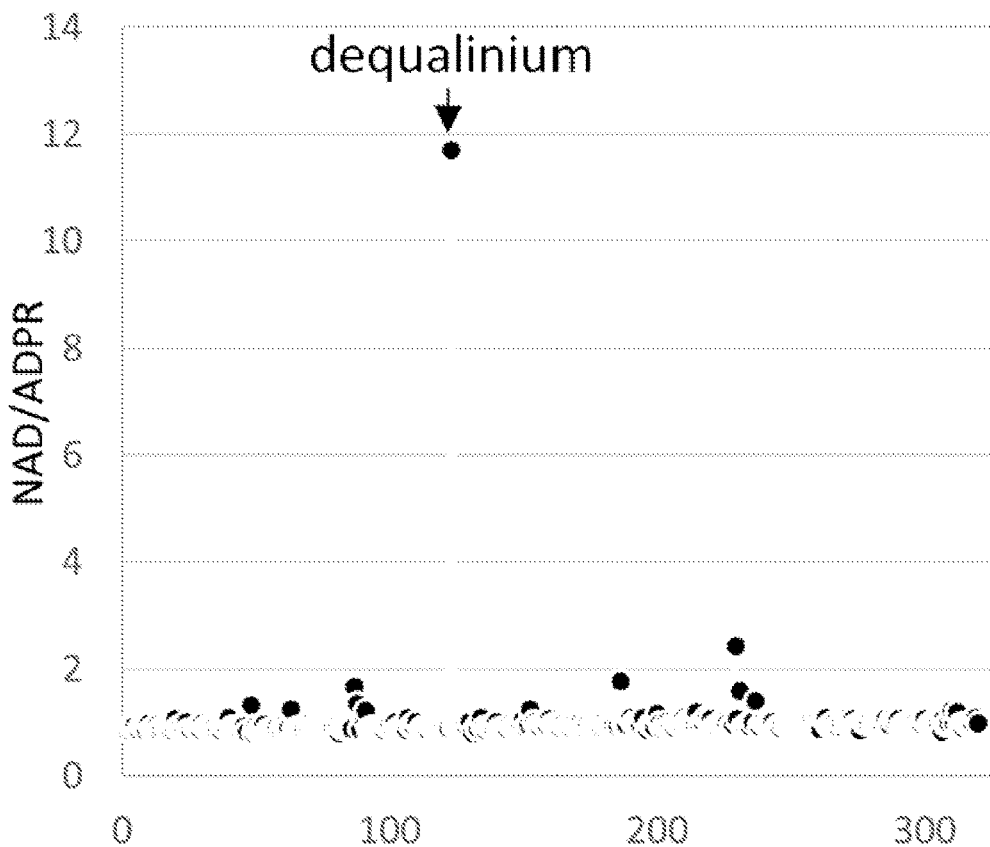
FIG. 10A, FIG. 10B, FIG. 10C and FIG. 10D shows the identification of TcpC inhibitors from Pharmacon library.
Figure 10B:
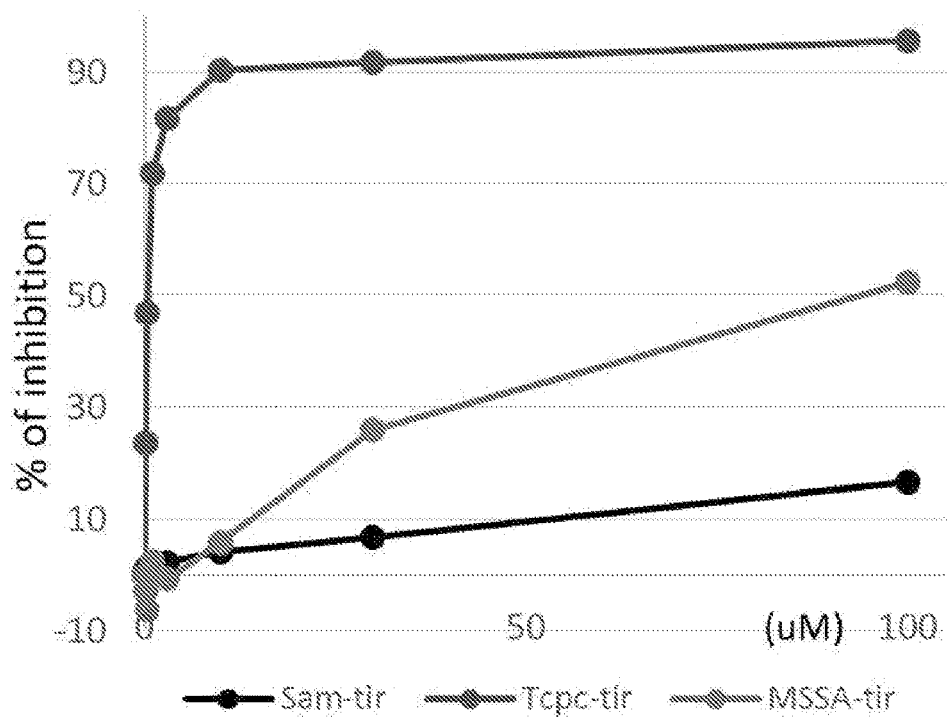
Figure 10C:
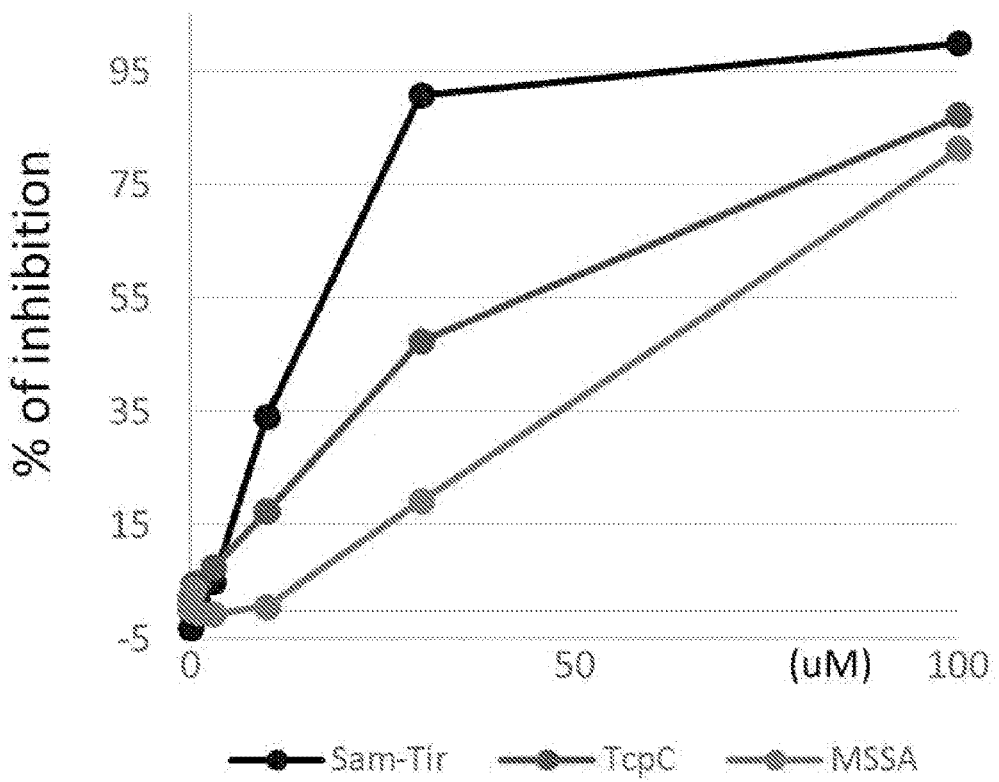
Figure 10D:
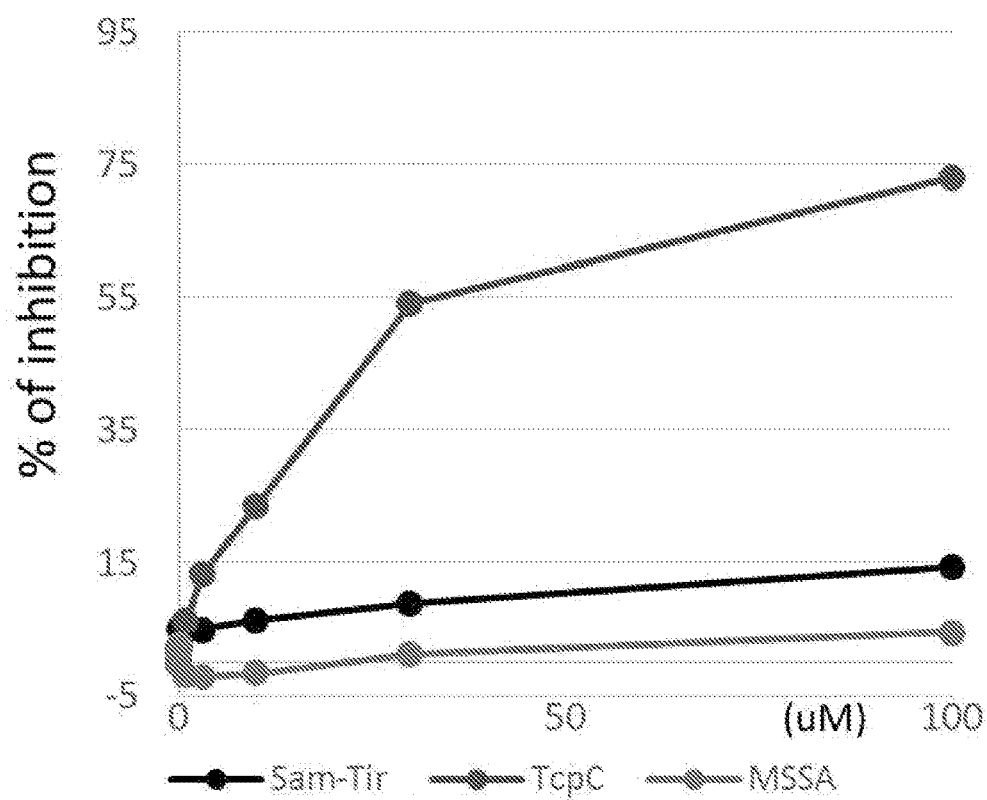
Figure 11A:
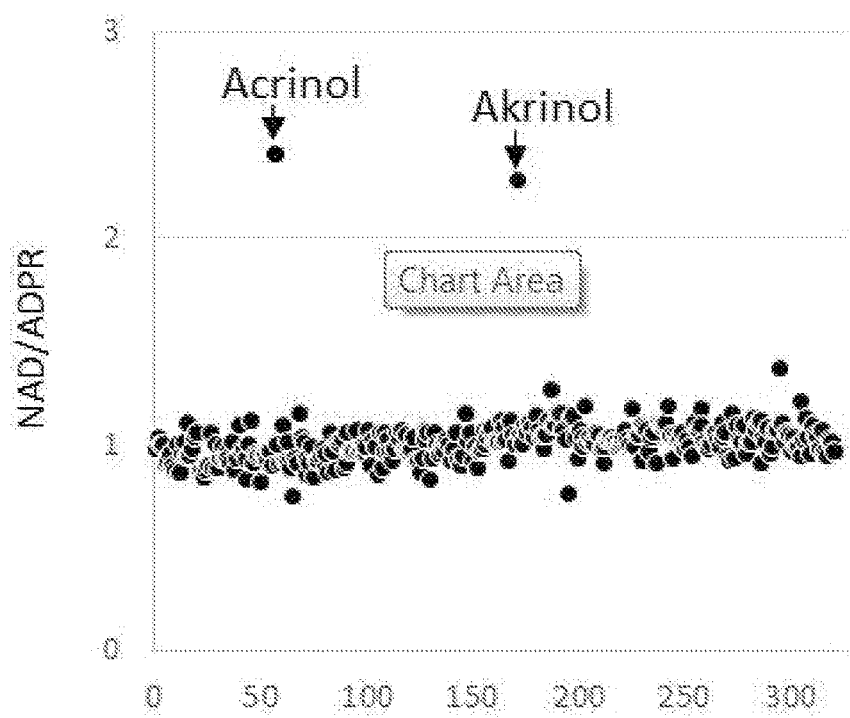
FIG. 11A, FIG. 11B, FIG. 11C and FIG. 11D depicts the screen for inhibitors of the NADase activity of TirS from *S. aureus*.
Figure 11B:
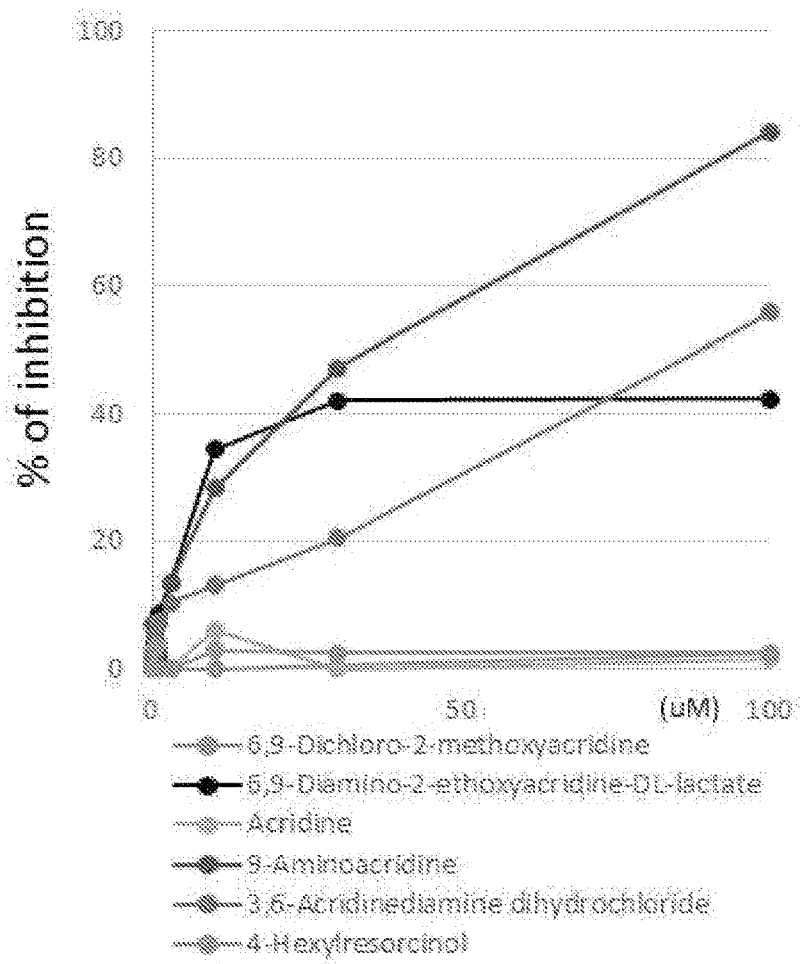
Figure 11C:
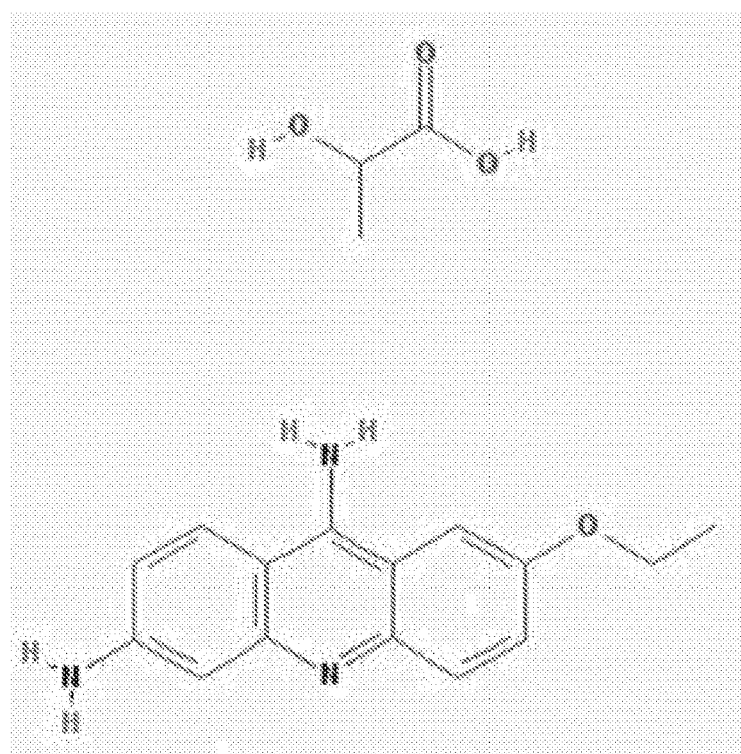
Figure 11D:
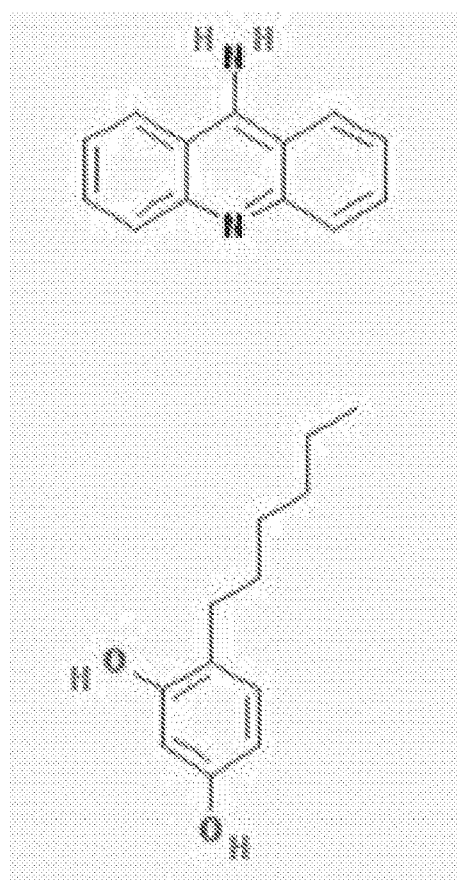

MS/MS analysis was then used to further analyze the ion with m/z 542. We found that the major product ion had an m/z of 136, which likely corresponds to the adenine moiety of NAD$^+$ (FIG. 3H). MS/MS spectra of standard cADPR showed a very similar fragmentation pattern to that of Metabolite X (FIG. 3H). To extend this analysis, we collected HPLC fractions corresponding to the Metabolite X peak in lysates prepared from E. coli expressing TcpO-TIR, AbTir-TIR, and Btpa-TIR. MS/MS analysis of these fractions showed the signature m/z 542/136 ion pair was produced by each of these TIR domains (FIG. 9C-9E).

These analyses indicate that a subset of prokaryotic TIR domains produce a variant of cADPR (Metabolite X) from NAD$^+$ cleavage. The generation of cADPR by ADP-Ribosyl cyclases including the cyclase from *Aplysia californica*, and mammalian CD38 occurs via cyclization at the N1 position of the adenine ring (Graeff et al., 2009; Lee et al., 1994). However, CD38 can cyclize nicotinamide guanine dinucleotide (NGD), an NAD+ analog, using the N7 position of the guanine ring to produce N7-cGDPR (Graeff et al., 1996). Taken together with all of our metabolite analysis, it is likely that the variant cADPR (Metabolite X) is N7-cADPR (FIG. 3I), a previously unreported molecule. Taken together, our results show that prokaryotic TIR domains are NAD$^+$ consuming enzymes, and that remarkable diversity in the reaction products exists even within TIRs from the same domain of life. Future studies should provide more insights into the structure of the variant cADPR molecule and how prokaryotic TIRs produce this unique reaction product.

Full length TirS from *Staphylococcus aureus* induces NAD$^+$ loss in mammalian cells.

Figure 4A:
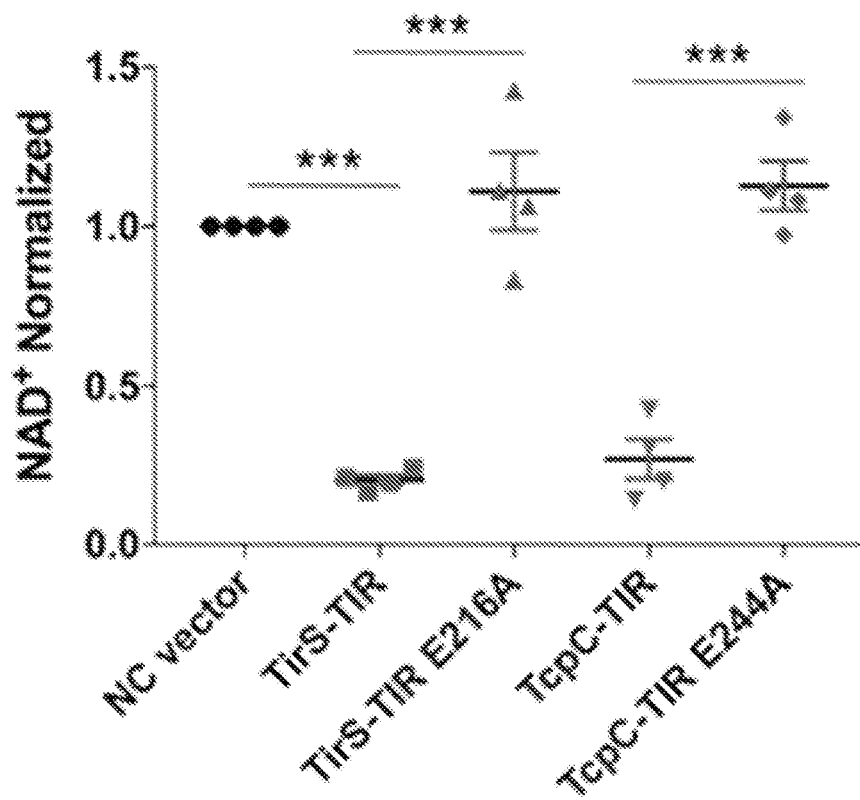
FIG. 4A, FIG. 4B, FIG. 4C, FIG. 4D, FIG. 4E, FIG. 4F and FIG. 4G show Full-length TirS from *Staphylococcus aureus* induces $NAD^+$ loss in mammalian HEK293T cells.
Figure 4B:
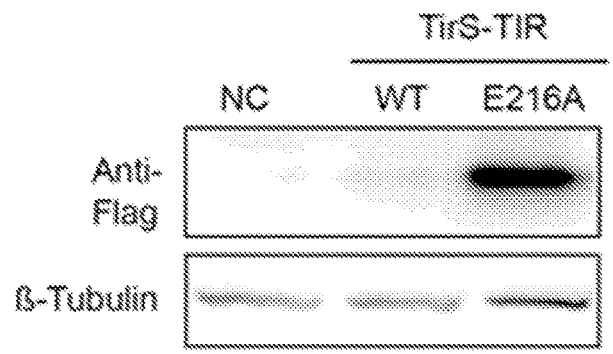
Figure 4B:
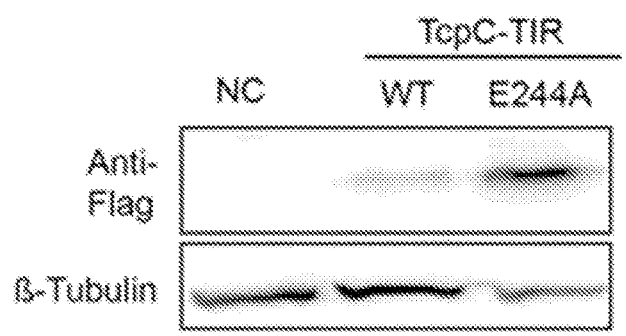

A number of bacterial TIR domain proteins have been identified as secreted virulence factors (Askarian et al., 2014; Cirl et al., 2008; Patot et al., 2017). With the discovery that prokaryotic TIR domains function enzymatically to cleave NAD$^+$, we tested TIR domain proteins associated with microbial virulence for their ability to degrade NAD$^+$ in mammalian cells. First, we transiently expressed S. aureus TirS-TIR and E. coli TcpC-TIR in HEK293T cells, extracted metabolites, and measured NAD$^+$ levels by HPLC. Consistent with results using purified recombinant protein in in vitro assays, we found that both wild type TirS-TIR and wild type TcpC-TIR induced NAD$^+$ loss these cells (FIG. 4A). Moreover, this decline in NAD$^+$ was not observed when catalytically dead mutant TirS-TIR or TcpC-TIR were transfected (FIG. 4A), indicating that the drop in NAD$^+$ is due to intrinsic enzymatic activity of these TIR domains. We examined expression of these wildtype and mutant TIR domains and found that the mutants were expressed at remarkably higher levels (FIG. 4B), supporting the idea that mammalian cells grow poorly when expressing these potent NADases.

Figure 4C:
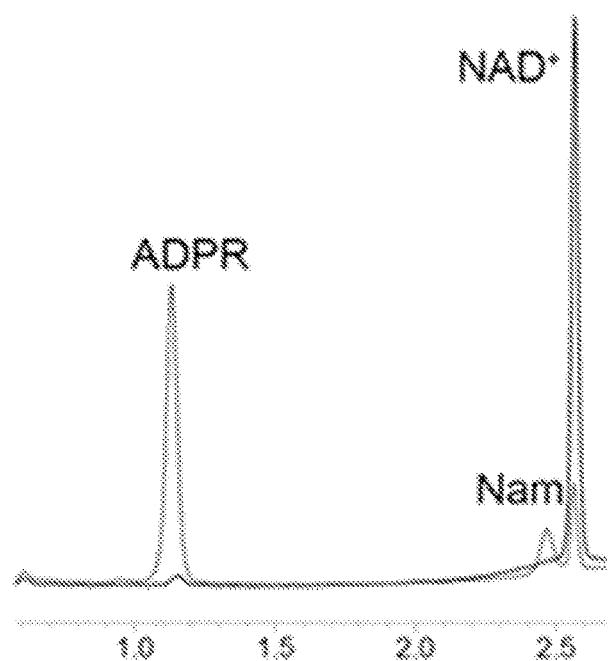
Figure 4D:
Figure 4D:
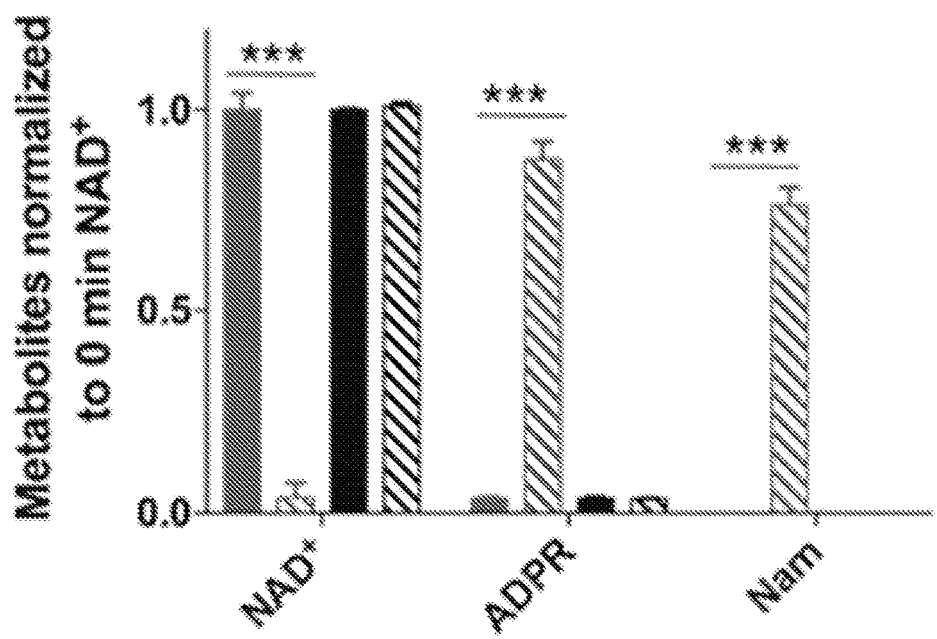
Figure 4E:
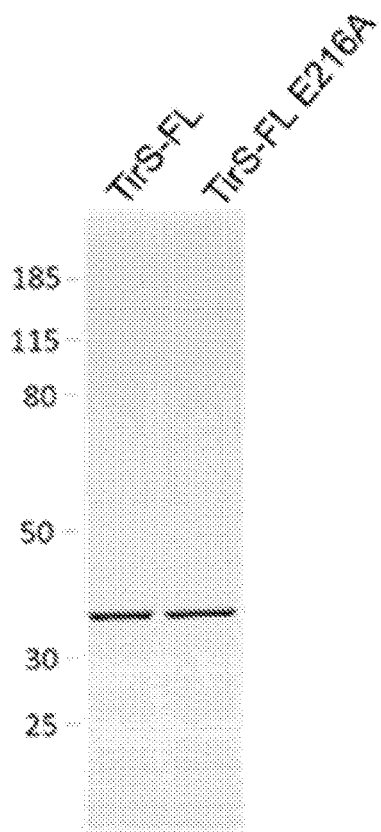

With confirmation that these prokaryotic TIR domains are active in mammalian cells, we set out to examine the effects of expressing the full-length S. aureus TirS virulence factor (TirS-FL) in HEK293T cells. First, we asked if TirS-FL purified from our cell-free protein translation system was able to cleave NAD+ in vitro. We found that wild type TirS-FL cleaves NAD$^+$, whereas the mutant TirS-FL (E216A) was enzymatically inactive (FIG. 4C-4E). Similar to the purified TIR-only protein, HPLC analysis showed that TirS-FL cleaves NAD$^+$ into Nicotinamide and ADP-Ribose (FIG. 4C and FIG. 4D).

Figure 4F:
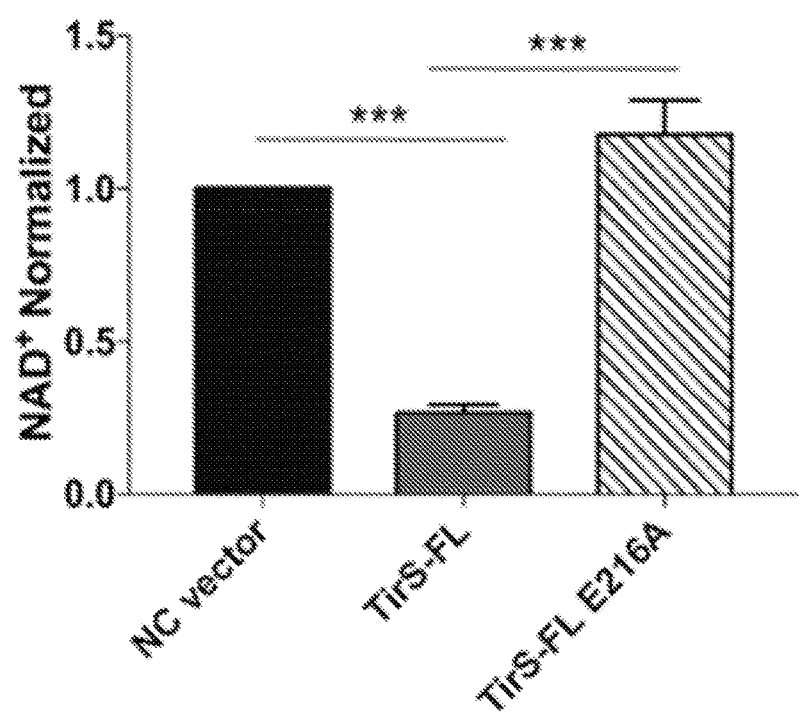
Figure 4G:
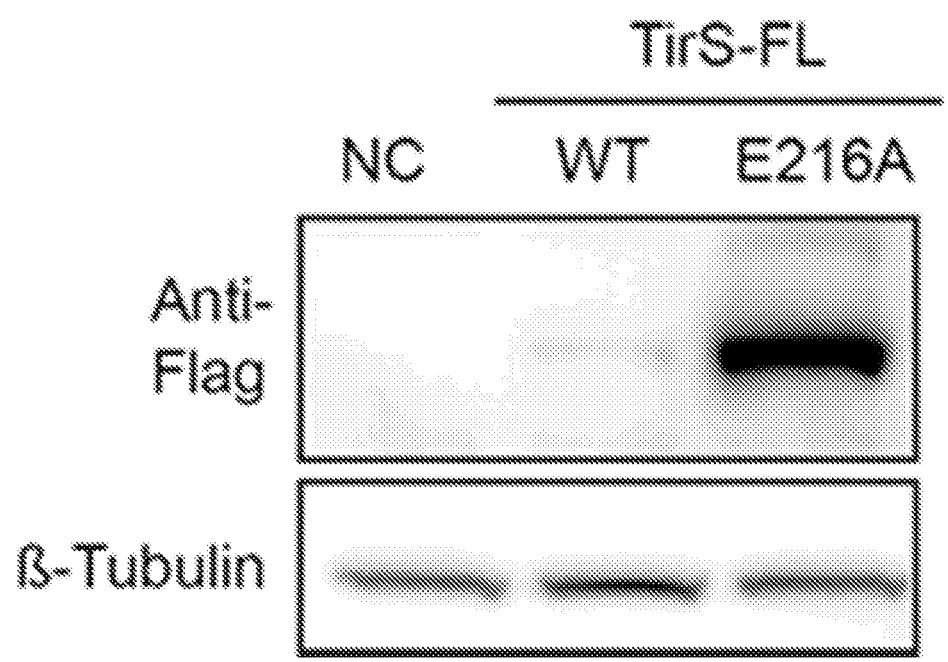

To test if TirS-FL could induce NAD$^+$ loss in mammalian cells, we transiently expressed it in HEK293T cells, extracted metabolites, and measured NAD$^+$ levels. Consistent with data generated in vitro and in bacteria, we found that wild type TirS-FL induced NAD$^+$ loss in mammalian cells, whereas enzymatically dead TirS-FL E216A did not (FIG. 4F, FIG. 4G). Again, we observed that the wildtype protein was expressed at much lower levels in HEK293T cells than its catalytically inactive mutant (FIG. 4G), suggesting that TirS is toxic to its mammalian host. These findings suggest that TIR domain proteins identified as virulence factors could promote virulence via their NADase activity and that therapeutic interventions targeting TIR NADases in pathogenic bacteria could restrict infections caused by these organisms.

Example 2

Identification of Inhibitors of TcpC and TirS NADase Activity

NRK1-HEK293T cells represent a polyclonal cell line that has been stably transfected with an FCIV expression vector that expresses human Nicotinamide Riboside Kinase 1 (NRK1), an enzyme that converts the NAD$^+$ biosynthetic precursor nicotinamide riboside (NR) to NMN, the immediate precursor of NAD⁺. When these NRK1-expressing cells are supplemented with NR, NAD⁺ levels are augmented and cell viability is enhanced to enable efficient production and purification of the constitutively active TcpC TIR protein fragment. NRK1-HEK293T cells were seeded onto 150 cm2 plates at 20×106 cells per plate. The next day, the cells were transfected with 15 μg FCIV-TcpC TIR (TcpC TIR expression plasmid) using X-tremeGENE 9 DNA Transfection Reagent (Roche product #06365787001). The cultures were supplemented with 1 mM NR at time of transfection to minimize toxicity from TcpC-TIR overexpression. Forty-eight hours after transfection, cells were harvested, pelleted by centrifugation at 1,000 rpm (Sorvall ST 16R centrifuge, Thermo Fisher), and washed once with cold PBS (0.01 M phosphate buffered saline NaCl 0.138 M; KCl 0.0027 M; pH 7.4). The cells were resuspended in PBS with protease inhibitors (Complete protease inhibitor cocktail, Roche product #11873580001) and cell lysates were prepared by sonication (Branson Sonifer 450, output=3, 20 episodes of stroke). The lysates were centrifuged (12,000×g for 10 min at 4° C.) to remove cell debris and the supernatants (containing TcpC-TIR protein) were stored at −80° C. for later use in the in vitro NADase assay (see below). Protein concentration was determined by the Bicinchoninic (BCA) method and used to normalize lysate concentrations.

Reaction mixtures were prepared by mixing TcpC-TIR cell lysate (0.9 μg total protein), test compound stock (25 μM final concentration, from Pharmakon library), and PBS (pH 7.4) to a final volume of 12 μl. NAD (10 μM final concentration) was then added for a final reaction volume of 20 μl. The reaction was incubated at 37° C. for 60 min, and then stopped by addition of 180 μl of 0.55 M perchloric acid (HClO4) and placed on ice. After 10 min on ice, the reaction plates were centrifuged for 10 min at 4,000 rpm (Sorvall ST 16R centrifuge). The supernatant (120 μl) was transferred to a new plate and 10 μl of 3M K2CO3 was added to neutralize the solution. Precipitated salts were removed by centrifugation 10 min at 4,000 rpm (Sorvall ST 16R centrifuge). The supernatant was transferred and analyzed by HPLC (Shimadzu Nexera X2) to quantify the amounts of NAD and ADPR, a product of the cleavage reaction, in each sample. From these values, the NAD/ADPR ratio was calculated for each compound as a measure of NAD cleavage activity. This ratio was compared to the ratio generated in the absence of compound inhibitors. A reduction of NADase activity (NAD/ADPR ratio >2) was used to identify compounds that inhibited the TcpC-TIR catalyzed NAD cleavage. A total of 320 drugs from Pharmakon library (MicroSource Discovery Systems, Inc.) were screened as candidate inhibitors of TcpC-Tir.

Positive hits were individually purchased from Sigma and tested its dose dependent inhibition in conditions described above. SARM1 Sam-Tir lysate and MSSA Tir were also used to test if these compounds could block these Tir NADase activities as well. Three inhibitors (dequalinium, cetylpyridium, and amiloride) are shown in FIG. 10.

The same protocol was used to screen for *S. aureus* TirS inhibitors, except that the TirS protein was generated using an in-vitro translation system (New England Biolab E6800). For this, 25 μl reactions containing 500 ng TirS DNA and 20 units RNase Inhibitor were incubated at 37° C. for 2.5 hours with the in vitro translation system, and the protein that was produced was used for screen. The original solution was diluted 250 fold and 1 ul of diluted solution was used for each 20 ul reaction (10 uM NAD, 25 uM compound, 37° C. for 60 min).

Two hits (acrinol and akrinol) were obtained following screening of 960 drugs from the Pharmakon library (FIG. 11). Both drugs possess an acridine moiety, so additional compounds containing this structure were tested as candidate inhibitors of TirS. 9-aminoacridine and 2-ethoxy-6,9-diaminoacridine monolactate monohydrate (Acrinol) both inhibit TirS with an IC50 of about 30□M. Neither of these drugs inhibited SARM1 (Sam-Tir) or TcpC TIR NADase activity (data not shown).

Example 3

Preliminary Screen of Microbial TIR NADases

Preliminary counts indicate at least, about 137 new microbial TIRs have been tested and run on HPLC, with 26 shown as positive hits for NADase activity. That represents a 19% positive hit rate. The positive hits are shown below in Table 2.

TABLE 2

Microbial TIR NADases

| Organism | Gene/Protein |
|---|---|
| Coprococcus_eutactus_ATCC_27759 | gi\|2991\|ref\|COPEUT_02740\| hypothetical protein |
| Proteus_penneri_ATCC_35198 | gi\|3821\|ref\|PROPEN_03896\| hypothetical protein |
| Bacteroides_thetaiotaomicron_3731 | gi\|5683\|ref\|AMN69_RS28245\| hypothetical protein |
| Eubacterium_hallii_DSM_3353 | gi\|446\|ref\|EUBHAL_RS02150\| TIR domain-containing protein |
| Bacteroides_thetaiotaomicron_3731 | gi\|1307\|ref\|AMN69_RS06490\| hypothetical protein |
| Bacteroides_xylanisolvens_XB1A | gi\|3630\|ref\|BXY_39700\| MTH538 TIR-like domain (DUF1863). |
| Clostridium_scindens_ATCC_35704 | gi\|726\|ref\|CLOSCI_02130\| SEFIR domain protein |
| Dorea_formicigenerans_ATCC_27755 | gi\|1847\|ref\|DORFOR_RS09155\| TIR domain-containing protein |
| Providencia_rustigianii_DSM_4541 | gi\|533\|ref\|PROVRUST_05034\| hypothetical protein |
| Bacteroides_coprophilus_DSM_18228 | gi\|713\|ref\|BACCOPRO_00713\| SEFIR domain protein |
| Bacteroides_thetaiotaomicron_7330 | gi\|632\|ref\|Btheta7330_RS03065\| TIR domain-containing protein |
| Bacteroides_thetaiotaomicron_7330 | gi\|4887\|ref\|Btheta7330_RS23835\| hypothetical protein |
| Roseburia_intestinalis_L1-82 | gi\|2906\|ref\|ROSINTL182_07906\| hypothetical protein |
| Bacteroides_ovatus_ATCC_8483 | gi\|5057\|ref\|BACOVA_05060\| hypothetical protein |
| Clostridium_bolteae_ATCC_BAA-613 | gi\|1498\|ref\|CLOBOL_01188\| hypothetical protein |
| Eubacterium_cylindroides_DSM_3983 | gi\|308\|ref\|HMPREF0367_01592\| Sel1 repeat protein |
| Enterococcus phage EFC-1 | TIR protein [Enterococcus phage EFC-1] |
| Cyanothece sp. (strain PCC 8801) | Middle23_0 (Putative lipoprotein) |
| Leptolyngbya sp. PCC 7376 | Lepto7376_4317 (YD repeat protein) |
| Modestobacter marinus | MODMU_1704 (uncharacterized protein) |
| Scytonema sp. NIES-4073 | GUN4 domain-containing protein |
| Comamonas aquatica DA1877 | AX13_15130 (Uncharacterized protein) |
| Flavobacterium micromati | TIR domain containing protein (SAMN05444372_11431) |
| Lacunisphaera limnophila | Invasion protein regulator (Verru16b_00714) |
| Aquimarina amphilecti | Uncharacterized protein (SAMN04487910_4078) |
| Thioflavicoccus mobilis 8321 | Uncharacterized protein (Thimo_2887) |

What is claimed is:

1. A method of treating a microbial infection in a subject in need thereof, wherein the microbe encodes a TIR NADase, the method comprising: administering to said subject a therapeutically effective amount of pharmaceutical composition comprising a TIR NADase inhibitor wherein the TIR NADase inhibitor is one or more of:

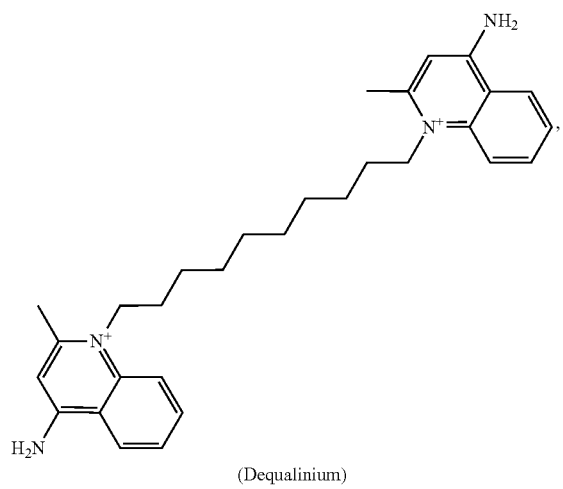

(Dequalinium)

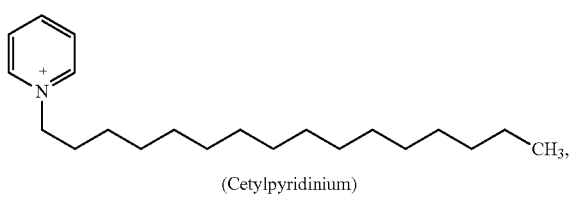

(Cetylpyridinium)

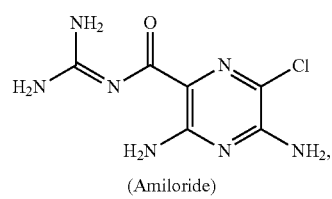

(Amiloride)

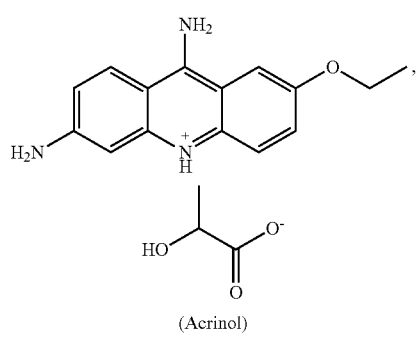

(Acrinol)

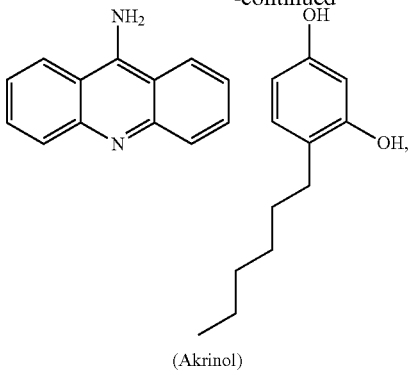

(Akrinol)

or pharmaceutically acceptable salts thereof.

2. The method of claim 1, wherein the TIR NADase inhibitor is Dequalinium

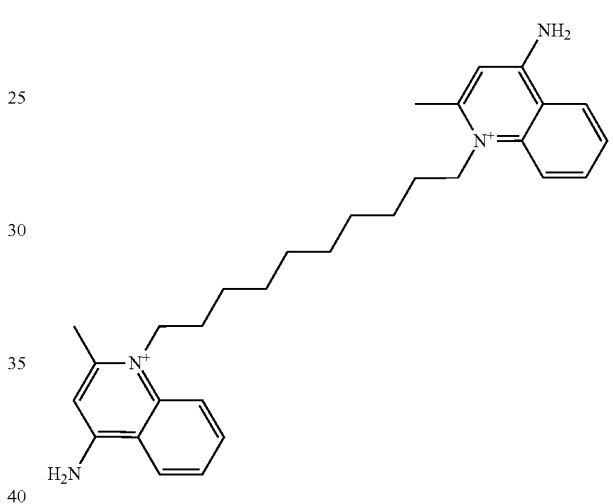

or pharmaceutically acceptable salts thereof.

3. The method of claim 1, wherein the TIR NADase inhibitor is Cetylpyridinium

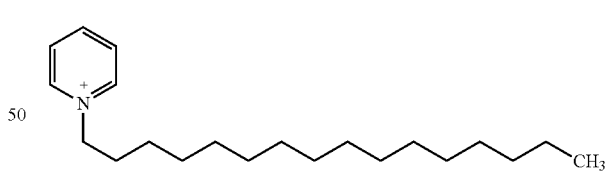

or pharmaceutically acceptable salts thereof.

4. The method of claim 1, wherein the TIR NADase inhibitor is Amiloride

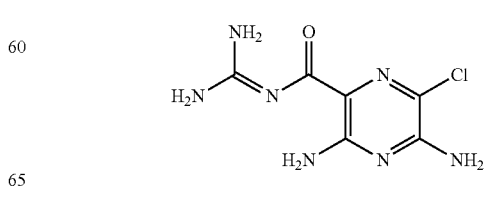

or pharmaceutically acceptable salts thereof.

5. The method of claim 1, wherein the TIR NADase inhibitor is Acrinol

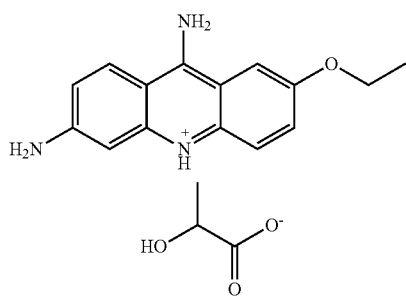

or pharmaceutically acceptable salts thereof.

6. The method of claim 1, wherein the TIR NADase inhibitor is Akrinol

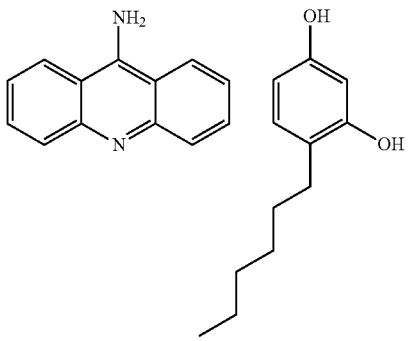

or pharmaceutically acceptable salts thereof.

7. The method of claim 1, wherein the infection is caused by a pathogenic bacteria, virus, fungus or protozoa.

8. The method of claim 7, wherein the bacteria is uropathogenic *E. coli*.

9. The method of claim 8, wherein the TIR NADase is TcpC.

10. The method of claim 7, wherein the bacteria is *S. aureus*.

11. The method of claim 10, wherein the TIR NADase is TirS.

* * * * *